United States Patent
Hosoi et al.

(10) Patent No.: US 9,782,412 B2
(45) Date of Patent: *Oct. 10, 2017

(54) PREVENTIVE AND/OR THERAPEUTIC AGENT OF IMMUNE DISEASE

(71) Applicant: TAIHO PHARMACEUTICAL CO., LTD., Chiyoda-ku (JP)

(72) Inventors: Fumihito Hosoi, Tsukuba (JP); Yoshinori Nakachi, Tsukuba (JP); Daisuke Kajiwara, Tsukuba (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/297,196

(22) Filed: Oct. 19, 2016

(65) Prior Publication Data

US 2017/0042900 A1 Feb. 16, 2017

Related U.S. Application Data

(63) Continuation of application No. PCT/JP2016/052732, filed on Jan. 29, 2016.

(30) Foreign Application Priority Data

Jan. 30, 2015 (JP) .................... 2015-017386

(51) Int. Cl.
*A61K 31/519* (2006.01)
*C07D 487/04* (2006.01)
*C07D 519/00* (2006.01)

(52) U.S. Cl.
CPC .......... *A61K 31/519* (2013.01); *C07D 487/04* (2013.01); *C07D 519/00* (2013.01)

(58) Field of Classification Search
CPC .................................. A61K 31/519
(Continued)

(56) References Cited

U.S. PATENT DOCUMENTS

2007/0135387 A1 6/2007 Michaelides et al.
2010/0249092 A1* 9/2010 Singh .............. C07D 239/47
514/210.18

(Continued)

FOREIGN PATENT DOCUMENTS

EP 2 947 086 A1 11/2015
JP 2009-518434 A 5/2009
(Continued)

OTHER PUBLICATIONS

Akinleye "Ibrutinib and novel BTK inhibitors in clinical development" Journal of Hematology & Oncology, 2013, vol. 6, p. 59, http://www.jhoonline.org/content/6/1/59.*

(Continued)

*Primary Examiner* — Shengjun Wang
(74) *Attorney, Agent, or Firm* — Oblon, McClelland, Maier & Neustadt, L.L.P.

(57) ABSTRACT

Provided is a preventive and/or therapeutic agent for immune diseases containing a compound having a BTK inhibitory activity or a salt thereof, as an active ingredient. A preventive and/or therapeutic agent of immune diseases, comprising a compound represented by Formula (I), where (Continued)

$R_1$ to $R_3$, W, X, Y, Z, and n represent those as defined in the specification, or a salt thereof, as an active ingredient.

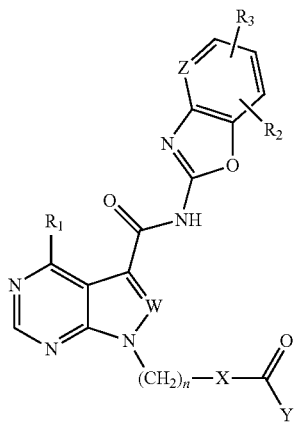

(I)

20 Claims, 5 Drawing Sheets

(58) Field of Classification Search
USPC .......................................... 514/262.1, 265.1
See application file for complete search history.

(56) References Cited

U.S. PATENT DOCUMENTS

| 2013/0018032 A1 | 1/2013 | Chen et al. |
| 2014/0343035 A1 | 11/2014 | Sagara et al. |
| 2016/0115168 A1 | 4/2016 | Iguchi et al. |

FOREIGN PATENT DOCUMENTS

| JP | 2014-520863 A | 8/2014 |
| WO | WO 2008/054827 A1 | 5/2008 |
| WO | WO 2009/057733 A1 | 5/2009 |
| WO | WO 2009/158571 A1 | 12/2009 |
| WO | WO 2011/090760 A1 | 7/2011 |
| WO | WO 2013/108809 A1 | 7/2013 |
| WO | WO 2014/036016 A1 | 3/2014 |
| WO | WO 2015/022926 A1 | 2/2015 |

OTHER PUBLICATIONS

Barbera et al. "Current treatment of rheumatoid arthritis. Perspectives for the development of antigen-specific therapies," Biotechnologia Applicada, 2012, vol. 29, pp. 146-154.*
International Search Report dated May 10, 2016, in PCT/JP2016/052732, filed Jan. 29, 2016.
Schaeffer and Schwartzberg, Curr. Op. Imm., 2000, pp. 282-288.
Schmidt U., et al., Int Arch Allergy Immunol, 134, 2004.
Ellmeier W., et al., FEBS Journal., 278, 2011.
Rommel C., et al., Nature reviews immunology, 7, 2007.
Honigberg LA., et al., Proc. Natl. Acad. Sci. USA, 107, 2010.
Keefe DM and Bateman EH. Nature Reviews Clinical Oncology. 9, 2012.
European Search Report issued on Apr. 26, 2017, in European Patent Application No. 16743556.9.
Anonymous: "What is lymphoma? Lymphoma causes, symptoms and treatments—Medical News Today", Nov. 28, 2014, XP055363825, Retrieved from the Internet: URL: https://web.archive.org/web/20141227103936/http://www.medicalnewstoday.com/articles/146136.php [retrieved on Apr. 11, 2017], pp. 1-10.
Anonymous: "The immune system and cancer: Cancer Research UK", Oct. 29, 2014, XP055363816, Retrieved from the Internet: URL: http//www.cancerresearchuk.org/about-cancer/what-is-cancer/body-systems-and-cancer/the-immune-system-and-cancer [retrieved on Apr. 11, 2017], pp. 1-8.

* cited by examiner

US 9,782,412 B2

PREVENTIVE AND/OR THERAPEUTIC AGENT OF IMMUNE DISEASE

TECHNICAL FIELD

The present invention relates to a preventive and/or therapeutic agent of immune diseases, particularly, a preventive and/or therapeutic agent of allergic diseases or autoimmune diseases, comprising a novel fused pyrimidine compound or a salt thereof which has Bruton's tyrosine kinase (BTK) inhibitory effect, as an active ingredient.

BACKGROUND ART

It is known that various protein kinases exist in vivo and are involved in the regulation of a variety of functions. Bruton's tyrosine kinase (BTK) is a protein kinase that belongs to Tec kinase family, which is expressed in myeloid cells such as B-cells, monocyte/macrophages, neutrophils, mast cells and osteoclasts, and is involved in regulating functions of these cells (Non-Patent Literatures 1 and 2). BTK is located in the downstream of the immunereceptor signals such as B-cell receptor (BCR) or Fc receptor (FcR) family, being involved in the proliferation, survival, differentiation and activation of B-cells, and involved in regulating expression of inflammatory cytokines (for example, tumor necrosis factor-α or interleukin-1β) or chemical mediators (for example, histamine or leukotriene) in monocyte/macrophage or in mast cells (Non-Patent Literature 3). An inhibitor capable of regulating BTK activity is considered to be useful as a therapeutic agent for diseases associated with abnormal hyperactivity of BTK signaling pathway (for example, cancer, allergic diseases, or autoimmune diseases).

In recent years, it has been considered that, in addition to B-cells which are involved in antibody production, various cells such as monocytes/macrophages, neutrophils, mast cells and osteoclasts, which express Fc receptor (FcR) family or its related molecules, are closely associated with incidence or progress of autoimmune diseases such as rheumatoid arthritis (Non-Patent Literature 4). Since BTK signals are associated with activation of these cells or abnormal activation of functions thereof (Non-Patent Literatures 2 and 3), it is expected that a compound with BTK inhibitory effect has a therapeutic efficacy against autoimmune diseases. In addition, since BTK is also involved in activation of mast cells, it is expected that a compound with BTK inhibitory effect has a therapeutic efficacy against allergic diseases with which B-cells or mast cells are associated.

Currently known BTK inhibitors include PCI-32765 (Non-Patent Literature 5) and the compounds described in Patent Literatures 1 and 2 (Patent Literatures 1 and 2). The PCI-32765 is known to inhibit EGFR as well as BTK, and to be a compound useful as a therapeutic agent for immune diseases (such as rheumatoid arthritis) (Non-Patent Literature 5).

Meanwhile, it is known that EGFR binds to, for example, epidermal growth factor (EGF) which is a ligand, and participates in the proliferation and survival (for example, inhibition of apoptosis) of various cells (Non-Patent Literature 6). It is known that inhibitors targeting EGFR cause adverse effects such as skin disorders and gastrointestinal dysfunction in common, and it is widely supposed that these adverse effects may be related to the inhibition of the wild type EGFR signaling pathway (Non-Patent Literature 7), and therefore, an inhibitor which has a high BTK selectivity and is highly useful has been desired as a preventive and/or therapeutic agent of immune diseases.

CITATION LIST

Patent Literatures

Patent Literature 1: WO 2011/090760
Patent Literature 2: WO 2009/158571

Non-Patent Literatures

Non-Patent Literature 1: Schaeffer and Schwartzberg, Curr. Op. Imm., 2000, pp. 282-288
Non-Patent Literature 2: Schmidt U., et al., Int Arch Allergy Immunol, 134, 2004
Non-Patent Literature 3: Ellmeier W., et al., FEBS Journal., 278, 2011
Non-Patent Literature 4: Rommel C., et al., Nature reviews immunology, 7, 2007
Non-Patent Literature 5: Honigberg L A., et al., Proc. Natl. Acad. Sci. USA, 107, 2010
Non-Patent Literature 6: Lacouture M E., Nature Reviews Cancer, 6, 2006
Non-Patent Literature 7: Keefe D M and Bateman E H. Nature Reviews Clinical Oncology. 9, 2012

SUMMARY OF INVENTION

Technical Problem

If the inhibitory activities against BTK and EGFR are separated from each other, it is possible to expect reduction of the adverse effects as mentioned above.

That is, from the viewpoint of reducing adverse effects, a preventive and/or therapeutic agent of immune diseases that has a high inhibitory activity against BTK with low inhibitory activities against other kinases such as EGFR, which is at the same time excellent in efficacy, has been desired.

Thus, an object of the present invention is to provide a preventive and/or therapeutic agent of immune diseases having a better effect against immune diseases than that of a conventional BTK inhibitor with reduced adverse effects, particularly, a preventive and/or therapeutic agent of allergic diseases or autoimmune diseases.

Solution to Problem

As a result of extensive researches, the inventors of the present invention have found that compounds represented by the following general formula (I) exhibit an excellent inhibitory activity against BTK and an excellent selectivity for BTK, and are useful as a medical drug for treating autoimmune diseases such as rheumatoid arthritis or systemic lupus erythematosus, or immune diseases such as allergic disease, for example, atopic dermatitis, and have accomplished the present invention.

Specifically, the present invention provides a preventive and/or therapeutic agent of immune diseases which comprises the compound represented by the following general formula (I), or a salt thereof as an active ingredient:

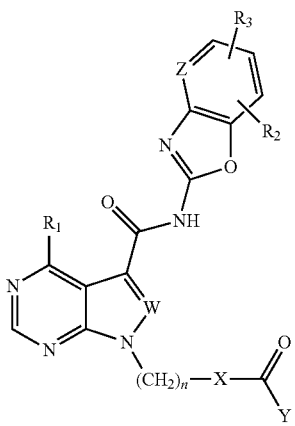

(I)

where X represents a nitrogen-containing C3-C10 heterocycloalkylene which may have one or more substituents;
Y represents —C($R_4$)=C($R_5$)($R_6$) or —C≡C—$R_7$;
W and Z each independently represent N or CH;
n represents an integer from 0 to 2;
$R_1$ represents an amino group which may have one or more substituents;
$R_2$ and $R_3$, which may be identical or different, each represent a hydrogen atom, a halogen atom, a C1-C6 alkyl group which may have one or more substituents, a C1-C6 alkoxy group which may have one or more substituents, a C3-C7 cycloalkyl group which may have one or more substituents, a C6-C14 aromatic hydrocarbon group which may have one or more substituents, a 4- to 10-membered monocyclic or polycyclic unsaturated heterocyclic group containing 1 to 3 heteroatoms of the same kind or different kinds selected from the group consisting of a nitrogen atom, an oxygen atom and a sulfur atom, which heterocyclic group may have one or more substituents, or a cyano group; and
$R_4$, $R_5$, $R_6$ and $R_7$, which may be identical or different, each represent a hydrogen atom, or a C1-C6 alkyl group which may have one or more substituents.

The present invention also provides a compound represented by the above general formula (I) or a salt thereof for prevention and/or treatment of immune diseases.

The present invention also provides use of the compound represented by the above general formula (I) or a salt thereof for production of preventive and/or therapeutic agent of immune diseases.

The present invention also provides a method for preventing and/or treating immune diseases, characterized by administering a compound represented by the above general formula (I) or a salt thereof.

As mentioned above, the PCI-32765 is known as a BTK inhibitor, and characterized by having a phenoxyphenyl group; however, it is significantly different from the compound of the present invention in view of lacking a benzoxazole group or an oxazolopyridine group, which represents a feature of the compound of the present invention. Furthermore, the compound of the present invention is characterized by having a higher BTK selectivity than that of PCI-32765 (Reference compound 1), as described later.

Furthermore, the compounds described in Patent Literatures 1 and 2 also lack the benzoxazole group or the oxazolopyridine group, which is a feature of the compound of the present invention, and their structures are significantly different.

Furthermore, the compound disclosed in WO 2007/067781 is known.

However, the compounds disclosed therein are those which inhibit aurora kinases, and there is no disclosure of any specific compound having a benzoxazole group or an oxazolopyridine group. The Literature is also silent on the presence or absence of the BTK inhibitory activity or usefulness of a preventive and/or therapeutic agent of immune diseases.

Advantageous Effects of Invention

According to the present invention, provided is a preventive and/or therapeutic agent of immune diseases, particularly, allergic diseases or autoimmune diseases, which contains a novel compound represented by the above formula (I) or a salt thereof, which is useful as a BTK inhibitor, as an active ingredient.

It has been made clear that the compound of the present invention or a salt thereof has an excellent BTK inhibitory activity and exhibits an excellent efficacy in an immunological disease model. Furthermore, since the compound of the present invention or a salt thereof strongly inhibits BTK selectively over EGFR, adverse effects can be reduced, and enhancement of safety can be expected. Therefore, the compound of the present invention or a salt thereof is useful as a preventive and/or therapeutic agent of immune diseases, particularly, as a preventive and/or therapeutic agent of allergic diseases or autoimmune diseases.

DESCRIPTION OF EMBODIMENT

Figure 1:
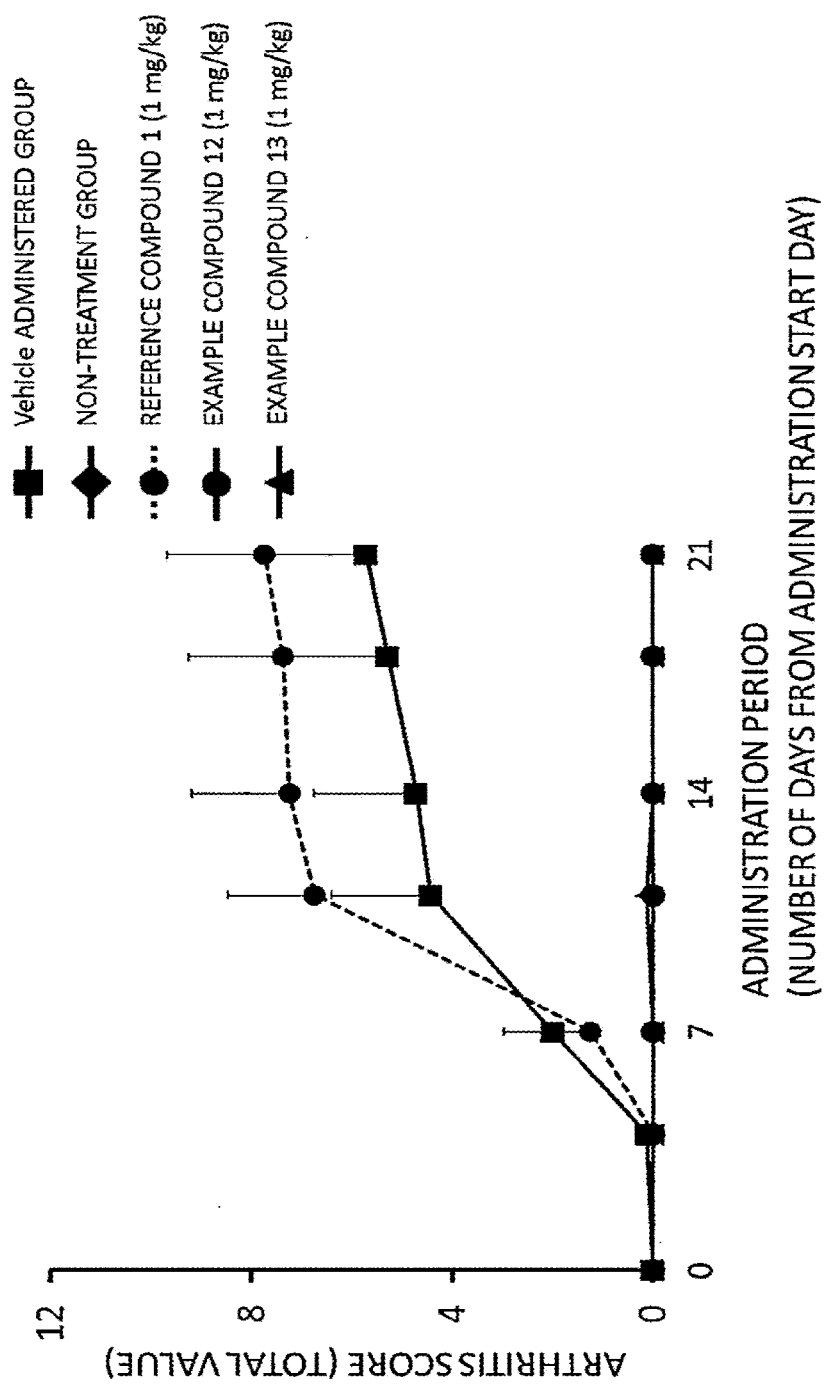
FIG. 1 illustrates effects in mouse collagen-induced arthritis models (preventive effect).

The compound represented by the above-described formula (I) of the present invention is a compound having a 1H-pyrazolo[3,4-d]pyrimidine skeleton or a 7H-pyrrolo[2,3-d]pyrimidine skeleton, which is substituted with a benzoxazole group or an oxazolopyridine group as one or more substituents linked via an amide bond, and the compound is a novel compound that has never been described in any of the prior art citations mentioned above.

According to the present specification, examples of the "substituent(s)" include a halogen atom, a hydroxyl group, a cyano group, a nitro group, an alkyl group, a halogenoalkyl group, a cycloalkyl group, a cycloalkyl-alkyl group, an aralkyl group, an alkenyl group, an alkynyl group, an alkoxy group, a halogenoalkoxy group, a cycloalkoxy group, a cycloalkyl-alkoxy group, an aralkyloxy group, an alkylthio group, a cycloalkyl-alkylthio group, an amino group, a mono- or dialkylamino group, a cycloalkyl-alkylamino group, an acyl group, an acyloxy group, an oxo group, a carboxyl group, an alkoxycarbonyl group, an aralkyloxycarbonyl group, a carbamoyl group, a saturated or unsaturated heterocyclic group, an aromatic hydrocarbon group, and a saturated heterocyclic oxy group. When the above-mentioned substituents are present, the number of the substituents is typically 1, 2 or 3.

Examples of the "halogen atom" according to the present specification include a fluorine atom, a chlorine atom, a bromine atom, and an iodine atom.

The "alkyl group" according to the present specification may be any of a linear group or a branched group, and examples thereof include C1-C6 alkyl groups such as a methyl group, an ethyl group, an n-propyl group, an isopropyl group, an n-butyl group, an isobutyl group, a tert-butyl group, an n-pentyl group, an isopentyl group, and a hexyl group.

The "halogenoalkyl group" according to the present specification is a linear or branched alkyl group having 1 to 6 carbon atoms and 1 to 13 halogen atoms (halogeno-C1-C6 alkyl group), and examples thereof include halogeno-C1-C6 alkyl groups such as a fluoromethyl group, a difluoromethyl group, a trifluoromethyl group, a trichloromethyl group, a fluoroethyl group, a 1,1,1-trifluoroethyl group, a monofluoro-n-propyl group, a perfluoro-n-propyl group, and a perfluoroisopropyl group, while preferred examples include halogeno-C1-C4 alkyl groups.

Specific examples of the "cycloalkyl group" according to the present specification include C3-C7 cycloalkyl groups such as cyclopropyl, cyclobutyl, cyclopentyl, cyclohexyl, and cycloheptyl. The "cycloalkylene" according to the present specification represents a divalent cycloalkyl.

Examples of the "cycloalkyl-alkyl group" according to the present specification include C3-C7 cyloalkyl-substituted C1-C4 alkyl groups such as a cyclopropylmethyl group, a cyclobutylmethyl group, a cyclopentylmethyl group, a cyclohexylmethyl group, and a cycloheptylmethyl group.

Examples of the "aralkyl group" according to the present specification include C7-C13 aralkyl groups such as a benzyl group, a phenethyl group, a naphthylmethyl group, and a fluorenylmethyl group.

The "alkenyl group" according to the present specification means an unsaturated hydrocarbon group which may be any of a linear group, a branched group or a cyclic group, and has at least one double bond. Examples thereof include C2-C6 alkenyl groups such as a vinyl group, an allyl group, a 1-propenyl group, a 2-methyl-2-propenyl group, an isopropenyl group, a 1-, 2- or 3-butenyl group, a 2-, 3- or 4-pentenyl group, a 2-methyl-2-butenyl group, a 3-methyl-2-butenyl group, a 5-hexenyl group, a 1-cyclopentenyl group, a 1-cyclohexenyl group, and a 3-methyl-3-butenyl group.

The "alkynyl group" according to the present specification means an unsaturated hydrocarbon group which may be any of a linear group, a branched group or a cyclic group, and has at least one triple bond. Examples thereof include C2-C6 alkynyl groups such as an ethynyl group, a 1- or 2-propynyl group, a 1-, 2- or 3-butynyl group, and a 1-methyl-2-propynyl group.

The "alkoxy group" according to the present specification may be any of a linear group or a branched group, and examples thereof include C1-C6 alkoxy groups such as a methoxy group, an ethoxy group, a propoxy group, an isopropoxy group, a butoxy group, an isobutoxy group, a tert-butoxy group, a pentyloxy group, an isopentyloxy group, and a hexyloxy group.

The "halogenoalkoxy group" according to the present specification is a linear or branched alkoxy group having 1 to 6 carbon atoms and 1 to 13 halogen atoms (halogeno-C1-C6 alkoxy group), and examples thereof include halogeno-C1-C6 alkoxy groups such as a fluoromethoxy group, a difluoromethoxy group, a trifluoromethoxy group, a trichloromethoxy group, a fluoroethoxy group, a 1,1,1-trifluoroethoxy group, a monofluoro-n-propoxy group, a perfluoro-n-propoxy group, and a perfluoro-isopropoxy group, while preferred examples include halogeno-C1-C4 alkoxy groups.

Specific examples of the "cycloalkoxy group" according to the present specification include C3-C7 cycloalkoxy groups such as a cyclopropoxy group, a cyclobutoxy group, a cyclopentyloxy group, a cyclohexyloxy group, and a cycloheptyloxy group.

Examples of the "cycloalkyl-alkoxy group" according to the present specification include C3-C7 cycloalkyl-substituted C1-C4 alkoxy groups such as a cyclopropylmethoxy group, a cyclobutylmethoxy group, a cyclopentylmethoxy group, a cyclohexylmethoxy group, and a cycloheptylmethoxy group.

Examples of the "aralkyloxy group" according to the present specification include C7-C13 aralkyloxy groups such as a benzyloxy group, a phenethyloxy group, a naphthylmethyloxy group, and a fluorenylmethyloxy group.

The "alkylthio group" according to the present specification may be any of a linear group or a branched group, and examples thereof include C1-C6 alkylthio groups such as a methylthio group, an ethylthio group, an n-propylthio group, an isopropylthio group, an n-butylthio group, an isobutylthio group, a tert-butylthio group, an n-pentylthio group, an isopentylthio group, and a hexylthio group.

Examples of the "cycloalkyl-alkylthio group" according to the present specification include C3-C7 cycloalkyl-substituted C1-C4 alkylthio groups such as a cyclopropylmethylthio group, a cyclobutylmethylthio group, a cyclopentylmethylthio group, a cyclohexylmethylthio group, and a cycloheptylmethylthio group.

Examples of the "monoalkylamino group" according to the present specification include amino groups that are monosubstituted with linear or branched C1-C6 alkyl groups, such as a methylamino group, an ethylamino group, an n-propylamino group, an isopropylamino group, an n-butylamino group, an isobutylamino group, a tert-butylamino group, an n-pentylamino group, an isopentylamino group, and a hexylamino group.

Examples of the "dialkylamino group" according to the present specification include amino groups that are disubstituted with linear or branched C1-C6 alkyl groups, such as a dimethylamino group, a diethylamino group, a di(n-propyl)amino group, a diisopropylamino group, a di(n-butyl)amino group, a diisobutylamino group, a di(tert-butyl)amino group, a di(n-pentyl)amino group, a diisopentylamino group, and a dihexylamino group.

Examples of the "cycloalkyl-alkylamino group" according to the present specification include C3-C7 cycloalkyl-substituted C1-C4 alkylamino groups such as a cyclopropylmethylamino group, a cyclobutylmethylamino group, a cyclopentylmethylamino group, a cyclohexylmethylamino group, and a cycloheptylmethylamino group.

The "acyl group" according to the present specification means an alkylcarbonyl group or an arylcarbonyl group.

Examples of the "alkylcarbonyl group" according to the present specification include linear or branched (C1-C6 alkyl)carbonyl groups such as methylcarbonyl, ethylcarbonyl, n-propylcarbonyl, isopropylcarbonyl, n-butylcarbonyl, isobutylcarbonyl, tert-butylcarbonyl, n-pentylcarbonyl, isopentylcarbonyl, and hexylcarbonyl.

Examples of the "arylcarbonyl group" according to the present specification include (C6-C13 aryl)carbonyl groups such as phenylcarbonyl, naphthylcarbonyl, fluorenylcarbonyl, anthrylcarbonyl, biphenylcarbonyl, tetrahydronaphthylcarbonyl, chromanylcarbonyl, 2,3-dihydro-1,4-dioxanaphthalenylcarbonyl, indanylcarbonyl, and phenanthrylcarbonyl.

The "acyloxy group" according to the present specification means an alkylcarbonyloxy group or an arylcarbonyloxy group.

Examples of the "alkylcarbonyloxy group" according to the present specification include linear or branched (C1-C6 alkyl)carbonyloxy groups such as methylcarbonyloxy, ethylcarbonyloxy, n-propylcarbonyloxy, isopropylcarbonyloxy, n-butylcarbonyloxy, isobutylcarbonyloxy, tert-butylcarbonyloxy, n-pentylcarbonyloxy, isopentylcarbonyloxy, and hexylcarbonyloxy.

Examples of the "arylcarbonyloxy group" according to the present specification include (C6-C13 aryl)carbonyloxy groups such as phenylcarbonyloxy, naphthylcarbonyloxy, fluorenylcarbonyloxy, anthrylcarbonyloxy, biphenylcarbonyloxy, tetrahydronaphthylcarbonyloxy, chromanylcarbonyloxy, 2,3-dihydro-1,4-dioxanaphthalenylcarbonyloxy, indanylcarbonyloxy, and phenanthrylcarbonyloxy.

The "alkoxycarbonyl group" according to the present specification may be any of a linear group or a branched group, and examples thereof include (C1-C6 alkoxy)carbonyl groups such as a methoxycarbonyl group, an ethoxycarbonyl group, a propoxycarbonyl group, an isopropoxycarbonyl group, a butoxycarbonyl group, an isobutoxycarbonyl group, a tert-butoxycarbonyl group, a pentyloxycarbonyl group, an isopentyloxycarbonyl group, and a hexyloxycarbonyl group.

Examples of the "aralkyloxycarbonyl group" according to the present specification include (C7-C13 aralkyl)oxycarbonyl groups such as a benzyloxycarbonyl group, a phenethyloxycarbonyl group, a naphthylmethyloxycarbonyl group, and a fluorenylmethyloxycarbonyl group.

The "saturated heterocyclic group" according to the present specification may be a saturated heterocyclic group having heteroatoms selected from the group consisting of a nitrogen atom, an oxygen atom and a sulfur atom, and specific examples thereof include a morpholino group, a 1-pyrrolidinyl group, a piperidino group, a piperazinyl group, a 4-methyl-1-piperazinyl group, a tetrahydrofuranyl group, a tetrahydropyranyl group, a tetrahydrothiophenyl group, and a thiazolidinyl group, and an oxazolidinyl group.

In the present specification, the "unsaturated heterocyclic group" may include a monocyclic or polycyclic, fully unsaturated or partially unsaturated heterocyclic group having heteroatoms selected from the group consisting of a nitrogen atom, an oxygen atom and a sulfur atom, and specific examples thereof include an imidazolyl group, a thienyl group, a furyl group, a pyrrolyl group, an oxazolyl group, an isoxazolyl group, a thiazolyl group, an isothiazolyl group, a thiadiazolyl group, a pyrazolyl group, a triazolyl group, a tetrazolyl group, a pyridyl group, a pyrazyl group, a pyrimidinyl group, a pyridazinyl group, an indolyl group, an isoindolyl group, an indazolyl group, a triazolopyridyl group, a benzimidazolyl group, a benzoxazolyl group, a benzothiazolyl group, a benzothienyl group, a benzofuranyl group, a purinyl group, a quinolyl group, an isoquinolyl group, a quinazolinyl group, a quinoxalinyl group, a methylenedioxyphenyl group, an ethylenedioxyphenyl group, and a dihydrobenzofuranyl group.

The "aromatic hydrocarbon group" according to the present specification may include C6-C14 aromatic hydrocarbon groups such as a phenyl group, a tolyl group, a xylyl group, a naphthyl group, an anthracenyl group, a phenanthryl group, a fluorenyl group, and a tetrahydronaphthyl group.

The "saturated heterocyclic oxy group" according to the present specification is an oxy group to which a saturated heterocycle is bound, the heterocycle having a heteroatom selected from the group consisting of a nitrogen atom, an oxygen atom and a sulfur atom. Specific examples of the "saturated heterocyclic oxy group" include a morpholinyloxy group, a 1-pyrrolidinyloxy group, a piperidinoxy group, a piperazinyloxy group, a 4-methyl-1-piperazinyloxy group, a tetrahydrofuranyloxy group, a tetrahydropyranyloxy group, a tetrahydrothiophenyloxy group, a thiazolidinyloxy group, and an oxazolidinyloxy group.

Meanwhile, the expression "CA-CB" in the description on one or more substituents in the present specification indicates that the substituent is one or more substituents whose carbon number is A to B. For example, a "C1-C6 alkyl group" indicates an alkyl group having 1 to 6 carbon atoms, and a "C6-C14 aromatic hydrocarbon oxy group" indicates an oxy group to which an aromatic hydrocarbon group having 6 to 14 carbon atoms is bonded. The expression "A- to B-membered" indicates that the number of atoms that constitute a ring (number of ring members) is A to B. For example, a "4- to 10-membered saturated heterocyclic group" means a saturated heterocyclic group whose number of ring members is from 4 to 10.

In general formula (I), X represents a divalent heterocycloalkylene having 3 to 10 carbon atoms, which may have one or more substituents, contains at least one nitrogen atom in the ring, and contains 0 to 2 heteroatoms of the same kind or different kinds selected from the group consisting of an oxygen atom and a sulfur atom in the ring (nitrogen-containing C3-C10 heterocycloalkylene). Specific examples thereof include azetidinylene, pyrrolidinylene, piperidinylene, piperazinylene, morpholinylene, octahydroquinolinylene, and octahydroindolylene.

Preferably, X represents a heterocycloalkylene having 3 to 5 carbon atoms, which may have one or more substituents and contains one nitrogen atom in the ring (nitrogen-containing C3-C5 heterocycloalkylene), and X is more preferably azetidinylene, pyrrolidinylene, or piperidinylene, and even more preferably 1,3-azetidinylene, 1,3-pyrrolidinylene, or 1,3-piperidinylene.

Regarding the substituents on these heterocycloalkylenes, examples include substituents such as those described above; however, it is preferable that the heterocycloalkylenes be unsubstituted.

It is preferable that the nitrogen atom of a nitrogen-containing C3-C10 heterocycloalkylene group represented by X be bonded to the carbonyl group of —COY in general formula (I). Furthermore, it is preferable that the nitrogen atom of a nitrogen-containing C3-C5 heterocycloalkylene group represented by X be bonded to the carbonyl group of —COY in general formula (I).

In general formula (I), Y represents —C($R_4$)=C($R_5$)($R_6$) or —C≡C—$R_7$.

In general formula (I), W and Z each independently represent N or CH. Preferably, when Z is N, W is N, or when Z is CH, W is N or CH.

In general formula (I), n is preferably 0.

In general formula (I), regarding the "substituent(s)" for the "amino group which may have one or more substituents" represented by $R_1$, examples include substituents such as those described above; however, it is preferable that the amino group be unsubstituted.

The "amino group which may have one or more substituents" represented by $R_1$ is preferably an amino group.

In general formula (I), the "halogen atom" represented by $R_2$ or $R_3$ is preferably a fluorine atom, a chlorine atom, or a bromine atom.

In general formula (I), the "C1-C6 alkyl group" for the "C1-C6 alkyl group which may have one or more substituents" represented by $R_2$ or $R_3$ is preferably a C1-C4 alkyl group, and the C1-C6 alkyl group is more preferably a methyl group, an ethyl group, an n-propyl group, an isopropyl group, an n-butyl group, an isobutyl group, or a tert-butyl group, and even more preferably a methyl group or an ethyl group.

Regarding the "substituent(s)" for the "C1-C6 alkyl group which may have one or more substituents" represented by $R_2$ or $R_3$, it is preferable that the C1-C6 alkyl group be unsubstituted, or has one or more substituents such as a halogen atom or a C1-C4 alkoxy group. It is more preferable that the C1-C6 alkyl group be unsubstituted, or has one or more substituents such as a fluorine atom or a methoxy group. When the alkyl group has one or more substituents the number of substituents is not particularly limited; however, when the substituent is a halogen atom, the number of substituents is preferably from 1 to 3, while when the one or more substituents is a C1-C4 alkoxy group, the number of substituents is preferably 1.

The "C1-C6 alkyl group which may have one or more substituents" represented by $R_2$ or $R_3$ is preferably a C1-C6 alkyl group, a halogeno-C1-C6 alkyl group, or a C1-C4 alkoxy-substituted C1-C6 alkyl group; more preferably a C1-C4 alkyl group, a halogeno-C1-C4 alkyl group, or a C1-C4 alkoxy-substituted C1-C4 alkyl group; even more preferably a methyl group, an ethyl group, an n-propyl group, an isopropyl group, an n-butyl group, an isobutyl group, a tert-butyl group, a trifluoromethyl group, a trichloromethyl group, a methoxyethyl group, or an ethoxyethyl group; and still more preferably a methyl group, a trifluoromethyl group, or a methoxyethyl group.

In general formula (I), the "C1-C6 alkoxy group" for the "C1-C6 alkoxy group which may have one or more substituents" represented by $R_2$ or $R_3$ is preferably a "C1-C4 alkoxy group", and the "C1-C6 alkoxy group" is more preferably a methoxy group, an ethoxy group, an isopropoxy group, or an n-butoxy group, and even more preferably a methoxy group.

Regarding the "substituent(s)" for the "C1-C6 alkoxy group which may have one or more substituents" represented by $R_2$ or $R_3$, examples include substituents such as those described above; however, it is preferable that the C1-C6 alkoxy group be unsubstituted.

The "C1-C6 alkoxy group which may have one or more substituents" represented by $R_2$ or $R_3$ is preferably a C1-C6 alkoxy group; more preferably a C1-C4 alkoxy group; even more preferably a methoxy group, an ethoxy group, an isopropoxy group, or an n-butoxy group; and still more preferably a methoxy group.

In general formula (I), The "C3-C7 cycloalkyl group" for the "C3-C7 cycloalkyl group which may have one or more substituents" represented by $R_2$ or $R_3$ is preferably a C3-C6 cycloalkyl group, and more preferably a cyclopropyl group, a cyclobutyl group, a cyclopentyl group, or a cyclohexyl group.

Regarding the "substituent(s)" for the "C3-C7 cycloalkyl group which may have one or more substituents" represented by $R_2$ or $R_3$, examples include substituents such as those described above; however, it is preferable that the C3-C7 cycloalkyl group be unsubstituted.

The "C3-C7 cycloalkyl group which may have one or more substituents" represented by $R_2$ or $R_3$ is preferably a C3-C6 cycloalkyl group, and more preferably a cyclopropyl group, a cyclobutyl group, a cyclopentyl group, or a cyclohexyl group.

In general formula (I), the "C6-C14 aromatic hydrocarbon group" for the "C6-C14 aromatic hydrocarbon group which may have one or more substituents" represented by $R_2$ or $R_3$ is preferably a phenyl group or a naphthyl group, and more preferably a phenyl group.

Regarding the "substituent(s)" for the "C6-C14 aromatic hydrocarbon group which may have one or more substituents" represented by $R_2$ or $R_3$, it is preferable that the C6-C14 aromatic hydrocarbon group be unsubstituted, or has a halogen atom. It is more preferable that the C6-C14 aromatic hydrocarbon group be unsubstituted, or has a chlorine atom or a fluorine atom. When the C6-C14 aromatic hydrocarbon group has one or more substituents, the number of substituents is not particularly limited; however, the number of substituents is preferably from 1 to 3.

The "C6-C14 aromatic hydrocarbon group which may have one or more substituents" represented by $R_2$ or $R_3$ is preferably a phenyl group or a naphthyl group, which is unsubstituted or may have one or more substituents with a halogen atom, and is more preferably a phenyl group, a chlorophenyl group, a fluorophenyl group, a dichlorophenyl group, or a trichlorophenyl group; even more preferably a phenyl group or a chlorophenyl group; and particularly preferably a phenyl group or a 4-chlorophenyl group.

In general formula (I), the "4- to 10-membered monocyclic or polycyclic unsaturated heterocyclic group containing 1 to 3 heteroatoms of the same kind or different kinds selected from the group consisting of a nitrogen atom, an oxygen atom and a sulfur atom" for the "4- to 10-membered monocyclic or polycyclic unsaturated heterocyclic group containing 1 to 3 heteroatoms of the same kind or different kinds selected from the group consisting of a nitrogen atom, an oxygen atom and a sulfur atom, which heterocyclic group may have one or more substituents" represented by $R_2$ or $R_3$ is preferably a 4- to 6-membered monocyclic unsaturated heterocyclic group containing one nitrogen atom, oxygen atom or sulfur atom; more preferably a 4- to 6-membered monocyclic unsaturated heterocyclic group containing one sulfur atom; even more preferably a thienyl group; and still more preferably a 2-thienyl group.

Regarding the "substituent(s)" for the "4- to 10-membered monocyclic or polycyclic unsaturated heterocyclic group containing 1 to 3 heteroatoms of the same kind or different kinds selected from the group consisting of a nitrogen atom, an oxygen atom and a sulfur atom, which heterocyclic group may have one or more substituents" represented by $R_2$ or $R_3$, examples include substituents such as those described above; however, it is preferable that the unsaturated heterocyclic group is unsubstituted.

The "4- to 10-membered monocyclic or polycyclic unsaturated heterocyclic group containing 1 to 3 heteroatoms of the same kind or different kinds selected from the group consisting of a nitrogen atom, an oxygen atom and a sulfur atom, which heterocyclic group may have one or more substituents" represented by $R_2$ or $R_3$ is preferably a 4- to 6-membered monocyclic unsaturated heterocyclic group containing one nitrogen atom, oxygen atom or sulfur atom; more preferably a 4- to 6-membered monocyclic unsaturated heterocyclic group containing one sulfur atom; even more preferably a thienyl group; and still more preferably a 2-thienyl group.

In general formula (I), the "C1-C6 alkyl group" for the "C1-C6 alkyl group which may have one or more substituents" represented by $R_4$, $R_5$ or $R_6$ is preferably a C1-C4 alkyl group; more preferably a methyl group, an ethyl group, an n-propyl group, an isopropyl group, an n-butyl group, an isobutyl group, or a tert-butyl group; and even more preferably a methyl group.

Regarding the "substituent(s)" for the "C1-C6 alkyl group which may have one or more substituents" represented by $R_4$, $R_5$ or $R_6$, it is preferable that the C1-C6 alkyl group be unsubstituted, or has an amino group substituted with two C1-C4 alkyl groups (the C1-C4 alkyl groups may also form a heterocycloalkyl group having a 4- to 8-membered ring, together with the nitrogen atom to which these alkyl groups are bonded). It is more preferable that the C1-C6 alkyl group be unsubstituted, or has a dimethylamino group, a methylethylamino group, a diethylamino group, a methylisopropylamino group, a 1-piperidinyl group, or a 1-pyrrolidinyl group. When the "C1-C6 alkyl group which may have one or more substituents" has one or more substituents, the number of substituents is not particularly limited; however, the number of substituents is preferably 1.

The "C1-C6 alkyl group which may have one or more substituents" represented by $R_4$, $R_5$ or $R_6$ is preferably a C1-C4 alkyl group, or a C1-C4 alkyl group that is substituted with an amino group substituted with two C1-C4 alkyl groups (the C1-C4 alkyl groups may form a heterocycloalkyl group having a 4- to 8-membered ring, together with the nitrogen atom to which these alkyl groups are bonded). More preferred examples thereof include a methyl group, an ethyl group, an n-propyl group, an isopropyl group, an n-butyl group, a dimethylaminomethyl group, a methylethylaminomethyl group, a diethylaminomethyl group, a methylisopropylaminomethyl group, a dimethylaminoethyl group, a diethylaminoethyl group, a 1-piperidinylmethyl group, and a 1-pyrrolidinylmethyl group.

In general formula (I), the "C1-C6 alkyl group" for the "C1-C6 alkyl group which may have one or more substituents" represented by $R_7$ is preferably a C1-C4 alkyl group; more preferably a methyl group, an ethyl group, an n-propyl group, an isopropyl group, or an n-butyl group; and even more preferably a methyl group.

Regarding the "substituent(s)" for the "C1-C6 alkyl group which may have one or more substituents" represented by $R_7$, examples include substituents such as those described above; however, it is preferable that the C1-C6 alkyl group be unsubstituted.

The "C1-C6 alkyl group which may have one or more substituents" represented by $R_7$ is preferably a C1-C4 alkyl group; more preferably a methyl group, an ethyl group, an n-propyl group, an isopropyl group, or an n-butyl group; and even more preferably a methyl group.

In general formula (I), —C($R_4$)=C($R_5$)($R_6$) or —C≡C—$R_7$ represented by Y is particularly preferably any one selected from the group consisting of:

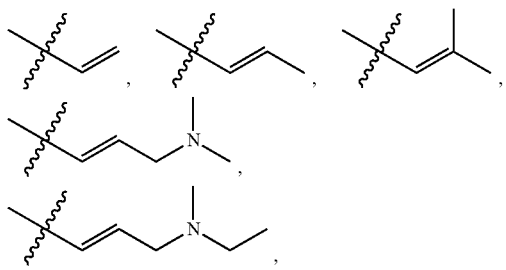

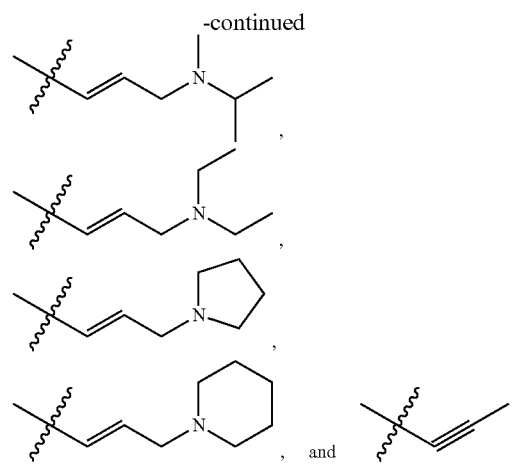

Regarding the compound of the present invention represented by general formula (I), preferred is a compound, or a salt thereof, in which:

X represents a nitrogen-containing C3-C10 heterocycloalkylene;

Y represents —C($R_4$)=C($R_5$)($R_6$) or —C≡C—$R_7$;

W and Z each independently represent N or CH;

n represents 0;

$R_1$ represents an amino group;

$R_2$ and $R_3$, which may be identical or different, each represent a hydrogen atom, a halogen atom, a C1-C6 alkyl group which may have one or more substituents, a C1-C6 alkoxy group which may have one or more substituents, a C3-C7 cycloalkyl group which may have one or more substituents, a C6-C14 aromatic hydrocarbon group which may have one or more substituents, a 4- to 10-membered, monocyclic or polycyclic unsaturated heterocyclic group containing 1 to 3 heteroatoms of the same kind or different kinds selected from the group consisting of a nitrogen atom, an oxygen atom and a sulfur atom, which heterocyclic group may have one or more substituents, or a cyano group; and $R_4$, $R_5$, $R_6$ and $R_7$, which may be identical or different, each represent a hydrogen atom, or a C1-C6 alkyl group which may have one or more substituents.

In this case, regarding the compound of the present invention represented by general formula (I), preferred is a compound, or a salt thereof, in which:

X represents a nitrogen-containing C3-C10 heterocycloalkylene (here, the nitrogen atom is bonded to the carbonyl group of —COY in the general formula (I));

Y represents —C($R_4$)=C($R_5$)($R_6$) or —C≡C—$R_7$;

W and Z each independently represent N or CH;

n represents 0;

$R_1$ represents an amino group;

$R_2$ and $R_3$, which may be identical or different, each represent a hydrogen atom, a halogen atom, a C1-C6 alkyl group which may have one or more substituents, a C1-C6 alkoxy group which may have one or more substituents, a C3-C7 cycloalkyl group which may have one or more substituents, a C6-C14 aromatic hydrocarbon group which may have one or more substituents, a 4- to 10-membered, monocyclic or polycyclic unsaturated heterocyclic group containing 1 to 3 heteroatoms of the same kind or different kinds selected from the group consisting of a nitrogen atom, an oxygen atom and a sulfur atom, which heterocyclic group may have one or more substituents, or a cyano group; and $R_4$, $R_5$, $R_6$ and $R_7$, which may be identical or different, each represent a hydrogen atom, or a C1-C6 alkyl group which may have one or more substituents.

Regarding the compound of the present invention represented by general formula (I), more preferred is a compound, or a salt thereof, in which:

X represents azetidinylene, pyrrolidinylene, or piperidinylene;

Y represents —C($R_4$)=C($R_5$)($R_6$) or —C≡C—$R_7$;

W and Z each independently represent N or CH;

n represents 0;

$R_1$ represents an amino group;

$R_2$ and $R_3$, which may be identical or different, each represent a hydrogen atom, a halogen atom, a C1-C6 alkyl group which may have one or more substituents, a C1-C6 alkoxy group which may have one or more substituents, a C3-C7 cycloalkyl group which may have one or more substituents, a C6-C14 aromatic hydrocarbon group which may have one or more substituents, a 4- to 10-membered, monocyclic or polycyclic unsaturated heterocyclic group containing 1 to 3 heteroatoms of the same kind or different kinds selected from the group consisting of a nitrogen atom, an oxygen atom and a sulfur atom, which heterocyclic group may have one or more substituents, or a cyano group; and $R_4$, $R_5$, $R_6$ and $R_7$, which may be identical or different, each represent a hydrogen atom, or a C1-C6 alkyl group which may have one or more substituents.

In this case, regarding the compound of the present invention represented by general formula (I), more preferred is a compound, or a salt thereof, in which:

X represents azetidinylene, pyrrolidinylene, or piperidinylene (here, the nitrogen atom is bonded to the carbonyl group of —COY in the general formula (I));

Y represents —C($R_4$)=C($R_5$)($R_6$) or —C≡C—$R_7$;

W and Z each independently represent N or CH;

n represents 0;

$R_1$ represents an amino group;

$R_2$ and $R_3$, which may be identical or different, each represent a hydrogen atom, a halogen atom, a C1-C6 alkyl group which may have one or more substituents, a C1-C6 alkoxy group which may have one or more substituents, a C3-C7 cycloalkyl group which may have one or more substituents, a C6-C14 aromatic hydrocarbon group which may have one or more substituents, a 4- to 10-membered, monocyclic or polycyclic unsaturated heterocyclic group containing 1 to 3 heteroatoms of the same kind or different kinds selected from the group consisting of a nitrogen atom, an oxygen atom and a sulfur atom, which heterocyclic group may have one or more substituents, or a cyano group; and $R_4$, $R_5$, $R_6$ and $R_7$, which may be identical or different, each represent a hydrogen atom, or a C1-C6 alkyl group which may have one or more substituents.

Regarding the compound of the present invention represented by general formula (I), more preferred is a compound, or a salt thereof, in which:

X represents azetidinylene, pyrrolidinylene, or piperidinylene;

Y represents —C($R_4$)=C($R_5$)($R_6$) or —C≡C—$R_7$;

W and Z independently represent N or CH;

n represents 0;

$R_1$ represents an amino group;

one of $R_2$ and $R_3$ represents a hydrogen atom or a C1-C6 alkyl group, and the other represents a hydrogen atom, a halogen atom, a C1-C6 alkyl group, a halogeno-C1-C6 alkyl group, a C1-C4 alkoxy-substituted C1-C6 alkyl group, a C1-C6 alkoxy group, a phenyl group which may have one or more substituents with a halogen atom, a 4- to 6-membered monocyclic unsaturated heterocyclic group containing one sulfur atom, or a cyano group; and when Y represents —C($R_4$)=C($R_5$)($R_6$), $R_4$, $R_5$ and $R_6$, which may be identical or different, each represent a hydrogen atom, a C1-C6 alkyl group, or a C1-C6 alkyl group that is substituted with an amino group substituted with two C1-C6 alkyl groups (the C1-C6 alkyl groups may form a heterocycloalkyl group having a 4- to 8-membered ring, together with the nitrogen atom to which these alkyl groups are bonded);

when Y represents —C≡C—$R_7$, $R_7$ represents a hydrogen atom or a C1-C6 alkyl group.

In this case, regarding the compound of the present invention represented by general formula (I), more preferred is a compound, or a salt thereof, in which:

X represents azetidinylene, pyrrolidinylene, or piperidinylene (here, the nitrogen atom is bonded to the carbonyl group of —COY in the general formula (I));

Y represents —C($R_4$)=C($R_5$)($R_6$) or —C≡C—$R_7$;

W and Z independently represent N or CH;

n represents 0;

$R_1$ represents an amino group;

one of $R_2$ and $R_3$ represents a hydrogen atom or a C1-C6 alkyl group, and the other represents a hydrogen atom, a halogen atom, a C1-C6 alkyl group, a halogeno-C1-C6 alkyl group, a C1-C4 alkoxy-substituted C1-C6 alkyl group, a C1-C6 alkoxy group, a phenyl group which may have one or more substituents with a halogen atom, a 4- to 6-membered monocyclic unsaturated heterocyclic group containing one sulfur atom, or a cyano group; and when Y represents —C($R_4$)=C($R_5$)($R_6$), $R_4$, $R_5$ and $R_6$, which may be identical or different, each represent a hydrogen atom, a C1-C6 alkyl group, or a C1-C6 alkyl group that is substituted with an amino group substituted with two C1-C6 alkyl groups (the C1-C6 alkyl groups may form a heterocycloalkyl group having a 4- to 8-membered ring, together with the nitrogen atom to which these alkyl groups are bonded);

when Y represents —C≡C—$R_7$, $R_7$ represents a hydrogen atom or a C1-C6 alkyl group.

Regarding the compound of the present invention represented by general formula (I), more preferred is a compound, or a salt thereof, in which:

X represents 1,3-azetidinylene, 1,3-pyrrolidinylene, or 1,3-piperidinylene;

Y represents —C($R_4$)=C($R_5$)($R_6$) or —C≡C—$R_7$;

when Z represents N, W represents N, and when Z represents CH, W represents N or CH;

n represents 0;

$R_1$ represents an amino group;

one of $R_2$ and $R_3$ represents a hydrogen atom or a C1-C4 alkyl group, and the other represents a hydrogen atom, a halogen atom, a C1-C4 alkyl group, a halogeno-C1-C4 alkyl group, a C1-C4 alkoxy-substituted C1-C4 alkyl group, a C1-C4 alkoxy group, a phenyl group which may have one or more substituents with a halogen atom, a 4- to 6-membered monocyclic unsaturated heterocyclic group containing one sulfur atom, or a cyano group; and when Y represents —C($R_4$)=C($R_5$)($R_6$), $R_4$, $R_5$ and $R_6$, which may be identical or different, each represent a hydrogen atom, a C1-C6 alkyl group, or a C1-C6 alkyl group that is substituted with an amino group substituted with two C1-C6 alkyl groups (the C1-C6 alkyl groups may form a heterocycloalkyl group having a 4- to 8-membered ring, together with the nitrogen atom to which these alkyl groups are bonded);

when Y represents —C≡C—$R_7$, $R_7$ represents a hydrogen atom or a C1-C4 alkyl group.

In this case, regarding the compound of the present invention represented by general formula (I), more preferred is a compound, or a salt thereof, in which:

X represents 1,3-azetidinylene, 1,3-pyrrolidinylene, or 1,3-piperidinylene (here, the nitrogen atom is bonded to the carbonyl group of —COY in the general formula (I));

Y represents —C($R_4$)=C($R_5$)($R_6$) or —C≡C—$R_7$;

when Z represents N, W represents N, and when Z represents CH, W represents N or CH;

n represents 0;

$R_1$ represents an amino group;

one of $R_2$ and $R_3$ represents a hydrogen atom or a C1-C4 alkyl group, and the other represents a hydrogen atom, a halogen atom, a C1-C4 alkyl group, a halogeno-C1-C4 alkyl group, a C1-C4 alkoxy-substituted C1-C4 alkyl group, a C1-C4 alkoxy group, a phenyl group which may have one or more substituents with a halogen atom, a 4- to 6-membered monocyclic unsaturated heterocyclic group containing one sulfur atom, or a cyano group; and when Y represents —C($R_4$)=C($R_5$)($R_6$), $R_4$, $R_5$ and $R_6$, which may be identical or different, each represent a hydrogen atom, a C1-C6 alkyl group, or a C1-C6 alkyl group that is substituted with an amino group substituted with two C1-C6 alkyl groups (the C1-C6 alkyl groups may form a heterocycloalkyl group having a 4- to 8-membered ring, together with the nitrogen atom to which these alkyl groups are bonded);

when Y represents —C≡C—$R_7$, $R_7$ represents a hydrogen atom or a C1-C4 alkyl group.

Regarding the compound of the present invention represented by general formula (I), more preferred is a compound, or a salt thereof, in which:

X represents 1,3-azetidinylene, 1,3-pyrrolidinylene, or 1,3-piperidinylene;

Y represents —C($R_4$)=C($R_5$)($R_6$) or —C≡C—$R_7$;

when Z represents N, W represents N, and when Z represents CH, W represents N or CH;

n represents 0;

$R_1$ represents an amino group;

one of $R_2$ and $R_3$ represents a hydrogen atom or a methyl group, and the other represents a hydrogen atom, a halogen atom, a methyl group, a trifluoromethyl group, a methoxyethyl group, a methoxy group, a phenyl group, a 4-chlorophenyl group, a 2-thienyl group, or a cyano group; and when Y represents —C($R_4$)=C($R_5$)($R_6$), $R_4$, $R_5$ and $R_6$, which may be identical or different, each represent a hydrogen atom, a methyl group, a dimethylaminomethyl group, a methylethylaminomethyl group, a diethylaminomethyl group, a methylisopropylaminomethyl group, a 1-piperidinylmethyl group, or a 1-pyrrolidinylmethyl group;

when Y represents —C≡C—$R_7$, $R_7$ represents a methyl group.

In this case, regarding the compound of the present invention represented by general formula (I), more preferred is a compound, or a salt thereof, in which:

X represents 1,3-azetidinylene, 1,3-pyrrolidinylene, or 1,3-piperidinylene (here, the nitrogen atom is bonded to the carbonyl group of —COY in the general formula (I));

Y represents —C($R_4$)=C($R_5$)($R_6$) or —C≡C—$R_7$;

when Z represents N, W represents N, and when Z represents CH, W represents N or CH;

n represents 0;

$R_1$ represents an amino group;

one of $R_2$ and $R_3$ represents a hydrogen atom or a methyl group, and the other represents a hydrogen atom, a halogen atom, a methyl group, a trifluoromethyl group, a methoxyethyl group, a methoxy group, a phenyl group, a 4-chlorophenyl group, a 2-thienyl group, or a cyano group; and when Y represents —C($R_4$)=C($R_5$)($R_6$), $R_4$, $R_5$ and $R_6$, which may be identical or different, each represent a hydrogen atom, a methyl group, a dimethylaminomethyl group, a methylethylaminomethyl group, a diethylaminomethyl group, a methylisopropylaminomethyl group, a 1-piperidinylmethyl group, or a 1-pyrrolidinylmethyl group;

when Y represents —C≡C—$R_7$, $R_7$ represents a methyl group.

Regarding the compound of the present invention represented by general formula (I), more preferred is a compound, or a salt thereof, in which:

(1) when Z represents N, and W represents N,

X represents 1,3-piperidinylene, and

Y represents a vinyl group;

(2) when Z represents CH, and W represents N,

X represents 1,3-pyrrolidinylene or 1,3-piperidinylene,

Y represents —C($R_4$)=C($R_5$)($R_6$) or —C≡C—($R_7$), and when Y represents —C($R_4$)=C($R_5$)($R_6$), $R_4$, $R_5$ and $R_6$, which may be identical or different, each represent a hydrogen atom, a methyl group, a dimethylaminomethyl group, a methylethylaminomethyl group, a diethylaminomethyl group, a methylisopropylaminomethyl group, a 1-piperidinylmethyl group, or a 1-pyrrolidinylmethyl group, when Y represents —C≡C—($R_7$), $R_7$ represents a methyl group; and (3) when Z represents CH, and W represents CH, X represents 1,3-azetidinylene or 1,3-pyrrolidinylene, Y represents —C($R_4$)=C($R_5$)($R_6$), and $R_4$, $R_5$ and $R_6$, which may be identical or different, each represent a hydrogen atom, a dimethylaminomethyl group, a methylethylaminomethyl group, a diethylaminomethyl group, a methylisopropylaminomethyl group, a 1-piperidinylmethyl group, or a 1-pyrrolidinylmethyl group;

n represents 0;

$R_1$ represents an amino group;

one of $R_2$ and $R_3$ represents a hydrogen atom or a methyl group, and the other represents a hydrogen atom, a halogen atom, a trifluoromethyl group, a methoxyethyl group, a phenyl group, a 2-thienyl group, or a cyano group.

In this case, regarding the compound of the present invention represented by general formula (I), more preferred is a compound, or a salt thereof, in which:

(1) when Z represents N, and W represents N,

X represents 1,3-piperidinylene (here, the nitrogen atom is bonded to the carbonyl group of —COY in the general formula (I)), and Y represents a vinyl group;

(2) when Z represents CH, and W represents N,

X represents 1,3-pyrrolidinylene or 1,3-piperidinylene (here, the nitrogen atom is bonded to the carbonyl group of —COY in the general formula (I)), Y represents —C($R_4$)=C($R_5$)($R_6$) or —C≡C—($R_7$), and when Y represents —C($R_4$)=C($R_5$)($R_6$), $R_4$, $R_5$ and $R_6$, which may be identical or different, each represent a hydrogen atom, a methyl group, a dimethylaminomethyl group, a methylethylaminomethyl group, a diethylaminomethyl group, a methylisopropylaminomethyl group, a 1-piperidinylmethyl group, or a 1-pyrrolidinylmethyl group, when Y represents —C≡C—($R_7$), R₇ represents a methyl group; and (3) when Z represents CH, and W represents CH, X represents 1,3-azetidinylene or 1,3-pyrrolidinylene (here, the nitrogen atom is bonded to the carbonyl group of —COY in the general formula (I)), Y represents —C(R₄)=C(R₅)(R₆), and R₄, R₅ and R₆, which may be identical or different, each represent a hydrogen atom, a dimethylaminomethyl group, a methylethylaminomethyl group, a diethylaminomethyl group, a methylisopropylaminomethyl group, a 1-piperidinylmethyl group, or a 1-pyrrolidinylmethyl group;

n represents 0;

R₁ represents an amino group;

one of R₂ and R₃ represents a hydrogen atom or a methyl group, and the other represents a hydrogen atom, a halogen atom, a trifluoromethyl group, a methoxyethyl group, a phenyl group, a 2-thienyl group, or a cyano group.

Regarding the compound of the present invention represented by general formula (I), more preferred is a compound, or a salt thereof, in which:

X represents 1,3-piperidinylene;
Y represents a vinyl group;
Z represents CH;
W represents N;
n represents 0;
R₁ represents an amino group;
any one of R₂ and R₃ represents a hydrogen atom, and the other represents a hydrogen atom, a halogen atom, or a cyano group.

In this case, regarding the compound of the present invention represented by general formula (I), more preferred is a compound, or a salt thereof, in which:

X represents 1,3-piperidinylene (here, the nitrogen atom is bonded to the carbonyl group of —COY in the general formula (I));
Y represents a vinyl group;
Z represents CH;
W represents N;
n represents 0;
R₁ represents an amino group;
one of R₂ and R₃ represents a hydrogen atom, and the other represents a hydrogen atom, a halogen atom, or a cyano group.

Regarding the compound of the present invention represented by general formula (I), particularly preferred is a compound, or a salt thereof, in which:

X represents 1,3-piperidinylene;
Y represents a vinyl group;
Z represents CH;
W represents N;
n represents 0;
R₁ represents an amino group;
one of R₂ and R₃ represents a hydrogen atom, and the other represents a hydrogen atom or a halogen atom.

In this case, regarding the compound of the present invention represented by general formula (I), particularly preferred is a compound, or a salt thereof, in which:

X represents 1,3-piperidinylene (here, the nitrogen atom is bonded to the carbonyl group of —COY in the general formula (I));
Y represents a vinyl group;
Z represents CH;
W represents N;
n represents 0;
R₁ represents an amino group;
one of R₂ and R₃ represents a hydrogen atom, and the other represents a hydrogen atom or a halogen atom.

Specific examples of the compound of the present invention include those compounds produced in the Examples described below; however, the compound is not intended to be limited to these.

Suitable examples of the compound of the present invention include the following compounds:

(1) (R)-1-(1-acryloylpiperidin-3-yl)-4-amino-N-(5-chlorobenzo[d]oxazol-2-yl)-1H-pyrazolo[3,4-d]pyrimidine-3-carboxamide (Example Compound 1)

(2) (R)-1-(1-acryloylpiperidin-3-yl)-4-amino-N-(5-bromobenzo[d]oxazol-2-yl)-1H-pyrazolo[3,4-d]pyrimidine-3-carboxamide (Example Compound 2)

(3) (R)-1-(1-acryloylpiperidin-3-yl)-4-amino-N-(5-(thiophen-2-yl)benzo[d]oxazol-2-yl)-1H-pyrazolo[3,4-d]pyrimidine-3-carboxamide (Example Compound 3)

(4) (R)-4-amino-N-(5-chlorobenzo[d]oxazol-2-yl)-1-(1-methacryloylpiperidin-3-yl)-1H-pyrazolo[3,4-d]pyrimidine-3-carboxamide (Example Compound 4)

(5) (R,E)-4-amino-N-(5-chlorobenzo[d]oxazol-2-yl)-1-(1-(but-2-enoyl)piperidin-3-yl)-1H-pyrazolo[3,4-d]pyrimidine-3-carboxamide (Example Compound 5)

(6) (R)-1-(1-acryloylpiperidin-3-yl)-4-amino-N-(5-cyanobenzo[d]oxazol-2-yl)-1H-pyrazolo[3,4-d]pyrimidine-3-carboxamide (Example Compound 6)

(7) (R)-1-(1-acryloylpiperidin-3-yl)-4-amino-N-(5-methoxybenzo[d]oxazol-2-yl)-1H-pyrazolo[3,4-d]pyrimidine-3-carboxamide (Example Compound 7)

(8) (R)-1-(1-acryloylpiperidin-3-yl)-4-amino-N-(5-(2-methoxyethyl)benzo[d]oxazol-2-yl)-1H-pyrazolo[3,4-d]pyrimidine-3-carboxamide (Example Compound 8)

(9) (R)-1-(1-acryloylpiperidin-3-yl)-4-amino-N-(oxazolo[4,5-b]pyridin-2-yl)-1H-pyrazolo[3,4-d]pyrimidine-3-carboxamide (Example Compound 9)

(10) (R)-1-(1-acryloylpiperidin-3-yl)-4-amino-N-(4-methylbenzo[d]oxazol-2-yl)-1H-pyrazolo[3,4-d]pyrimidine-3-carboxamide (Example Compound 10)

(11) (R)-4-amino-N-(5-fluorobenzo[d]oxazol-2-yl)-1-(1-methacryloylpiperidin-3-yl)-1H-pyrazolo[3,4-d]pyrimidine-3-carboxamide (Example Compound 11)

(12) (R)-1-(1-acryloylpiperidin-3-yl)-4-amino-N-(5-fluorobenzo[d]oxazol-2-yl)-1H-pyrazolo[3,4-d]pyrimidine-3-carboxamide (Example Compound 12)

(13) (R)-1-(1-acryloylpiperidin-3-yl)-4-amino-N-(benzo[d]oxazol-2-yl)-1H-pyrazolo[3,4-d]pyrimidine-3-carboxamide (Example Compound 13)

(14) (R,E)-4-amino-N-(benzo[d]oxazol-2-yl)-1-(1-(but-2-enoyl)piperidin-3-yl)-1H-pyrazolo[3,4-d]pyrimidine-3-carboxamide (Example Compound 14)

(15) (R,E)-4-amino-N-(5-chlorobenzo[d]oxazol-2-yl)-1-(1-(4-(dimethylamino)but-2-enoyl)piperidin-3-yl)-1H-pyrazolo[3,4-d]pyrimidine-3-carboxamide (Example Compound 15)

(16) (R,E)-4-amino-N-(5-chlorobenzo[d]oxazol-2-yl)-1-(1-(4-(ethyl(methyl)amino) but-2-enoyl)piperidin-3-yl)-1H-pyrazolo[3,4-d]pyrimidine-3-carboxamide (Example Compound 16)

(17) (R,E)-4-amino-N-(5-chlorobenzo[d]oxazol-2-yl)-1-(1-(4-(diethylamino)but-2-enoyl)piperidin-3-yl)-1H-pyrazolo[3,4-d]pyrimidine-3-carboxamide (Example Compound 17)

(18) (R,E)-4-amino-N-(5-chlorobenzo[d]oxazol-2-yl)-1-(1-(4-(isopropyl(methyl)amino)but-2-enoyl)piperidin-3-yl)-1H-pyrazolo[3,4-d]pyrimidine-3-carboxamide (Example Compound 18)

(19) (R,E)-4-amino-N-(5-chlorobenzo[d]oxazol-2-yl)-1-(1-(4-(pyrrolidin-1-yl)but-2-enoyl)piperidin-3-yl)-1H-pyrazolo[3,4-d]pyrimidine-3-carboxamide (Example Compound 19)

(20) (R,E)-4-amino-N-(5-chlorobenzo[d]oxazol-2-yl)-1-(1-(4-(piperidin-1-yl)but-2-enoyl)piperidin-3-yl)-1H-pyrazolo[3,4-d]pyrimidine-3-carboxamide (Example Compound 20)

(21) (R,E)-4-amino-N-(5-(thiophen-2-yl)benzo[d]oxazol-2-yl)-1-(1-(4-(dimethylamino)but-2-enoyl)piperidin-3-yl)-1H-pyrazolo[3,4-d]pyrimidine-3-carboxamide (Example Compound 21)

(22) (R)-4-amino-N-(benzo[d]oxazol-2-yl)-1-(1-(but-2-ynoyl)piperidin-3-yl)-1H-pyrazolo[3,4-d]pyrimidine-3-carboxamide (Example Compound 22)

(23) (R)-1-(1-acryloylpiperidin-3-yl)-4-amino-N-(5, 6-dimethylbenzo[d]oxazol-2-yl)-1H-pyrazolo[3,4-d]pyrimidine-3-carboxamide (Example Compound 23)

(24) (R)-1-(1-acryloylpyrrolidin-3-yl)-4-amino-N-(5-chlorobenzo[d]oxazol-2-yl)-1H-pyrazolo[3,4-d]pyrimidine-3-carboxamide (Example Compound 24)

(25) (R,E)-4-amino-N-(5-chlorobenzo[d]oxazol-2-yl)-1-(1-(but-2-enoyl)pyrrolidin-3-yl)-1H-pyrazolo[3,4-d]pyrimidine-3-carboxamide (Example Compound 25)

(26) (R,E)-4-amino-N-(5-chlorobenzo[d]oxazol-2-yl)-1-(1-(3-methylbut-2-enoyl)pyrrolidin-3-yl)-1H-pyrazolo[3,4-d]pyrimidine-3-carboxamide (Example Compound 26)

(27) (R)-1-(1-acryloylpyrrolidin-3-yl)-4-amino-N-(benzo[d]oxazol-2-yl)-1H-pyrazolo[3,4-d]pyrimidine-3-carboxamide (Example Compound 27)

(28) (R)-1-(1-acryloylpyrrolidin-3-yl)-4-amino-N-(5-(thiophen-2-yl)benzo[d]oxazol-2-yl)-1H-pyrazolo[3,4-d]pyrimidine-3-carboxamide (Example Compound 28)

(29) (R)-1-(1-acryloylpyrrolidin-3-yl)-4-amino-N-(5-methylbenzo[d]oxazol-2-yl)-1H-pyrazolo[3,4-d]pyrimidine-3-carboxamide (Example Compound 29)

(30) (R)-1-(1-acryloylpyrrolidin-3-yl)-4-amino-N-(5-fluorobenzo[d]oxazol-2-yl)-1H-pyrazolo[3,4-d]pyrimidine-3-carboxamide (Example Compound 30)

(31) (R)-1-(1-acryloylpyrrolidin-3-yl)-4-amino-N-(5-(4-chlorophenyl)benzo[d]oxazol-2-yl)-1H-pyrazolo[3,4-d]pyrimidine-3-carboxamide (Example Compound 31)

(32) (R,E)-4-amino-N-(5-chlorobenzo[d]oxazol-2-yl)-1-(1-(4-(dimethylamino)but-2-enoyl)pyrrolidin-3-yl)-1H-pyrazolo[3,4-d]pyrimidine-3-carboxamide (Example Compound 32)

(33) (R,E)-4-amino-N-(5-chlorobenzo[d]oxazol-2-yl)-1-(1-(4-(ethyl(methyl)amino)but-2-enoyl)pyrrolidin-3-yl)-1H-pyrazolo[3,4-d]pyrimidine-3-carboxamide (Example Compound 33)

(34) (R,E)-4-amino-N-(5-chlorobenzo[d]oxazol-2-yl)-1-(1-(4-(diethylamino)but-2-enoyl)piperidin-3-yl)-1H-pyrazolo[3,4-d]pyrimidine-3-carboxamide (Example Compound 34)

(35) (R,E)-4-amino-N-(5-chlorobenzo[d]oxazol-2-yl)-1-(1-(4-(isopropyl(methyl)amino)but-2-enoyl)pyrrolidin-3-yl)-1H-pyrazolo[3, 4-d]pyrimidine-3-carboxamide (Example Compound 35)

(36) (R,E)-4-amino-N-(5-chlorobenzo[d]oxazol-2-yl)-1-(1-(4-(pyrrolidin-1-yl)but-2-enoyl)pyrrolidin-3-yl)-1H-pyrazolo[3,4-d]pyrimidine-3-carboxamide (Example Compound 36)

(37) (R,E)-4-amino-N-(5-chlorobenzo[d]oxazol-2-yl)-1-(1-(4-(piperidin-1-yl)but-2-enoyl)pyrrolidin-3-yl)-1H-pyrazolo[3,4-d]pyrimidine-3-carboxamide (Example Compound 37)

(38) (R)-1-(1-acryloylpyrrolidin-3-yl)-4-amino-N-(5-methoxybenzo[d]oxazol-2-yl)-1H-pyrazolo[3,4-d]pyrimidine-3-carboxamide (Example Compound 38)

(39) (R)-1-(1-acryloylpyrrolidin-3-yl)-4-amino-N-(5-cyanobenzo[d]oxazol-2-yl)-1H-pyrazolo[3,4-d]pyrimidine-3-carboxamide (Example Compound 39)

(40) (R)-1-(1-acryloylpyrrolidin-3-yl)-4-amino-N-(5-(2-methoxyethyl)benzo[d]oxazol-2-yl)-1H-pyrazolo[3,4-d]pyrimidine-3-carboxamide (Example Compound 40)

(41) (R)-1-(1-acryloylpyrrolidin-3-yl)-4-amino-N-(5-phenylbenzo[d]oxazol-2-yl)-1H-pyrazolo[3,4-d]pyrimidine-3-carboxamide (Example Compound 41)

(42) (R,E)-4-amino-N-(5-phenylbenzo[d]oxazol-2-yl)-1-(1-(4-(dimethylamino)but-2-enoyl)pyrrolidin-3-yl)-1H-pyrazolo[3,4-d]pyrimidine-3-carboxamide (Example Compound 42)

(43) (R)-1-(1-acryloylpyrrolidin-3-yl)-4-amino-N-(5-(trifluoromethyl)benzo[d]oxazol-2-yl)-1H-pyrazolo[3,4-d]pyrimidine-3-carboxamide (Example Compound 43)

(44) (R,E)-4-amino-N-(5-(trifluoromethyl)benzo[d]oxazol-2-yl)-1-(1-(4-(dimethylamino)but-2-enoyl)pyrrolidin-3-yl)-1H-pyrazolo[3,4-d]pyrimidine-3-carboxamide (Example Compound 44)

(45) 1-(1-Acryloylazetidin-3-yl)-4-amino-N-(5-chlorobenzo[d]oxazol-2-yl)-1H-pyrazolo[3,4-d]pyrimidine-3-carboxamide (Example Compound 45)

(46) 7-(1-Acryloylazetidin-3-yl)-4-amino-N-(5-chlorobenzo[d]oxazol-2-yl)-7H-pyrrolo[2,3-d]pyrimidine-5-carboxamide (Example Compound 46)

(47) (E)-4-amino-N-(5-chlorobenzo[d]oxazol-2-yl)-7-(1-(4-(dimethylamino)but-2-enoyl) azetidin-3-yl) 7H-pyrrolo[2, 3-d]pyrimidine-5-carboxamide (Example Compound 47)

(48) (R)-7-(1-acryloylpyrrolidin-3-yl)-4-amino-N-(5-chlorobenzo[d]oxazol-2-yl)-7H-pyrrolo[2,3-d]pyrimidine-5-carboxamide (Example Compound 48)

(49) (R,E)-4-amino-N-(5-chlorobenzo[d]oxazol-2-yl)-7-(1-(4-(dimethylamino)but-2-enoyl)pyrrolidin-3-yl) 7H-pyrrolo[2,3-d]pyrimidine-5-carboxamide (Example Compound 49)

(50) (R,E)-4-amino-N-(5-chlorobenzo[d]oxazol-2-yl)-7-(1-(4-(ethyl(methyl)amino)but-2-enoyl)pyrrolidin-3-yl) 7H-pyrrolo[2,3-d]pyrimidine-5-carboxamide (Example Compound 50)

(51) (R,E)-4-amino-N-(5-chlorobenzo[d]oxazol-2-yl)-7-(1-(4-(diethylamino)but-2-enoyl)pyrrolidin-3-yl) 7H-pyrrolo[2,3-d]pyrimidine-5-carboxamide (Example Compound 51)

(52) (R,E)-4-amino-N-(5-chlorobenzo[d]oxazol-2-yl)-7-(1-(4-(isopropyl(methyl)amino)but-2-enoyl)pyrrolidin-3-yl) 7H-pyrrolo[2,3-d]pyrimidine-5-carboxamide (Example Compound 52)

(53) (R,E)-4-amino-N-(5-chlorobenzo[d]oxazol-2-yl)-7-(1-(4-(pyrrolidin-1-yl)but-2-enoyl)pyrrolidin-3-yl) 7H-pyrrolo[2,3-d]pyrimidine-5-carboxamide (Example Compound 53)

(54) (R,E)-4-amino-N-(5-chlorobenzo[d]oxazol-2-yl)-7-(1-(4-(piperidin-1-yl)but-2-enoyl)pyrrolidin-3-yl) 7H-pyrrolo[2,3-d]pyrimidine-5-carboxamide (Example Compound 54)

(55) (R)-7-(1-acryloylpyrrolidin-3-yl)-4-amino-N-(5-phenylbenzo[d]oxazol-2-yl)-7H-pyrrolo[2,3-d]pyrimidine-5-carboxamide (Example Compound 55)

(56) (R,E)-4-amino-N-(5-phenylbenzo[d]oxazol-2-yl)-7-(1-(4-(dimethylamino)but-2-enoyl)pyrrolidin-3-yl) 7H-pyrrolo[2,3-d]pyrimidine-5-carboxamide (Example Compound 56)

(57) (R,E)-4-amino-N-(5-phenylbenzo[d]oxazol-2-yl)-7-(1-(4-(ethyl(methyl)amino)but-2-enoyl)pyrrolidin-3-yl) 7H-pyrrolo[2,3-d]pyrimidine-5-carboxamide (Example Compound 57)

(58) (R,E)-4-amino-N-(5-phenylbenzo[d]oxazol-2-yl)-7-(1-(4-(diethylamino)but-2-enoyl)pyrrolidin-3-yl) 7H-pyrrolo[2,3-d]pyrimidine-5-carboxamide (Example Compound 58)

(59) (R,E)-4-amino-N-(5-phenylbenzo[d]oxazol-2-yl)-7-(1-(4-(isopropyl(methyl)amino)but-2-enoyl)pyrrolidin-3-yl) 7H-pyrrolo[2, 3-d]pyrimidine-5-carboxamide (Example Compound 59)

(60) (R,E)-4-amino-N-(5-phenylbenzo[d]oxazol-2-yl)-7-(1-(4-(pyrrolidin-1-yl)but-2-enoyl)pyrrolidin-3-yl) 7H-pyrrolo[2,3-d]pyrimidine-5-carboxamide (Example Compound 60)

(61) (R,E)-4-amino-N-(5-phenylbenzo[d]oxazol-2-yl)-7-(1-(4-(piperidin-1-yl)but-2-enoyl)pyrrolidin-3-yl) 7H-pyrrolo[2,3-d]pyrimidine-5-carboxamide (Example Compound 61)

Next, a method for producing the compound related to the present invention is explained.

Compound (I) of the present invention can be produced by, for example, the production method described below or by the method disclosed in Examples. However, the method for producing compound (I) of the present invention is not intended to be limited to these reaction examples.

Production Method 1

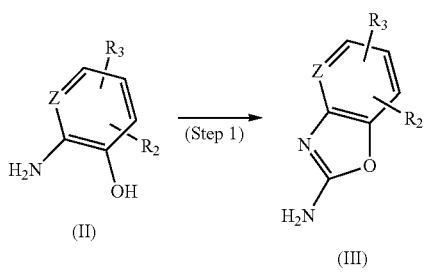

where Z, $R_2$ and $R_3$ respectively have the same meanings as defined above.

(Step 1) This step is a process for synthesizing a benzoxazole compound represented by general formula (III) from an aminophenol represented by general formula (II). The compound represented by general formula (II) may be a commercially available product, or can be produced according to a known method.

Examples of the reagent used include cyano compounds such as bromocyan, chlorocyan, iodocyan, and 1,1-carbonimidoylbis-1H-imidazole. The reaction is carried out by using from 0.5 to 5 moles, and preferably from 0.9 to 1.5 moles, of the cyano compound with respect to 1 mole of the compound represented by general formula (II). Meanwhile, regarding the relevant cyano compound, a commercially available product can be used, or the cyano compound can be produced according to a known method. The solvent used in the reaction may be any solvent as long as it does not adversely affect the reaction, and for example, alcohols (for example, methanol and ethanol), hydrocarbons (for example, benzene, toluene, and xylene), halogenated hydrocarbons (for example, methylene chloride, chloroform, and 1,2-dichloroethane), nitriles (for example, acetonitrile), ethers (for example, dimethoxyethane and tetrahydrofuran), aprotic polar solvents (for example, N,N-dimethylformamide, dimethyl sulfoxide, and hexamethylphosphoramide), water, or mixtures thereof are used. The reaction time may be from 0.1 to 100 hours, and preferably from 0.5 to 24 hours. The reaction temperature may be from 0° C. to 120° C., and preferably from 0° C. to 90° C.

The compound represented by general formula (III) that is obtainable as such is isolated and purified by known separation and purification means, for example, concentration, concentration under reduced pressure, crystallization, solvent extraction, reprecipitation, and chromatography, or can be subjected to the subsequent step without being isolated and purified.

Production Method 2

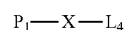
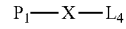
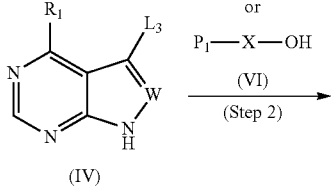

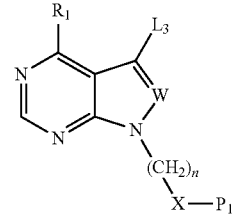

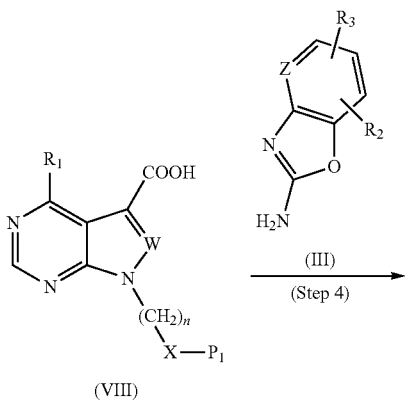
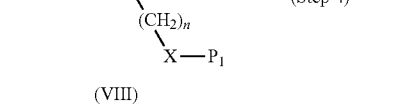

-continued

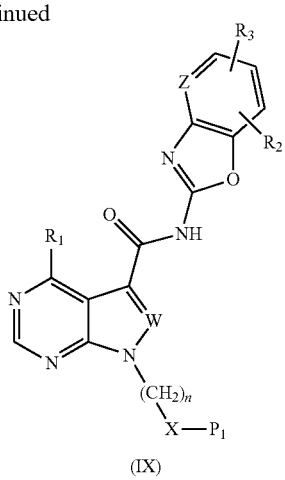

(IX)

where $L_3$ and $L_4$ each represent a leaving group; $P_1$ represents a protective group of the amino group contained in X; and W, X, Y, Z, $R_1$, $R_2$, $R_3$ and n respectively have the same meanings as defined above.

(Step 2) This step is a process for producing a compound represented by general formula (VII), by using a compound represented by general formula (IV) and a compound represented by general formula (V) or general formula (VI). The compound represented by general formula (IV) may be a commercially available product, or can be produced according to a known method.

When the compound represented by general formula (V) is used as an alkylation reagent, the compound represented by general formula (VII) can be produced in the presence of a base. In general formula (V), $L_4$ represents a leaving group, for example, a chlorine atom, a bromine atom, an iodine atom, a methanesulfonic acid ester, or a p-toluenesulfonic acid ester, and a commercially available product may be used, or the compound can be produced according to a known method. The compound represented by general formula (V) can be used in an amount of 1 to 10 moles, and preferably from 1 to 5 moles, with respect to 1 mole of the compound represented by general formula (IV).

Examples of the base include inorganic bases such as sodium hydrogen carbonate, sodium carbonate, potassium carbonate, cesium carbonate, cesium hydroxide, sodium hydride, and potassium hydride; and organic amines such as trimethylamine, triethylamine, tripropylamine, diisopropylethylamine, N-methylmorpholine, pyridine, 4-(N,N-dimethylamino)pyridine, lutidine, and collidine. Regarding the amount of use of the base, the base can be used in an amount of 1 to 100 moles, and preferably from 2 to 10 moles, with respect to 1 mole of the compound represented by general formula (IV).

For the solvent, for example, N,N-dimethylformamide, N,N-dimethylacetamide, dimethyl sulfoxide, tetrahydrofuran, 1,4-dioxane, N-methylpyrrolidin-2-one, and acetonitrile can be used singly or as mixtures. The reaction time may be from 0.1 to 100 hours, and preferably from 0.5 to 24 hours. The reaction temperature may be from 0° C. to a temperature at which the solvent boils, and preferably from 0° C. to 100° C.

When the compound of general formula (VI) is used as an alkylation reagent, the compound represented by general formula (VII) can be produced by using the Mitsunobu reaction. Usually, the present process can be carried out according to a known method (for example, Chemical Reviews, Vol. 109, p. 2551, 2009), and for example, the process can be carried out in the presence of a Mitsunobu reagent and a phosphine reagent, in a solvent which does not adversely affect the reaction. The present process is usually carried out by using the compound represented by general formula (VI) in an amount of from 1 to 10 moles, and preferably from 1 to 5 moles, with respect to 1 mole of the compound represented by general formula (IV).

Examples of the Mitsunobu reagent include diethyl azodicarboxylate and diisopropyl azodicarboxylate. Regarding the amount used as the Mitsunobu reagent, the process is carried out by using the reagent in an amount of from 1 to 10 moles, and preferably from 1 to 5 moles, with respect to 1 mole of the compound represented by general formula (IV).

Examples of the phosphine reagent include triphenylphosphine and tributylphosphine. Regarding the phosphine reagent, the process is carried out by using the reagent in an amount of from 1 to 10 moles, and preferably from 1 to 5 moles, with respect to 1 mole of the compound represented by general formula (IV).

The reaction solvent is not particularly limited as long as the reaction solvent does not interrupt the reaction; however, for example, toluene, benzene tetrahydrofuran, 1,4-dioxane, dimethylformamide, dimethylacetamide, N-methylpyrrolidinone, dimethyl sulfoxide, or mixed solvents thereof are suitable.

The reaction temperature may be usually from −78° C. to 200° C., and preferably from 0° C. to 50° C. The reaction time may be usually from 5 minutes to 3 days, and preferably from 10 minutes to 10 hours.

The compound represented by general formula (VII) that is obtainable as such is isolated and purified by known separation and purification means, for example, concentration, concentration under reduced pressure, crystallization, solvent extraction, reprecipitation, and chromatography, or is subjected to the subsequent process without being isolated and purified.

(Step 3) This step is a process for producing a compound represented by general formula (VIII) by allowing the compound represented by general formula (VII) to react with, for example, a transition metal and optionally a base, under a carbon monoxide atmosphere in the presence of an alcohol, in a solvent which does not adversely affect the reaction.

In general formula (VII), the leaving group represented by $L_3$ is a bromine atom or an iodine atom, and regarding the relevant compound, a commercially available product may be used, or the compound can be produced according to a known method.

In the present process, the pressure of carbon monoxide may be usually from 1 to 10 atmospheres, and preferably from 1 to 5 atmospheres. Regarding the amount of use of the alcohol compound, the compound can be used in an amount of from 1 to 10 moles, and preferably from 1 to 5 moles, with respect to 1 mole of the compound represented by general formula (VII). Examples of the alcohol compound include methanol, ethanol, propanol, isopropyl alcohol, diethylaminoethanol, isobutanol, 4-(2-hydroxyethyl)morpholine, 3-morpholinopropanol, and diethylaminopropanol.

The transition metal catalyst that can be used in the present process is, for example, a palladium catalyst (for example, palladium acetate, tris(dibenzylideneacetone)dipalladium, bis(triphenylphosphine)palladium(II) dichloride, or 1,1'-bis(diphenylphosphino)ferrocene-palladium(II) dichloride-dichloromethane complex), and if necessary, a ligand (for example, triphenylphosphine, xantphos, or tritert-butylphosphine) is added thereto. The amount of use of the transition metal catalyst may vary depending on the kind of the catalyst; however, the amount of use may be usually from 0.0001 to 1 mole, and preferably from 0.001 to 0.5 moles, with respect to 1 mole of the compound represented by general formula (VII). The amount of use of the ligand may be usually from 0.0001 to 4 moles, and preferably from 0.01 to 2 moles, with respect to 1 mole of the compound represented by general formula (VII).

Furthermore, a base can be added to the reaction, as necessary. Examples of the base include organic bases such as triethylamine, diisopropylethylamine, pyridine, lutidine, collidine, 4-dimethylaminopyridine, N-methylmorpholine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases such as sodium hydrogen carbonate, sodium carbonate, potassium carbonate, cesium carbonate, sodium hydroxide, and sodium hydride. The amount of use of the base may be usually from 0.1 to 50 moles, and preferably from 1 to 20 moles, with respect to 1 mole of the compound represented by general formula (VII).

The reaction solvent is not particularly limited as long as the reaction solvent does not interrupt the reaction, and examples thereof include hydrocarbons (for example, benzene, toluene, and xylene), nitriles (for example, acetonitrile), ethers (for example, dimethoxyethane, tetrahydrofuran, and 1,4-dioxane), alcohols (for example, methanol and ethanol), aprotic polar solvents (for example, dimethylformamide, dimethylacetamide, N-methylpyrrolidinone, dimethyl sulfoxide, and hexamethylphosphoramide), water, or mixtures thereof. The reaction time may be from 0.1 to 100 hours, and preferably from 0.5 to 24 hours. The reaction temperature may be from 0° C. to a temperature at which the solvent boils, and preferably from 0° C. to 150° C.

After this reaction, since a mixture of the carboxylic acid compound (VIII) and an ester form corresponding to the alcohol used is obtained, a hydrolysis reaction is conducted in order to converge the mixture into the compound represented by general formula (VIII). Hydrolysis is carried out by using a base, and examples thereof include organic bases such as diethylamine, diisopropylamine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases such as sodium hydrogen carbonate, sodium carbonate, potassium carbonate, cesium carbonate, and sodium hydroxide.

The reaction solvent is not particularly limited as long as the reaction solvent does not interrupt the reaction, and examples thereof include hydrocarbons (for example, benzene, toluene, and xylene), nitriles (for example, acetonitrile), ethers (for example, dimethoxyethane, tetrahydrofuran, and 1,4-dioxane), alcohols (for example, methanol and ethanol), aprotic polar solvents (for example, dimethylformamide, dimethylacetamide, N-methylpyrrolidinone, dimethyl sulfoxide, and hexamethylphosphoramide), water, or mixtures thereof. The reaction time may be from 0.1 to 100 hours, and preferably from 0.5 to 24 hours. The reaction temperature may be from 0° C. to a temperature at which the solvent boils, and preferably from 0° C. to 150° C.

The compound represented by general formula (VIII) that is obtainable as such is isolated and purified by known separation and purification means, for example, concentration, concentration under reduced pressure, crystallization, solvent extraction, reprecipitation, and chromatography, or is subjected to the subsequent process without being isolated and purified.

(Step 4) This step is a process for producing a compound represented by general formula (IX) by performing an amidation reaction by using compounds represented by general formula (VIII) and general formula (III).

The process may be carried out by using the compound of general formula (III) in an amount of from 0.5 to 10 moles, and preferably from 1 to 3 moles, with respect to 1 mole of the compound represented by general formula (VIII), in the presence of an appropriate condensing agent or an activating agent as an amidation reagent.

The reaction solvent is not particularly limited as long as the reaction solvent does not interrupt the reaction, and for example, isopropanol, tert-butyl alcohol, toluene, benzene, methylene chloride, chloroform, tetrahydrofuran, 1,4-dioxane, dimethylformamide, dimethylacetamide, N-methylpyrrolidinone, dimethyl sulfoxide, or mixed solvents thereof are suitable. The reaction temperature may be usually from −78° C. to 200° C., and preferably from 0° C. to 50° C. The reaction time may be usually from 5 minutes to 3 days, and preferably from 5 minutes to 10 hours.

Examples of the condensing agent and activating agent include diphenylphosphoric acid azide, N,N'-dicyclohexylcarbodiimide, benzotriazol-1-yloxytrisdimethylaminophosphonium salt, 4-(4,6-dimethoxy-1,3,5-triazin-2-yl)-4-methylmorpholinium chloride, 1-ethyl-3-(3-dimethylaminopropyl)carbodiimide, a combination of 1-ethyl-3-(3-dimethylaminopropyl)carbodiimide and 1-hydroxybenzotriazole, 2-chloro-1,3-dimethylimidazolinium chloride, O-(7-azabenzotriazo-1-yl)-N,N,N',N'-tetramethylhexauronium hexafluorophosphate, 1,1-carbonyldiimidazole, and N-hydroxysuccinic acid imide.

Furthermore, regarding the reaction described above, a base may be added thereto, if necessary. Examples of the base include organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, diazabicycloundecene, diazabicyclononene, and butyllithium; and inorganic bases such as sodium hydrogen carbonate, sodium carbonate, potassium carbonate, cesium carbonate, sodium hydroxide, and sodium hydride. The amount of addition thereof may be from 1 to 100 moles, and preferably from 1 to 10 moles, with respect to 1 mole of the compound represented by general formula (VIII).

The compound represented by general formula (IX) that is obtainable as such is isolated and purified by known separation and purification means, for example, concentration, concentration under reduced pressure, crystallization, solvent extraction, reprecipitation, and chromatography, or can be used in the production of the compound (I) of the present invention without being isolated and purified.

Production Method 3

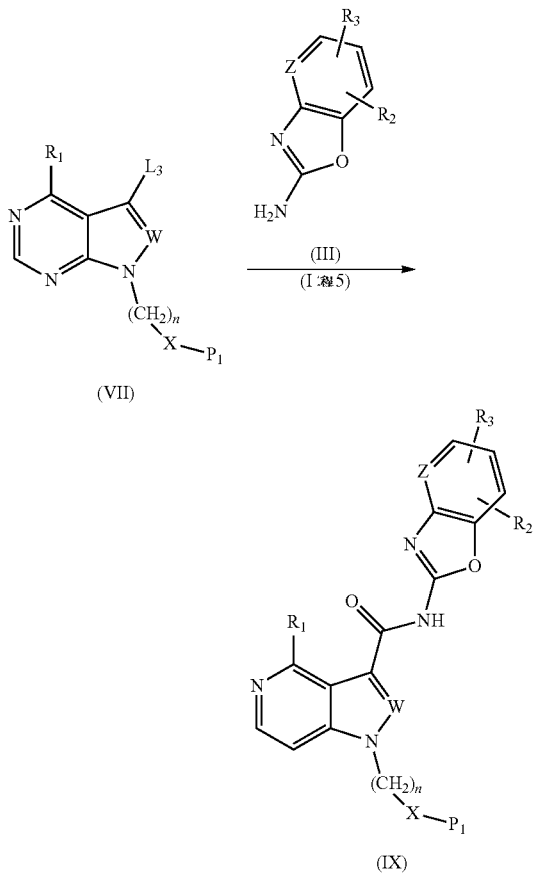

(Step 5)
where L₃ represents a leaving group; and W, X, Y, Z, P₁, R₁, R₂, R₃ and n respective have the same meanings as defined above.

(Step 5) This step is a process for producing a compound represented by general formula (IX) by allowing the compound represented by general formula (VII) to react with, for example, a transition metal and optionally a base, under a carbon monoxide atmosphere in the presence of the compound (III), in a solvent which does not adversely affect the reaction.

In general formula (VII), the leaving group represented by L₃ is a bromine atom or an iodine atom, and a commercially available product may be used, or the relevant compound can be produced according to a known method.

In the present process, the pressure of carbon monoxide may be from 1 to 10 atmospheres, and preferably from 1 to 5 atmospheres.

The transition metal catalyst that can be used in the present process is, for example, a palladium catalyst (for example, palladium acetate, tris(dibenzylideneacetone)dipalladium, bis(triphenylphosphine)palladium(II) dichloride, and 1,1'-bis(diphenylphosphino)ferrocene-palladium(II) dichloride-dichloromethane complex, and if necessary, a ligand (for example, triphenylphosphine, xantphos, or tri-tert-butylphosphine) is added thereto. The amount of use of the transition metal catalyst may vary with the kind of the catalyst; however, the amount of use may be usually from 0.0001 to 1 mole, and preferably from 0.001 to 0.5 moles, with respect to 1 mole of the compound represented by general formula (IX). The amount of use of the ligand may be usually from 0.0001 to 4 moles, and preferably from 0.01 to 2 moles, with respect to 1 mole of the compound represented by general formula (VII).

Furthermore, regarding the reaction described above, a base may be added thereto, if necessary. Examples of the base include organic bases such as triethylamine, diisopropylethylamine, pyridine, lutidine, collidine, 4-dimethylaminopyridine, N-methylmorpholine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases such as sodium hydrogen carbonate, sodium carbonate, potassium carbonate, cesium carbonate, sodium hydroxide, and sodium hydride. The amount of use of the base is usually from 0.1 to 50 moles, and preferably from 1 to 20 moles, with respect to 1 mole of the compound represented by general formula (VII).

The reaction solvent is not particularly limited as long as the reaction solvent does not interrupt the reaction, and examples thereof include hydrocarbons (for example, benzene, toluene, and xylene), nitriles (for example, acetonitrile), ethers (for example, dimethoxyethane, tetrahydrofuran, and 1,4-dioxane), alcohols (for example, methanol and ethanol), aprotic polar solvents (for example, dimethylformamide, dimethylacetamide, N-methylpyrrolidinone, dimethyl sulfoxide, and hexamethylphosphoramide), water, or mixtures thereof. The reaction time may be from 0.1 to 100 hours, and preferably from 0.5 to 24 hours. The reaction temperature may be from 0° C. to a temperature at which the solvent boils, and preferably from 0° C. to 15° C.

The compound represented by general formula (IX) that is obtainable as such is isolated and purified by known separation and purification means, for example, concentration, concentration under reduced pressure, crystallization, solvent extraction, reprecipitation, and chromatography, or can be used in the production of the compound (I) of the present invention without being isolated and purified.

Production Method 4

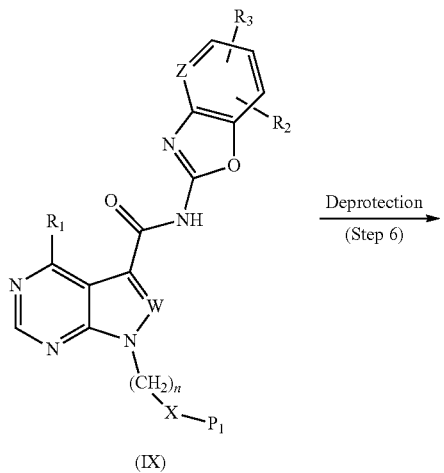

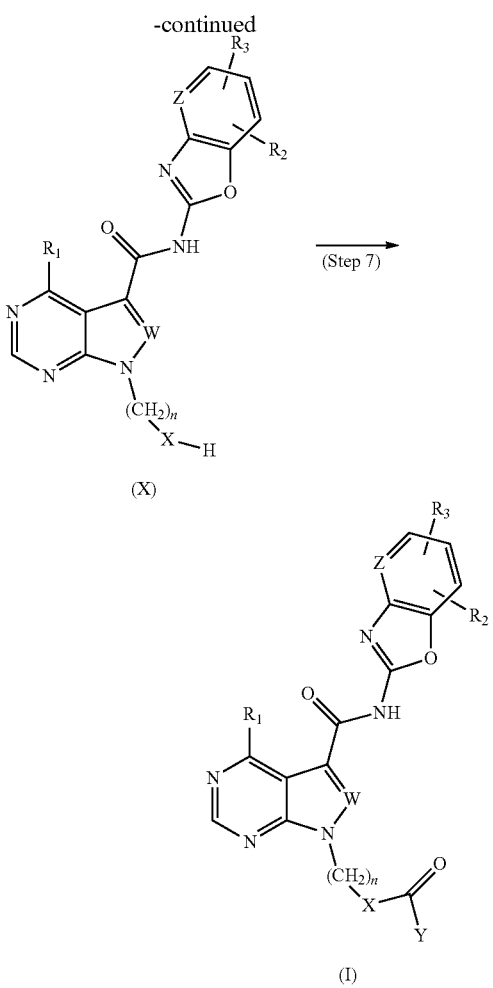

where $P_1$, W, X, Y, Z, $R_1$, $R_2$, $R_3$ and n respectively have the same meanings as defined above.

(Step 6) This step is a process for producing a compound represented by general formula (X) by deprotecting the amino group protection of the compound represented by general formula (IX). The method for deprotection can be carried out usually by a known method, for example, the method described in Protective Groups in Organic Synthesis, T.W. Greene, John Wiley & sons (1981), or a method equivalent thereto. An example of the protective group is tert-butyloxycarbonyl. When a tert-butyloxycarbonyl group is used as the protective group, deprotection under acidic conditions is preferred, and examples of the acid include hydrochloric acid, acetic acid, trifluoroacetic acid, sulfuric acid, methanesulfonic acid, and tosylic acid. Alternatively, deprotection with a Lewis acid is also preferred, and examples thereof include trimethylsilyliodine and a boron trifluoride-diethyl ether complex. The amount of use of the acid may be preferably from 1 to 100 moles with respect to 1 mole of the compound (IX).

The solvent used in the reaction may be any solvent as long as it does not adversely affect the reaction, and for example, alcohols (for example, methanol), hydrocarbons (for example, benzene, toluene, and xylene), halogenated hydrocarbons (for example, methylene chloride, chloroform, and 1,2-dichloroethane), nitriles (for example, acetonitrile), ethers (for example, dimethoxyethane and tetrahydrofuran), aprotic polar solvents (for example, N,N-dimethylformamide, dimethyl sulfoxide, and hexamethylphosphoramide), or mixtures thereof are used. The reaction time may be from 0.1 to 100 hours, and preferably from 0.5 to 24 hours. The reaction temperature may be from 0° C. to 120° C., and preferably from 0° C. to 90° C.

The compound represented by general formula (X) that is obtainable as such is isolated and purified by known separation and purification means, for example, concentration, concentration under reduced pressure, crystallization, solvent extraction, reprecipitation, and chromatography, or may be subjected to the subsequent process without being isolated and purified.

(Step 7) This step is a process for producing the compound of the present invention represented by general formula (I), by an amidation reaction between the compound represented by general formula (X) and a carboxylic acid represented by Y—COOH or an acid halide represented by Y—C(=O)-L (where L represents a chlorine atom or a bromine atom).

When a carboxylic acid represented by Y—COOH is used as an amidation reagent, the amidation reaction is carried out by using from 0.5 to 10 moles, and preferably from 1 to 3 moles, of the carboxylic acid with respect to 1 mole of the compound represented by general formula (X), in the presence of an appropriate condensing agent. Meanwhile, regarding the relevant carboxylic acid, a commercially available product may be used, or the carboxylic acid can be produced according to a known method.

The reaction solvent is not particularly limited as long as the reaction solvent does not interrupt the reaction, and for example, isopropanol, tert-butyl alcohol, toluene, benzene, methylene chloride, chloroform, tetrahydrofuran, 1,4-dioxane, dimethylformamide, dimethylacetamide, N-methylpyrrolidinone, dimethyl sulfoxide, or mixed solvents thereof are suitable. The reaction temperature is usually from −78° C. to 200° C., and preferably from 0° C. to 50° C. The reaction time is usually from 5 minutes to 3 days, and preferably from 5 minutes to 10 hours.

Examples of the condensing agent include diphenylphosphoric acid azide, N,N'-dicyclohexylcarbodiimide, benzotriazol-1-yloxytrisdimethylaminophosphonium salt, 4-(4,6-dimethoxy-1,3,5-triazin-2-yl)-4-methylmorpholinium chloride, 1-ethyl-3-(3-dimethylaminopropyl)carbodiimide, a combination of 1-ethyl-3-(3-dimethylaminopropyl)carbodiimide and 1-hydroxybenzotriazole, 2-chloro-1,3-dimethylimidazolinium chloride, and O-(7-azabenzotriazo-1-yl)-N,N,N',N'-tetramethylhexauronium hexafluorophosphate.

Furthermore, regarding the reaction, a base can be added thereto, if necessary. Examples of the base include organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases such as sodium hydrogen carbonate, sodium carbonate, potassium carbonate, cesium carbonate, sodium hydroxide, and sodium hydride. The amount of addition thereof may be from 1 to 100 moles, and preferably from 1 to 10 moles, with respect to 1 mole of the compound represented by general formula (X).

When an acid halide represented by Y—C(=O)-L (where L represents a chlorine atom or a bromine atom) is used as the amidation reagent, the reaction is carried out by using from 0.5 to 5 moles, and preferably from 0.9 to 1.1 moles, of the acid halide with respect to 1 mole of the compound represented by general formula (X). Meanwhile, regarding the relevant acid halide, a commercially available product may be used, or the acid halide can be produced according to a known method.

The reaction solvent is not particularly limited as long as the reaction solvent does not interrupt the reaction, and for example, water, toluene, benzene, methylene chloride, chloroform, tetrahydrofuran, acetonitrile, 1,4-dioxane, dimethylformamide, dimethylacetamide, N-methylpyrrolidinone, or mixed solvents thereof are suitable. The reaction temperature may be usually from −78° C. to 200° C., and preferably from −20° C. to 50° C. The reaction time may be usually from 5 minutes to 3 days, and preferably from 5 minutes to 10 hours.

Furthermore, regarding the reaction described above, a base can be added thereto, if necessary. Examples of the base include organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases such as sodium hydrogen carbonate, sodium carbonate, potassium carbonate, cesium carbonate, sodium hydroxide, and sodium hydride. Regarding the amount of addition, the base can be used in an amount of from 1 to 100 moles, and preferably from 1 to 10 moles, with respect to 1 mole of the compound represented by general formula (X).

The compound represented by general formula (I) that is obtainable as such can be isolated and purified by known separation and purification means, for example, concentration, concentration under reduced pressure, crystallization, solvent extraction, reprecipitation, and chromatography.

Production Method 5

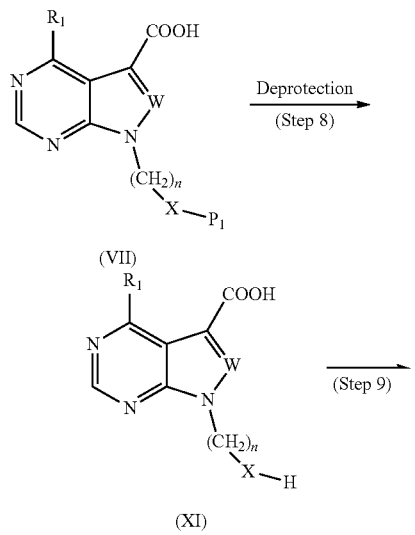

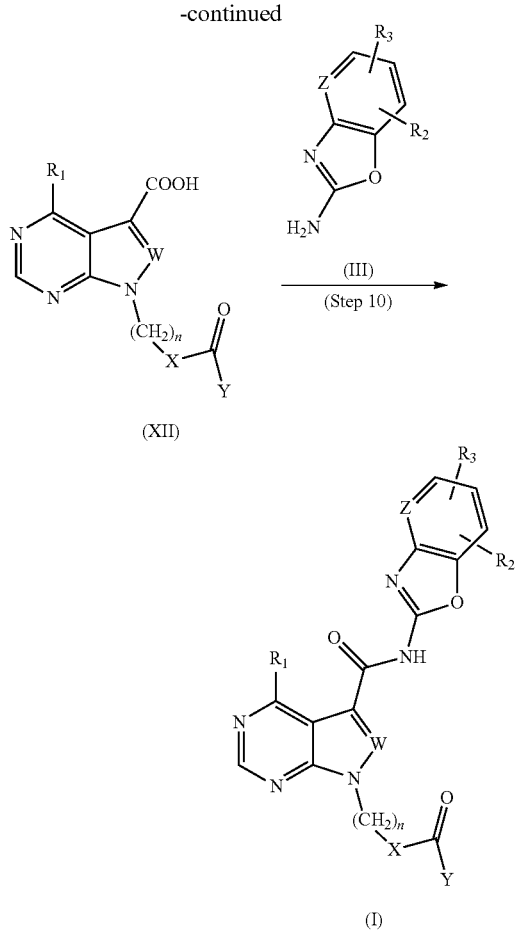

where $P_1$, W, X, Y, Z, $R_1$, $R_2$, $R_3$ and n respectively have the same meanings as defined above.

(Step 8 and Step 9)

These steps are processes for producing a compound represented by general formula (XII) by subjecting the compound represented by general formula (VIII) to procedures similar to Production Method 4, Steps 6 and 7.

(Step 10)

This step is a process for producing the compound represented by general formula (I) by subjecting the compound represented by general formula (XII) to procedures similar to Production Method 2, Step 4.

The compound represented by general formula (I) that is obtainable as such can be isolated and purified by known separation and purification means, for example, concentration, concentration under reduced pressure, crystallization, solvent extraction, reprecipitation, and chromatography.

Regarding the Production Methods 1 to 5, for an amino group, an imino group, a hydroxyl group, a carboxyl group, a carbonyl group, an amide group, and a functional group having an active proton, such as indole, a protected reagent may be used in appropriate steps in the various production methods, or a protective group may be introduced to the relevant functional group according to a conventional method, and then the protective group may be removed.

The "protective group for an amino group or an imino group" is not particularly limited as long as the group has its function, and examples thereof include, for example, aralkyl groups such as a benzyl group, a p-methoxybenzyl group, a 3,4-dimethoxybenzyl group, an o-nitrobenzyl group, a p-nitrobenzyl group, a benzhydryl group, a trityl group, and a coumyl group; for example, lower alkanoyl groups such as a formyl group, an acetyl group, a propionyl group, a butyryl group, a pivaloyl group, a trifuloroacetyl group, and a trichloroacetyl group; for example, a benzoyl group; for example, arylalkanoyl groups such as a phenylacetyl group and a phenoxyacetyl group; for example, lower alkoxycarbonyl groups such as a methoxycarbonyl group, an ethoxycarbonyl group, a propyloxycarbonyl group, and a tert-butoxycarbonyl group; for example, aralkyloxycarbonyl groups such as a p-nitrobenzyloxycarbonyl group and a phenethyloxycarbonyl group; for example, lower alkylsilyl groups such as a trimethylsilyl group and a tert-butyldimethylsilyl group; for example, a tetrahydropyranyl group; for example, a trimethylsilylethoxymethyl group; for example, lower alkylsulfonyl groups such as a methylsulfonyl group, an ethylsulfonyl group, and a tert-butylsulfonyl group; for example, lower alkylsulfinyl groups such as a tert-butylsulfinyl group; for example, arylsulfonyl groups such as a benzenesulfonyl group and a toluensulfonyl group; and for example, imide groups such as a phthalimide group. Particularly, a trifluoroacetyl group, an acetyl group, a tert-butoxycarbonyl group, a benzyloxycarbonyl group, a trimethylsilylethoxymethyl group, and a coumyl group are preferred.

The "protective group for a hydroxyl group" is not particularly limited as long as the protective group has its function, and examples thereof include lower alkyl groups such as a methyl group, an ethyl group, a propyl group, an isopropyl group, and a tert-butyl group; for example, lower alkylsilyl groups such as a trimethylsilyl group and a tert-butyldimethylsilyl group; for example, lower alkoxymethyl groups such as a methoxymethyl group and a 2-methoxyethoxymethyl group; for example, a tetrahydropyranyl group; for example, a trimethylsilylethoxymethyl group; for example, aralkyl groups such as a benzyl group, a p-methoxybenzyl group, a 2,3-dimethoxybenzyl group, an o-nitrobenzyl group, a p-nitrobezyl group, and a trityl group; and for example, acyl groups such as a formyl group, an acetyl group, and a trifluoroacetyl group. Particularly, for example, a methyl group, a methoxymethyl group, a tetrahydropyranyl group, a trimethylsilylethoxymethyl group, a tert-butyldimethylsilyl group, and an acetyl group are preferred.

The "protective group for a carboxyl group" is not particularly limited as long as the protective group has its function, and examples thereof include lower alkyl groups such as a methyl group, an ethyl group, a propyl group, an isopropyl group, and a tert-butyl group; for example, halo-lower alkyl groups such as a 2,2,2-trichloroethyl group; for example, lower alkenyl groups such as an allyl group; for example, a trimethylsilylethoxymethyl group; and for example, aralkyl groups such as a benzyl group, a p-methoxybenzyl group, a p-nitrobenzyl group, a benzhydryl group, and a trityl group. Particularly, for example, a methyl group, an ethyl group, a tert-butyl group, an allyl group, a benzyl group, a p-methoxybenzyl group, and a trimethylsilylethoxymethyl group are preferred.

The "protective group for a carbonyl group" is not particularly limited as long as the protective group has its function, and examples thereof include ketals and acetals such as ethylene ketal, trimethylene ketal, dimethyl ketal, ethylene acetal, trimethylene acetal, and dimethyl accetal.

The "protective group for an amino group or a functional group having an active proton, such as indole" is not particularly limited as long as the group has its function, and examples thereof include, lower alkyl groups such as a methyl group, an ethyl group, a propyl group, an isopropyl group, and a tert-butyl group; for example, lower alkylsilyl groups such as a trimethylsilyl group and a tert-butyldimethylsilyl group; for example, lower alkoxymethyl groups such as a methoxymethyl group and a 2-methoxyethoxymethyl group; for example, a tetrahydropyranyl group; for example, a trimethylsilylethoxymethyl group; for example, aralkyl groups such as a benzyl group, a p-methoxybenzyl group, a 2,3-dimethoxybenzyl group, an o-nitrobenzyl group, a p-nitrobezyl group, and a trityl group; and for example, acyl groups such as a formyl group, an acetyl group, and a trifluoroacetyl group. Particularly, a methyl group, a methoxymethyl group, a tetrahydropyranyl group, a trimethylsilylethoxymethyl group, a tert-butyldimethylsilyl group, and an acetyl group are preferred.

The method for removing a protective group may vary depending on the kind of the relevant protective group and stability of the target compound. However, for example, the removal of a protective group is carried out according to methods described in the Literature (see Protective Groups in Organic Synthesis, $3^{rd}$ Ed., written by T.W. Greene, John Wiley & Sons, 1999) or methods equivalent thereto, for example, by a method of performing solvolysis with an acid or a base, that is, for example, bringing 0.01 mol to a large excess of an acid, preferably trifluoroacetic acid, formic acid or hydrochloric acid; or an equal mol to a large excess of a base, preferably potassium hydroxide or calcium hydroxide, into effect; or by chemical reduction with, for example, a metal hydride complex, or by catalytic reduction with, for example, a palladium-carbon catalyst or a Raney nickel catalyst.

The compound of the present invention can be easily isolated and purified by conventional separation means. Examples of such means include solvent extraction, recrystallization, reverse phase high performance liquid chromatography for fractionation, column chromatography, and thin layer chromatography for fractionation.

When the compound of the present invention has isomers such as optical isomers, stereoisomers, regioisomers and rotamers, mixtures of any isomers are all included in the compound of the present invention. For example, when the compound of the present invention has optical isomers, optical isomers resolved from racemates are also included in the compound of the present invention. These isomers can be each obtained as single compounds by synthesis techniques that are known per se and separation techniques (for example, concentration, solvent extraction, column chromatography, and recrystallization).

The compound of the present invention or a salt thereof may be crystalline, and irrespective of whether the crystal form is a single form or a polymorphic mixture, the crystals are also included in the compound of the present or a salt thereof. A crystal can be produced by applying a crystallization method that is known per se, and performing crystallization. The compound of the present invention or a salt thereof may be a solvate (for example, hydrate) or may be a non-solvate, which are both included in the compound of the present invention or a salt thereof. Compounds labeled with isotopes (for example, $^3$H, $^{14}$C, $^{35}$S, and $^{125}$I) are also included in the compound of the present invention or a salt thereof.

A prodrug of the compound of the present invention or a salt thereof refers to a compound which converts to the compound of the present invention or a salt thereof as a result of a reaction caused by an enzyme or gastric acid in the living body under physiological conditions, that is, a compound which enzymatically causes, for example, oxidation, reduction or hydrolysis and converts to the compound of the present invention or a salt thereof, or a compound which causes, for example, hydrolysis by means of gastric acid and converts to the compound of the present invention or a salt thereof. Furthermore, the prodrug of the compound of the present invention or a salt thereof may also be a compound which converts to the compound of the present invention or a salt thereof under the physiological conditions described in Hirokawa Shoten Annual of 1990 "Iyakuhin no Kaihatsu (Development of Pharmaceutical Products)", Vol. 7, Molecule Design, pp. 163-198.

A salt of the compound of the present invention means a salt that is conventionally used in the field of organic chemistry, and examples thereof include salts such as a base addition salt associated with a carboxyl group when the compound of the present invention has the relevant carboxyl group; and an acid addition salt associated with an amino group or a basic heterocyclic group when the compound of the present invention has the relevant amino group or basic heterocyclic group.

Examples of the base addition salt include, for example, alkali metal salts such as sodium salt and potassium salt; for example, alkaline earth metal salts such as calcium salt and magnesium salt; for example, ammonium salt; and for example, organic amine salts such as trimethylamine salt, triethylamine salt, dicyclohexylamine salt, ethanolamine salt, diethanolamine salt, triethanolamine salt, procaine salt, and N,N'-dibenzylethylenediamine salt.

Examples of the acid addition salt include, for example, inorganic acid salts such as hydrochloride, sulfate, nitrate, phosphate, and perchlorate; for example, organic acid salts such as acetate, formate, maleate, fumarate, tartrate, citrate, ascorbate, and trifluoroacetate; and for example, sulfonic acid salts such as methanesulfonate, isetionate, benzenesulfonate, and p-toluenesulfonate.

The compound of the present invention or a salt thereof has an excellent BTK inhibitory activity, and is useful as a preventive and/or therapeutic agent of various immune diseases, for example, as a preventive and/or therapeutic agent of allergic diseases, autoimmune diseases, or inflammatory diseases, particularly as a preventive and/or therapeutic agent of allergic diseases or autoimmune diseases. Furthermore, the compound or a salt thereof has an excellent selectivity to BTK, and has an advantage of having reduced adverse effects that are caused by inhibiting other kinases (for example, EGFR) as well.

"BTK" according to the present specification includes human or non-human mammalian BTK's, and the BTK is preferably human BTK. Also, the term "BTK" includes isoforms.

Furthermore, due to its excellent BTK inhibitory activity, the compound of the present invention or a salt thereof is useful as a medical drug for prevention or treatment of immune diseases associated with BTK, for example, allergic diseases, autoimmune diseases, or inflammatory diseases, particularly allergic diseases or autoimmune diseases.

The "diseases associated with BTK" include diseases that undergo a decrease in the incidence rate and remission, alleviation and/or complete recovery of symptoms, as a result of deletion, suppression and/or inhibition of the functions of BTK.

The object immune diseases are not particularly limited as long as they are immune diseases caused by an abnormality in expression and/or activity of BTK, and examples thereof include, for example, allergic diseases, autoimmune diseases, and inflammatory diseases.

Conventional medical drugs for rheumatoid arthritis (for example, Tofacitnib that is a pan-JAK inhibitor) reduce the number of NK cells, which lowers immunocompetence of a host, and therefore, have been pointed out to have a problem of high risk of infection with herpesvirus or carcinogenesis (ACR HOTILINE, Dec. 14, 2012).

The compound of the present invention or a salt thereof has a low suppressing ability to NK cell or the like due to its high cell selectivity, and accordingly, has an advantage of having a high safety, with a low risk of suppressing host immune.

Furthermore, the compound of the present invention or a salt thereof is also useful in a morbid state associated with osteoclasts (for example, osteoporosis), since it suppresses bone resorption in mouse osteoclasts and restore bone density.

The object allergic diseases are not particularly limited, and examples thereof include, for example, bronchial asthma, allergic rhinitis, pollinosis, atopic dermatitis, food allergy, anaphylaxis, drug allergy, hives, and conjunctivitis. Preferred examples include bronchial asthma, allergic rhinitis, pollinosis, and atopic dermatitis, and particularly preferred examples include allergic rhinitis, pollinosis, and atopic dermatitis.

The object autoimmune diseases are not particularly limited, and examples thereof include rheumatoid arthritis, systemic lupus erythematosus, dermatosclerosis, polymyositis, Sjögren's syndrome, and Behcet's disease. Preferred examples include rheumatoid arthritis and systemic lupus erythematosus, and particularly preferred examples include rheumatoid arthritis.

The object inflammatory diseases are not particularly limited, and examples thereof include appendicitis, blepharitis, bronchiolitis, bronchitis, bursitis, cervicitis, cholangitis, cholecystitis, ulcerative colitis, Crohn's disease, irritable bowel syndrome, cystitis, dacryoadenitis, contact dermatitis, dermatomyositis, cerebritis, endocarditis, endometritis, epididymitis, fasciitis, fibrositis, gastroenteritis, hepatitis, sudoriferous abscess, laryngitis, mastitis, meningitis, myelitis, myocarditis, nephritis, ovaritis, didymitis, pancreatitis, parotitis, pericarditis, peritonitis, pharyngitis, pleuritis, phlebitis, pneumonia, rectitis, prostatitis, pyelonephritis, salpingitis, nasosinusitis, stomatitis, osteoarthritis, synovitis, tendinitis, tonsillitis, uveitis, vaginitis, vasculitis, and vulvitis. Preferred examples include ulcerative colitis, Crohn's disease, irritable bowel syndrome, contact dermatitis, cystitis, and osteoarthritis. Particularly preferred examples include contact dermatitis, cystitis, and osteoarthritis.

As for the object immune diseases, preferred examples include allergic diseases and autoimmune diseases, with more preferred examples including atopic dermatitis, rheumatoid arthritis, systemic lupus erythematosus, allergic rhinitis, and pollinosis, and the most preferred examples including rheumatoid arthritis.

In using the compound of the present invention or a salt thereof as a medical drug, various dosage forms can be employed according to the purpose of prevention or treatment by incorporating pharmaceutical carriers as necessary. The dosage form may be, for example, any of an oral preparation, an injectable preparation, a suppository preparation, an ointment, and a patch. These dosage forms can be respectively produced by formulation methods that are conventionally used and known to those skilled in the art.

Regarding the pharmaceutical carriers, various organic or inorganic carrier materials that are conventionally used as formulation materials are used, and the pharmaceutical carriers are incorporated as, for example, an excipient, a binder, a disintegrant, a lubricant, and a coating agent in solid preparations; and as a solvent, a dissolution aid, a suspending agent, an isotonic agent, a pH adjusting agent, a buffering agent, and an analgesic agent in liquid preparations. Furthermore, if necessary, formulation additives such as an antiseptic, an antioxidant, a colorant, a flavoring/savoring agent, and a stabilizer can also be used.

Examples of the excipient include lactose, sucrose, D-mannitol, starch, crystalline cellulose, and calcium silicate.

Examples of the binder include hydroxypropyl cellulose, methyl cellulose, polyvinylpyrrolidone, sugar powder, and hypromellose.

Examples of the disintegrant include sodium starch glycolate, carmellose calcium, croscarmellose sodium, crospovidone, low-substituted hydroxypropyl cellulose, and partially gelatinized starch.

Examples of the lubricant include talc, magnesium stearate, sucrose fatty acid esters, stearic acid, and sodium stearyl fumarate.

Examples of the coating agent include ethyl cellulose, aminoalkyl methacrylate copolymer RS, hypromellose, and sucrose.

Examples of the solvent include water, propylene glycol, and physiological saline.

Examples of the dissolution aid include polyethylene glycol, ethanol, α-cyclodextrin, Macrogol 400, and Polysorbate 80.

Examples of the suspending agent include carrageenan, crystalline cellulose, carmellose sodium, and polyoxyethylene hardened castor oil.

Examples of the isotonic agent include sodium chloride, glycerin, and potassium chloride.

Examples of the pH adjusting agent and the buffering agent include sodium citrate, hydrochloric acid, lactic acid, phosphoric acid, and sodium dihydrogen phosphate.

Examples of the analgesic agent include procaine hydrochloride and lidocaine.

Examples of the antiseptic agent include ethyl paraoxybenzoate, cresol, and benzalkonium chloride.

Examples of the antioxidant include sodium sulfite, ascorbic acid, and natural vitamin E.

Examples of the colorant include titanium oxide, iron sesquioxide, Edible Blue No. 1, and copper chlorophyll.

Examples of the flavoring/savoring agent include aspartame, saccharin, sucralose, 1-menthol, and mint flavor.

Examples of the stabilizer include sodium pyrosulfite, sodium edetate, erythorbic acid, magnesium oxide, and dibutylhydroxytoluene.

In the case of preparing an oral solid preparation, an excipient, optionally an excipient, a binder, a disintegrant, a lubricant, a colorant, and a flavoring/savoring agent are added to the compound of the present invention, and then for example, a tablet, a coated tablet, a granular preparation, a powder preparation, and a capsule preparation can be produced by conventional methods.

In the case of preparing an injectable preparation, a pH adjusting agent, a buffering agent, a stabilizer, an isotonic agent, and a local anesthetic are added to the compound of the present invention, and a subcutaneous, intramuscular, and intravenous injectable preparations can be produced by conventional methods.

The amounts of the compound of the present invention to be incorporated into the various unit dosage forms may vary depending on the symptoms of the patient to whom this compound should be applied, or depending on the formulation form; however, it is generally desirable to adjust the amount to from 0.05 to 1,000 mg in an oral preparation, to from 0.01 to 500 mg in an injectable preparation, and to from 1 to 1,000 mg in a suppository preparation, per unit dosage form.

Furthermore, the daily dose of a medicament having the dosage form described above may vary with for example, the symptoms, body weight, age and gender of the patient, and cannot be determined indiscriminately. However, the dose may be used usually in an amount of from 0.05 to 5,000 mg, and preferably from 0.1 to 1,000 mg, per day for an adult (body weight: 50 kg), and it is preferable to administer this once a day, or in divided portions in about from 2 to 3 times.

EXAMPLES

Hereinafter, the present invention will be described more specifically by way of Examples, but the present invention is not intended to be limited to these.

Regarding the various reagents used in the Examples, unless particularly stated otherwise, commercially available products were used. For silica gel column chromatography, PURIF-PACK (registered trademark) SI manufactured by Schott Moritex Corp., KP-Sil (registered trademark) Silica Prepacked Column manufactured by Biotage AB, or HP-Sil (registered trademark) Silica Prepacked Column manufactured by Biotage AB was used. For basic silica gel column chromatography, PURIF-PACK (registered trademark) NH manufactured by Moritex Corp., or KP-NH (registered trademark) Prepacked Column manufactured by Biotage AB was used. For thin layer chromatography for fractionation, KIESELGEL TM60F254, Art. 5744 manufactured by Merck KGaA, or NH2 silica gel 60F254 plate manufactured by Wako Pure Chemical Industries, Ltd. was used. The NMR spectrum was measured with an AL400 (400 MHz; JEOL, Ltd.), a MERCURY400 (400 MHz; Agilent Technologies, Inc.) type spectrometer, or an INOVA400 (400 MHz; Agilent Technologies, Inc.) equipped with an OMNMR probe (Protasis Corp.) type spectrometer, and with tetramethylsilane as the internal reference when the deuterated solvent contains tetramethylsilane, while in other cases, by using an NMR solvent as the internal reference. All the δ values were expressed in ppm. The microwave reaction was carried out by using a DISCOVER S class manufactured by CEM Corp.

The LCMS spectrum was measured with an ACQUITY SQD (quadrupole type) manufactured by Waters Corp. under the conditions described below.

Column: YMC-TRIART C18 manufactured by YMC Co., Ltd., 2.0×50 mm, 1.9 μm
MS detection: ESI positive
UV detection: 254 nm and 210 nm
Column flow rate: 0.5 mL/min
Mobile phase: Water/acetonitrile (0.1% formic acid)
Amount of injection: 1 μL
Gradient (Table 1)

TABLE 1

| Time (min) | Water | Acetonitrile |
|---|---|---|
| 0 | 95 | 5 |
| 0.1 | 95 | 5 |
| 2.1 | 5 | 95 |
| 3.0 | STOP | |

Furthermore, reverse phase preparative HPLC purification was carried out with a preparative system manufactured by Waters Corp. under the conditions described below.

Column: A YMC-ACTUS TRIART C18 manufactured by YMC Co., Ltd., 20×50 mm, 5 μm, connected with a YMC-ACTUS TRIART C18 manufactured by YMC Co., Ltd. 20×10 mm, 5 μm, was used.

UV detection: 254 nm
MS detection: ESI positive
Column flow rate: 25 mL/min
Mobile phase: Water/acetonitrile (0.1% formic acid)
Amount of injection: 0.1 to 0.5 mL
The meanings of abbreviations are shown below.
s: Singlet
d: Doublet
t: Triplet
q: Quartet
dd: Double doublet
dt: double triplet
td: Triple doublet
tt: Triple triplet
ddd: Double double doublet
ddt: Double double triplet
dtd: Double triple doublet
tdd: Triplet double doublet
m: Multiplet
br: Broad
brs: Broad singlet
CDI: Carbonyldiimidazole
DMSO-$d_6$: Deuterated dimethyl sulfoxide
$CDCl_3$: Deuterated chloroform
$CD_3OD$: Deuterated methanol
THF: Tetrahydrofuran
DMF: N, N-dimethylformamide
DMA: N,N-dimethylacetamide
NMP: 1-Methyl-2-pyrrolidinone
DMSO: Dimethyl sulfoxide
TFA: Trifluoroacetic acid
WSC: 1-(3-Dimethylaminopropyl)-3-ethylcarbodiimide hydrochloride
HOBt: 1-Hydroxybenzotriazole monohydrate
HATU: (Dimethylamino)-N,N-dimethyl(3H-[1,2,3]triazolo[4,5-b]pyridin-3-yloxy)methaneiminium hexafluorophosphate
DIAD: Diisopropyl azodicarboxylate
TBAF: Tetrabutylammonium fluoride
DIPEA: Diisopropylethylamine
Boc: Tert-butoxycarbonyl
$Boc_2O$: Di-tert-butyl dicarbonate
DMAP: Dimethylaminopyridine Synthetic Example 1 Synthesis of (R)-tert-butyl 3-(4-amino-3-iodo-1H-pyrazolo[3,4-d]pyrimidin-1-yl)piperidine-1-carboxylate

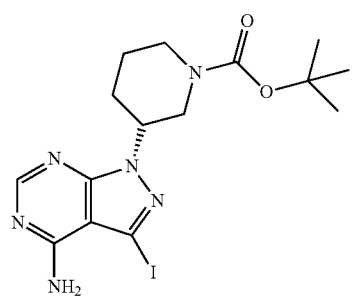

(Step 1) Synthesis of (S)-tert-butyl 3-(methylsulfonyloxy)piperidine-1-carboxylate 20 g of (S)—N-Boc-3-pyridinol was dissolved in 100 mL of toluene, and 21 mL of triethylamine and 9.2 mL of methanesulfonyl chloride were added thereto at 0° C. The mixture was stirred for 1 hour under ice cooling, subsequently ethyl acetate and water were added thereto, and an organic layer was separated. The organic layer was washed with a saturated aqueous solution of sodium hydrogen carbonate, a saturated aqueous solution of ammonium chloride and water, and then was dried over anhydrous sodium sulfate. The solvent was distilled off under reduced pressure, and thus 26.8 g of the title compound was obtained as a colorless solid.

(Step 2) Synthesis of (R)-tert-butyl 3-(4-amino-3-iodo-1H-pyrazolo[3,4-d]pyrimidin-1-yl)piperidine-1-carboxylate A suspension solution of 14.6 g of 3-iodo-1H-pyrazolo[3,4-d]pyrimidin-4-amine synthesized by the method described in WO 2007/126841, 25 g of (S)-tert-butyl 3-(methylsulfonyloxy)piperidine-1-carboxylate obtained in Step 1, and 69 g of potassium carbonate in 150 mL of DMA was heated to 100° C., and was stirred for 10 hours. The suspension solution was cooled to room temperature, and then 300 mL of water was added thereto. A solid thus obtained was collected by filtration and washed with water, and the solid was dried. Thus, 26.9 g of the title compound was obtained as a yellow solid. Physical property value: m/z [M+H]$^+$ 446.2

Synthetic Example 2 Synthesis of (R)-4-amino-1-(1-(tert-butyloxycarbonyl)piperidin-3-yl)-1H-pyrazolo[3,4-d]pyrimidine-3-carboxylic acid

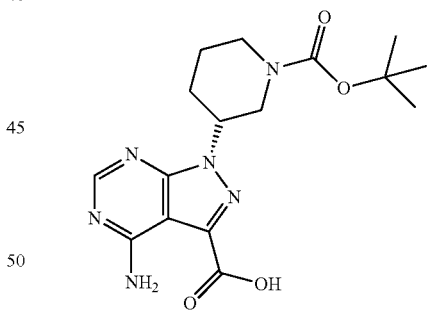

2 g of (R)-tert-butyl 3-(4-amino-3-iodo-1H-pyrazolo[3,4-d]pyrimidin-1-yl)piperidine-1-carboxylate obtained in Synthetic Example 1, 3 mL of 2-diethylaminoethanol, and 158 mg of Pd(PPh$_3$)$_2$Cl$_2$ were dissolved in 20 mL of NMP. After the system was purged with carbon monoxide, and then the solution was heated to 120° C. After the solution was stirred for 1 hour, the solution was cooled to room temperature. 10 mL of methanol was added thereto, and then 6 mL of a 5 N aqueous solution of sodium hydroxide was added thereto. The mixture was stirred for 10 minutes. Water was added thereto, and then the aqueous layer was washed with ethyl acetate. The aqueous layer was adjusted to pH 4 with hydrochloric acid, and a solid thus precipitated was collected by filtration, washed with water, and then dried. Thus, 1.26 g of the title compound was obtained as a pale yellow solid. Physical property value: m/z [M+H]⁺ 363.1

Synthetic Example 3 Synthesis of (R)-4-amino-1-(1-(tert-butyloxycarbonyl)pyrrolidin-3-yl)-1H-pyrazolo[3,4-d]pyrimidine-3-carboxylic acid

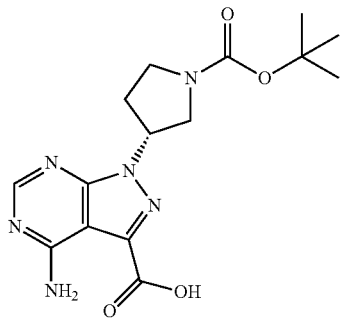 [SMILES: CC(C)(C)OC(=O)N1CC[C@@H](n2nc(C(=O)O)c3c(N)ncnc32)C1]

(Step 1) Synthesis of (S)-tert-butyl 3-(methylsulfonyloxy)pyrrolidine-1-carboxylate 935 mg of (S)-(−)-N-Boc-3-pyrrolidinol was dissolved in 15 mL of chloroform, and 1.04 mL of triethylamine and 467 μL of methanesulfonyl chloride were added thereto under ice cooling. The mixture was stirred for 1.5 hours at room temperature, subsequently ethyl acetate and water were added thereto, and an organic layer was separated. The organic layer was washed with a saturated aqueous solution of sodium hydrogen carbonate, a saturated aqueous solution of ammonium chloride, and water, and then was dried over anhydrous sodium sulfate. The solvent was distilled off under reduced pressure, and thus 1.3 g of the title compound was obtained as a colorless oily substance. Physical property value: m/z [M+H]⁺ 266.1

(Step 2) Synthesis of (R)-tert-butyl 3-(4-amino-3-iodo-1H-pyrazolo[3,4-d]pyrimidin-1-yl)pyrrolidine-1-carboxylate A suspension of 20.0 g of 3-iodo-1H-pyrazolo[3,4-d]pyrimidin-4-amine synthesized by the method described in WO 2007/126841, 23 g of (S)-tert-butyl 3-(methylsulfonyloxy)pyrrolidine-1-carboxylate obtained in Step 1, and 32 g of potassium carbonate in 200 mL of DMA, was heated to 85° C., and was stirred for 3 hours. The solution was cooled to room temperature, and then a solid obtained by adding 400 mL of water thereto was collected by filtration, washed with water, and then dried. Thus, 23.5 g of the title compound was obtained as a pale yellow solid. Physical property value: m/z [M+H]⁺ 431.0

(Step 3) Synthesis of (R)-4-amino-1-(1-(tert-butyloxycarbonyl)pyrrolidin-3-yl)-1H-pyrazolo[3,4-d]pyrimidine-3-carboxylic acid 2.0 g of (R)-tert-butyl 3-(4-amino-3-iodo-1H-pyrazolo[3,4-d]pyrimidin-1-yl)pyrrolidine-1-carboxylate obtained in the above Step 2, 3.1 mL of 2-diethylaminoethanol, and 163 mg of Pd(PPh₃)₂Cl₂ were dissolved in 20 mL of NMP. The system was purged with carbon monoxide, and then was heated to 120° C. After the solution was stirred for 1 hour, the solution was cooled to room temperature, and 10 mL of methanol was added thereto. Subsequently, 6 mL of a 5 N aqueous solution of sodium hydroxide was added thereto, and the mixture was stirred for 10 minutes. Water was added thereto, subsequently the aqueous layer was washed with chloroform, and the aqueous layer was adjusted to pH 4 with hydrochloric acid. A solid thus precipitated was collected by filtration, washed with water, and then dried. Thus, 1.35 g of the title compound was obtained as a pale yellow solid. Physical property value: m/z [M+H]⁺ 349.1

Synthetic Example 4 Synthesis of 5-cyanobenzo[d]oxazol-2-amine

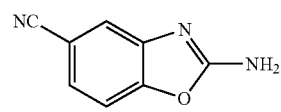

15.1 g of 3-amino-4-hydroxybenzonitrile was dissolved in a mixture of 75 mL of ethanol and 75 mL of water, and 14.7 g of bromocyan was added in small portions to the solution under ice cooling. The mixture was stirred for 2 hours at room temperature, and was ice-cooled again. 112 mL of a 2 N aqueous solution of sodium hydroxide was added to the solution, and the mixture was stirred for another 30 minutes. Most of ethanol was roughly removed with an evaporator, and the residue was collected by filtration. The filter cake was washed with water, and thus 12.12 g of the title compound was obtained.

Physical property value: m/z [M+H]⁺ 161.1

Example 1 Synthesis of (R)-1-(1-acryloylpiperidin-3-yl)-4-amino-N-(5-chlorobenzo[d]oxazol-2-yl)-1H-pyrazolo[3,4-d]pyrimidine-3-carboxamide (Example Compound 1)

(Step 1) Synthesis of (R)-tert-butyl-3-(4-amino-3-((5-chlorobenzo[d]oxazol-2-yl)carbamoyl)-1H-pyrazolo[3,4-d]pyrimidin-1-yl)piperidine-1-carboxylate To a suspension solution of 94 mg of (R)-4-amino-1-(1-(tert-butyloxycarbonyl)piperidin-3-yl)-1H-pyrazolo[3,4-d]pyrimidine-3-carboxylic acid obtained in Synthetic Example 2 in 4 mL of THF, 50 mg of CDI was added, and the mixture was stirred for 3 hours at room temperature. 66 mg of 5-chlorobenzo[d]oxazol-2-amine was added thereto under ice cooling, and a 1.0 M THF solution of lithium hexamethyldisilazane was added dropwise thereto. The mixture was stirred for 30 minutes under ice cooling, 1 mL of water was added thereto, and the solvent THF was removed. A solid obtained by adding 4 mL of water to the residue was separated by filtration, and was washed with 5 mL of hexane/ethyl acetate=1/1. Thus, 106 mg of the title compound was obtained as a white solid. Physical property value: m/z [M+H]⁺ 513.2

(Step 2) Synthesis of Example Compound 1

5.6 g of (R)-tert-butyl-3-(4-amino-3-((5-chlorobenzo[d]oxazol-2-yl)carbamoyl)-1H-pyrazolo[3,4-d]pyrimidin-1-yl)piperidine-1-carboxylate obtained in Step 1 was mixed with 1 mL of 4 N hydrochloric acid/1,4-dioxane, the mixture was stirred for 1 hour, and then the solvent was removed with an evaporator. 2 mL of chloroform and 7.6 μL of triethylamine were added to the residue, the mixture was ice-cooled, and then 0.9 µL of acryloyl chloride was added thereto. After the mixture was stirred for 1.5 hours, the reaction was terminated with a saturated aqueous solution of sodium bicarbonate, and extracted with chloroform. The organic layer was dried over sodium sulfate, and then a residue obtained after removal of the solvent was purified by a silica gel column (eluant: ethyl acetate/methanol). Thus, 2.6 mg of the title compound was obtained as a white solid.

Example 2 Synthesis of (R)-1-(1-acryloylpiperidin-3-yl)-4-amino-N-(5-bromobenzo[d]oxazol-2-yl)-1H-pyrazolo[3,4-d]pyrimidine-3-carboxamide (Example Compound 2)

The title compound was obtained as a white solid from (R)-4-amino-1-(1-(tert-butyloxycarbonyl)piperidin-3-yl)-1H-pyrazolo[3,4-d]pyrimidine-3-carboxylic acid of Synthetic Example 2 and 5-bromobenzo[d]oxazol-2-amine according to the procedure described in Example 1.

Example 3 Synthesis of (R)-1-(1-acryloylpiperidin-3-yl)-4-amino-N-(5-(thiophen-2-yl)benzo[d]oxazol-2-yl)-1H-pyrazolo[3,4-d]pyrimidine-3-carboxamide (Example Compound 3)

(Step 1) Synthesis of 5-(thiophen-2-yl)benzo[d]oxazol-2-amine 100 mg of 5-bromobenzo[d]oxazol-2-amine, 249 mg of potassium phosphate, and 90 mg of thiophen-2-ylboronic acid were suspended in a mixture of 2.5 mL of DME and 0.5 mL of water. 38 mg of 1,1'-bis(diphenylphosphino)ferrocene-palladium(II) dichloride-dichloromethane was added thereto, and the mixture was irradiated at 140° C. for 20 minutes with a microwave reaction apparatus. The solvent was removed from the reaction solution, and the residue was purified by amine gel chromatography (eluent: chloroform/methanol), and thus 93 mg of the title compound was obtained as a pale brown solid. Physical property value: m/z [M+H]$^+$ 216.8

(Step 2) Synthesis of (R)-tert-butyl-3-(4-amino-3-((5-thiophen-2-yl)benzo[d]oxazol-2-yl)carbamoyl)-1H-pyrazolo[3,4-d]pyrimidin-1-yl)piperidine-1-carboxylate To a suspension solution of 19 mg of (R)-4-amino-1-(1-(tert-butyloxycarbonyl)piperidin-3-yl)-1H-pyrazolo[3,4-d]pyrimidine-3-carboxylic acid obtained in Synthetic Example 2 in 2 mL of THF, 10 mg of CDI was added, and the mixture was stirred for 2 hours at room temperature. 17 mg of 5-(thiophen-2-yl)benzo[d]oxazol-2-amine obtained in Step 1 was added thereto under ice cooling, and 105 µl of a 1.0 M THF solution of lithium hexamethyldisilazane was added dropwise thereto. The mixture was stirred for 30 minutes under ice cooling, subsequently 1 mL of water was added thereto, and the solvent THF was removed. A solid obtained by adding 4 mL of water to the residue was separated by filtration, and was washed with 5 mL of hexane/ethyl acetate=1/1. Thus, 13 mg of the target substance was obtained as a pale brown solid. Physical property value: m/z [M+H]$^+$ 561.3

(Step 3) Synthesis of Example Compound 3

1 mL of 4 N hydrochloric acid/1,4-dioxane was added to 9 mg of (R)-tert-butyl-3-(4-amino-3-((5-(thiophen-2-yl)benzo[d]oxazol-2-yl)carbamoyl)-1H-pyrazolo[3,4-d]pyrimidin-1-yl)piperidine-1-carboxylate obtained in (Step 2), the mixture was stirred for 1 hours, and then the solvent was removed with an evaporator. 2 mL of chloroform and 12 µl of triethylamine were added to the residue, the mixture was ice-cooled, and then 1.3 µl of acryloyl chloride was added thereto. After the mixture was stirred for 1.5 hours, the reaction was terminated with a saturated aqueous solution of sodium bicarbonate, and extracted with chloroform. The organic layer was dried over sodium sulfate, and then the residue obtained after solvent removal was purified by reverse phase preparative HPLC purification (water/acetonitrile (0.1% formic acid)). Thus, 2.1 mg of the title compound was obtained as a white solid.

Example 4 Synthesis of (R)-4-amino-N-(5-chlorobenzo[d]oxazol-2-yl)-1-(1-methacryloylpiperidin-3-yl)-1H-pyrazolo[3,4-d]pyrimidine-3-carboxamide (Example Compound 4)

The title compound was obtained as a white solid according to the procedure described in Example 1, by using methacryloyl chloride instead of acryloyl chloride.

Example 5 Synthesis of (R,E)-4-amino-N-(5-chlorobenzo[d]oxazol-2-yl)-1-(1-(but-2-enoyl)piperidin-3-yl)-1H-pyrazolo[3,4-d]pyrimidine-3-carboxamide (Example Compound 5)

The title compound was obtained as a white solid according to the procedure described in Example 1, by using crotonic acid chloride instead of acryloyl chloride.

Example 6 Synthesis of (R)-1-(1-acryloylpiperidin-3-yl)-4-amino-N-(5-cyanobenzo[d]oxazol-2-yl)-1H-pyrazolo[3,4-d]pyrimidine-3-carboxamide (Example Compound 6)

(Step 1) Synthesis of (R)-tert-butyl-3-(4-amino-3-((5-cyanobenzo[d]oxazol-2-yl)carbamoyl)-1H-pyrazolo[3,4-d]pyrimidin-1-yl)piperidine-1-carboxylate 2.32 g of (R)-4-amino-1-(1-(tert-butyloxycarbonyl)piperidin-3-yl)-1H-pyrazolo[3,4-d]pyrimidine-3-carboxylic acid obtained in Synthetic Example 2 was dissolved in 25 mL of DMA, 2.01 g of CDI was added thereto, and the mixture was stirred for 1 hour at room temperature. 1.12 g of 5-cyanobenzo[d]oxazol-2-amine was added to the reaction solution, and thereafter, 1.23 g of sodium tert-butyrate was added thereto. The mixture was stirred for 2 hours at room temperature, and water was added thereto. Subsequently, the pH was adjusted with 2 N hydrochloric acid, and thereby a solid was precipitated therefrom. The solid was collected by filtration and dried. Thus, 2.66 g of the title compound was obtained as a pale yellow solid. Physical property value: m/z [M+H]$^+$ 505.3

(Step 2) Synthesis of Example Compound 6

2.1 g of (R)-tert-butyl-3-(4-amino-3-((5-cyanobenzo[d]oxazol-2-yl)carbamoyl)-1H-pyrazolo[3,4-d]pyrimidin-1-yl)piperidine-1-carboxylate obtained in Step 1 was suspended in 10 mL of dichloromethane, and 10 mL of TFA was added thereto at room temperature. The mixture was stirred for 2 hours, and then the TFA was removed with an evaporator. Furthermore, the residue was azeotropically distilled with toluene, the residue was mixed with a mixture of 20 mL of NMP and 2 mL of water, and the mixture was ice-cooled. 2.88 g of potassium carbonate and 0.4 mL of acryloyl chloride were added thereto, and the mixture was stirred under ice cooling. After 2 hours, water and 2 N hydrochloric acid were added thereto to adjust the pH, and a solid thus obtained was collected by filtration. Thereafter, the solid was purified by silica gel chromatography (chloroform-methanol), and thus 0.7 g of the target substance was obtained as a white solid.

Example 7 Synthesis of (R)-1-(1-acryloylpiperidin-3-yl)-4-amino-N-(5-methoxybenzo[d]oxazol-2-yl)-1H-pyrazolo[3,4-d]pyrimidine-3-carboxamide (Example Compound 7)

The title compound was obtained as a pale brown solid according to the procedure described in Example 6, from (R)-4-amino-1-(1-(tert-butyloxycarbonyl)piperidin-3-yl)-1H-pyrazolo[3,4-d]pyrimidine-3-carboxylic acid of Synthetic Example 2 and 5-methoxybenzo[d]oxazol-2-amine.

Example 8 Synthesis of (R)-1-(1-acryloylpiperidin-3-yl)-4-amino-N-(5-(2-methoxyethyl)benzo[d]oxazol-2-yl)-1H-pyrazolo[3,4-d]pyrimidine-3-carboxamide (Example Compound 8)

The title compound was obtained as a white solid according to the procedure described in Example 6, from (R)-4-amino-1-(1-(tert-butyloxycarbonyl)piperidin-3-yl)-1H-pyrazolo[3,4-d]pyrimidine-3-carboxylic acid of Synthetic Example 2 and 5-(2-methoxyethyl)benzo[d]oxazol-2-amine.

Example 9 Synthesis of (R)-1-(1-acryloylpiperidin-3-yl)-4-amino-N-(oxazolo[4,5-b]pyridin-2-yl)-1H-pyrazolo[3,4-d]pyrimidine-3-carboxamide (Example Compound 9)

The title compound was obtained as a white solid according to the procedure described in Example 6, from (R)-4-amino-1-(1-(tert-butyloxycarbonyl)piperidin-3-yl)-1H-pyrazolo[3,4-d]pyrimidine-3-carboxylic acid of Synthetic Example 2 and oxazolo[4,5-b]pyridin-2-amine.

Example 10 Synthesis of (R)-1-(1-acryloylpiperidin-3-yl)-4-amino-N-(4-methylbenzo[d]oxazol-2-yl)-1H-pyrazolo[3,4-d]pyrimidine-3-carboxamide (Example Compound 10)

The title compound was obtained as a white solid according to the procedure described in Example 6, from (R)-4-amino-1-(1-(tert-butyloxycarbonyl)piperidin-3-yl)-1H-pyrazolo[3,4-d]pyrimidine-3-carboxylic acid of Synthetic Example 2 and 4-methylbenzo[d]oxazol-2-amine.

Example 11 Synthesis of (R)-4-amino-N-(5-fluorobenzo[d]oxazol-2-yl)-1-(1-methacryloylpiperidin-3-yl)-1H-pyrazolo[3,4-d]pyrimidine-3-carboxamide (Example Compound 11)

The title compound was obtained as a white solid according to the procedure described in Example 6, by using (R)-4-amino-N-(5-fluorobenzo[d]oxazol-2-yl)-1-(piperidin-3-yl)-1H-pyrazolo[3,4-d]pyrimidine-3-carboxamide obtained in Example 12 (Step 2), and by using methacryloyl chloride instead of acryloyl chloride.

Example 12 Synthesis of (R)-1-(1-acryloylpiperidin-3-yl)-4-amino-N-(5-fluorobenzo[d]oxazol-2-yl)-1H-pyrazolo[3,4-d]pyrimidine-3-carboxamide (Example Compound 12)

(Step 1) Synthesis of (R)-tert-butyl-3-(4-amino-3-((5-fluorobenzo[d]oxazol-2-yl)carbamoyl)-1H-pyrazolo[3,4-d]pyrimidin-1-yl)piperidine-1-carboxylate To a solution of 1.0 g of (R)-4-amino-1-(1-(tert-butyloxycarbonyl)piperidin-3-yl)-1H-pyrazolo[3,4-d]pyrimidine-3-carboxylic acid obtained in Synthetic Example 2 in 10 mL of DMA, 895 mg of CDI was added, and the mixture was stirred for 1 hour at room temperature. 462 mg of 5-fluorobenzo[d]oxazol-2-amine was added thereto, and 9 mL of a 1.0 M THF solution of sodium tert-butyrate was added dropwisely thereto. The mixture was stirred for 30 minutes at room temperature, and then 10 mL of a 1 N aqueous solution of sodium hydroxide was added thereto, and the solvent THF was removed. After the mixture was stirred for 1 hour, 2 N hydrochloric acid was added to the residue for precipitation, and water-methanol was added for complete precipitation. Subsequently, a solid thus obtained was collected by filtration, and thus 1.14 g of the title compound was obtained as a light yellow solid.

Physical property value: m/z [M+H]$^+$ 497.2

(Step 2) Synthesis of (R)-4-amino-N-(5-fluorobenzo[d]oxazol-2-yl)-1-(piperidin-3-yl)-1H-pyrazolo[3,4-d]pyrimidine-3-carboxamide 3.06 g of (R)-tert-butyl-3-(4-amino-3-(5-fluorobenzo[d]oxazol-2-ylcarbonyl)-1H-pyrazolo[3,4-d]pyrimidin-1-yl)piperidine-1-carboxylate obtained in Step 1 and 5.5 g of sodium iodide were suspended in 30 mL of acetonitrile, and 4.7 mL of trimethylsilyl chloride was added thereto at room temperature. The mixture was stirred for 1 hour at room temperature, a saturated aqueous solution of sodium bicarbonate was added thereto, and thereby a solid was precipitated. After the system was stirred for 10 minutes, the solid was collected by filtration and dried, and thus 2.07 g of the title compound was obtained as a light brown solid. Physical property value: m/z [M+H]$^+$ 398.0

(Step 3) Synthesis of Example Compound 12

2 g of (R)-4-amino-N-(5-fluorobenzo[d]oxazol-2-yl)-1-(piperidin-3-yl)-1H-pyrazolo[3,4-d]pyrimidine-3-carboxamide obtained in Step 2 and 2.1 g of potassium carbonate were dissolved in a mixture of 20 mL of NMP and 2 mL of water, and the solution was stirred under ice cooling. 0.4 mL of acryloyl chloride was added thereto, and the mixture was stirred for 1 hour. Water was added thereto, and the pH was adjusted with hydrochloric acid. A solid precipitated therefrom was collected by filtration. The solid thus collected by filtration was purified by silica gel chromatography (eluent: chloroform-methanol), and 1.79 g of the title compound was obtained as a white solid.

Example 13 Synthesis of (R)-1-(1-acryloylpiperidin-3-yl)-4-amino-N-(benzo[d]oxazol-2-yl)-1H-pyrazolo[3,4-d]pyrimidine-3-carboxamide (Example Compound 13)

(Step 1) Synthesis of (R)-tert-butyl-3-(4-amino-3-((benzo[d]oxazol-2-yl)carbamoyl)-1H-pyrazolo[3,4-d]pyrimidin-1-yl)piperidine-1-carboxylate 300 mg of (R)-tert-butyl 3-(4-amino-3-iodo-1H-pyrazolo[3,4-d]pyrimidin-1-yl)piperidine-1-carboxylate obtained in Synthetic Example 1 was dissolved in 3 mL of NMP. 118 mg of benzo[d]oxazol-2-amine, 20 mg of xantphos, and 0.15 mL of N-methylmorpholine were added thereto, and a degassing operation was carried out. Thereafter, 7.6 mg of palladium acetate was added thereto, and under a carbon monoxide atmosphere, the mixture was heated to 110° C. and stirred for 2 hours. After the mixture was cooled, 4.5 mL of methanol and 0.45 mL of a 5 N aqueous solution of sodium hydroxide were added thereto, and the mixture was stirred for 30 minutes at room temperature. Thereafter, the pH was adjusted to 5.3 with 2 N hydrochloric acid, and a solid thus obtained was collected by filtration. The crude product was purified by a silica gel column (chloroform-methanol), and thus 257 mg of the title compound was obtained as a white solid.

Physical property value: m/z $[M+H]^+$ 479.3

(Step 2) Synthesis of Example Compound 13

5 g of (R)-tert-butyl-3-(4-amino-3-((benzo[d]oxazol-2-yl)carbamoyl)-1H-pyrazolo[3,4-d]pyrimidin-1-yl)piperidine-1-carboxylate obtained in Step 1 was suspended in 50 mL of acetonitrile, and 7.85 g of sodium iodide was added thereto. 6.65 mL of trimethylsilyl chloride was added dropwise thereto with stirring at room temperature, and the mixture was stirred for 1 hour. 87.5 mL of water and 12.5 mL of a 5 N aqueous solution of sodium hydroxide were added thereto, and then the system was ice-cooled. 0.895 mL of acryloyl chloride was added dropwise thereto, and the mixture was stirred for 1 hour under ice cooling. A solid obtained by adding water thereto was collected by filtration, washed with water, and dried. Thus, 4.13 g of the title compound was obtained as a white solid.

Example 14 Synthesis of (R,E)-4-amino-N-(benzo[d]oxazol-2-yl)-1-(1-(but-2-enoyl)piperidin-3-yl)-1H-pyrazolo[3,4-d]pyrimidine-3-carboxamide (Example Compound 14)

The title compound was obtained as a white solid according to the procedure described in Example 13, by using crotonic acid chloride instead of acryloyl chloride.

Example 15 Synthesis of (R,E)-4-amino-N-(5-chlorobenzo[d]oxazol-2-yl)-1-(1-(4-(dimethylamino)but-2-enoyl)piperidin-3-yl)-1H-pyrazolo[3,4-d]pyrimidine-3-carboxamide (Example Compound 15)

1 mL of 4 N hydrochloric acid/1,4-dioxane was added to 5 mg of (R)-tert-butyl-3-(4-amino-3-((5-chlorobenzo[d]oxazol-2-yl)carbamoyl)-1H-pyrazolo[3,4-d]pyrimidin-1-yl)piperidine-1-carboxylate obtained in Step 1 of Example 1, and the mixture was stirred for 10 minutes. Thereafter, the solvent was removed with an evaporator, and the system was azeotropically distilled with toluene. The residue was dissolved in 1 mL of DMF, and 8.5 μL of DIPEA, 2.4 mg of (E)-4-(dimethylamino)but-2-enoic acid hydrochloride, and 5.5 mg of HATU were added thereto. The mixture was stirred for 1 hour at room temperature, and then the solution was concentrated under reduced pressure. The residue was purified by reverse phase preparative HPLC purification (water/acetonitrile (0.1% formic acid)), and thus 3.96 mg of the title compound was obtained as a white solid.

Example 16 Synthesis of (R,E)-4-amino-N-(5-chlorobenzo[d]oxazol-2-yl)-1-(1-(4-(ethyl(methyl)amino)but-2-enoyl)piperidin-3-yl)-1H-pyrazolo[3,4-d]pyrimidine-3-carboxamide (Example Compound 16)

The title compound was obtained as a white solid according to the procedure described in Example 15, by using (E)-4-(ethyl(methyl)amino)but-2-enoic acid hydrochloride instead of (E)-4-(dimethylamino)but-2-enoic acid hydrochloride.

Example 17 Synthesis of (R,E)-4-amino-N-(5-chlorobenzo[d]oxazol-2-yl)-1-(1-(4-(diethylamino)but-2-enoyl)piperidin-3-yl)-1H-pyrazolo[3,4-d]pyrimidine-3-carboxamide (Example Compound 17)

The title compound was obtained as a white solid according to the procedure described in Example 15, by using (E)-4-(diethylamino)but-2-enoic acid hydrochloride instead of (E)-4-(dimethylamino)but-2-enoic acid hydrochloride.

Example 18 Synthesis of (R,E)-4-amino-N-(5-chlorobenzo[d]oxazol-2-yl)-1-(1-(4-(isopropyl(methyl)amino)but-2-enoyl)piperidin-3-yl)-1H-pyrazolo[3,4-d]pyrimidine-3-carboxamide (Example Compound 18)

The title compound was obtained as a white solid according to the procedure described in Example 15, by using (E)-4-(isopropyl(methyl)amino)but-2-enoic acid hydrochloride instead of (E)-4-(dimethylamino)but-2-enoic acid hydrochloride.

Example 19 Synthesis of (R,E)-4-amino-N-(5-chlorobenzo[d]oxazol-2-yl)-1-(1-(4-(pyrrolidin-1-yl)but-2-enoyl)piperidin-3-yl)-1H-pyrazolo[3,4-d]pyrimidine-3-carboxamide (Example Compound 19)

The title compound was obtained as a white solid according to the procedure described in Example 15, by using (E)-4-(pyrrolidin-1-yl)but-2-enoic acid hydrochloride instead of (E)-4-(dimethylamino)but-2-enoic acid hydrochloride.

Example 20 Synthesis of (R,E)-4-amino-N-(5-chlorobenzo[d]oxazol-2-yl)-1-(1-(4-(piperidin-1-yl)but-2-enoyl)piperidin-3-yl)-1H-pyrazolo[3,4-d]pyrimidine-3-carboxamide (Example Compound 20)

The title compound was obtained as a white solid according to the procedure described in Example 15, by using (E)-4-(piperidin-1-yl)but-2-enoic acid hydrochloride instead of (E)-4-(dimethylamino)but-2-enoic acid hydrochloride.

Example 21 Synthesis of (R,E)-4-amino-N-(5-(thiophen-2-yl)benzo[d]oxazol-2-yl)-1-(1-(4-(dimethylamino)but-2-enoyl)piperidin-3-yl)-1H-pyrazolo[3,4-d]pyrimidine-3-carboxamide (Example Compound 21)

The title compound was obtained as a white solid according to the procedure described in Example 15, by using (R)-tert-butyl-3-(4-amino-3-((5-(thiophen-2-yl)benzo[d]oxazol-2-yl)carbamoyl)-1H-pyrazolo[3,4-d]pyrimidin-1-yl)piperidine-1-carboxylate obtained in Example 3 (Step 2).

Example 22 Synthesis of (R)-4-amino-N-(benzo[d]oxazol-2-yl)-1-(1-but-2-ynoyl)piperidin-3-yl)-1H-pyrazolo[3,4-d]pyrimidine-3-carboxamide (Example Compound 22)

The title compound was obtained as a pale yellow solid according to the procedure described in Example 15, by using (R)-tert-butyl-3-(4-amino-3-((benzo[d]oxazol-2-yl)

carbamoyl)-1H-pyrazolo[3,4-d]pyrimidin-1-yl)piperidine-1-carboxylate obtained in Example 13 (Step 1), and but-2-ynoic acid instead of (E)-4-(dimethylamino)but-2-enoic acid hydrochloride.

Example 23 Synthesis of (R)-1-(1-acryloylpiperidin-3-yl)-4-amino-N-(5,6-dimethylbenzo[d]oxazol-2-yl)-1H-pyrazolo[3,4-d]pyrimidine-3-carboxamide (Example Compound 23)

(Step 1) Synthesis of (R)-1-(1-acyloxypiperidin-3-yl)-4-amino-1H-pyrazolo[3,4-d]pyrimidine-3-carboxylic acid To 1 g of (R)-4-amino-1-(1-(tert-butyloxycarbonyl)piperidin-3-yl)-1H-pyrazolo[3,4-d]pyrimidine-3-carboxylic acid obtained in Synthetic Example 2, 15 mL of 4 N hydrochloric acid/1,4-dioxane was added, and the mixture was stirred for 1 hour at room temperature. Thereafter, the solvent was removed, and the system was azeotropically distilled by adding toluene thereto. 50 mL of chloroform and 3.8 mL of triethylamine were added to the residue. While the mixture was stirred, 780 μl of acryloyl chloride was slowly added thereto. After completion of the reaction was confirmed, the reaction was terminated by adding 2-propanol. The solvent was removed, and an aqueous solution of formic acid was added to the residue. When the mixture was adjusted to pH 3, a solid was precipitated. A solid thus obtained was collected by filtration and dried, and thus 840 mg of the title compound was obtained as a yellow solid.
Physical property value: m/z [M+H]$^+$ 318.1

(Step 2) Synthesis of Example Compound 23

5 mg of (R)-1-(1-acyloxypiperidin-3-yl)-4-amino-1H-pyrazolo[3,4-d]pyrimidine-3-carboxylic acid obtained in the above Step 1 was dissolved in 150 μl of DMF. To that solution, 8.26 μl of diisopropylethylamine, 3.85 mg of 5,6-dimethylbenzo[d]oxazol-2-amine, and 9 mg of HATU were added. After the mixture was stirred overnight, 850 μl of DMSO was added thereto, and the mixture was purified by reverse phase preparative HPLC purification (water/acetonitrile (0.1% formic acid)). Thus, 1.2 mg of the title compound was obtained as a white solid.

Example 24 Synthesis of (R)-1-(1-acryloylpyrrolidin-3-yl)-4-amino-N-(5-chlorobenzo[d]oxazol-2-yl)-1H-pyrazolo[3,4-d]pyrimidine-3-carboxamide (Example Compound 24)

(Step 1) Synthesis of (R)-tert-butyl-3-(4-amino-3-((5-chlorobenzo[d]oxazol-2-yl)carbamoyl)-1H-pyrazolo[3,4-d]pyrimidin-1-yl)pyridine-1-carboxylate To a solution of 100 mg of (R)-4-amino-1-(1-(tert-butyloxycarbonyl)pyrrolidin-3-yl)-1H-pyrazolo[3,4-d]pyrimidine-3-carboxylic acid obtained in Synthetic Example 3 in 5 mL of DMF, 56 mg of CDI was added, and the mixture was stirred for 1 hour at room temperature. 73 mg of 5-chlorobenzo[d]oxazol-2-amine was added thereto under ice cooling, and 17 mg of 60% sodium hydride was added thereto. After the mixture was stirred for 30 minutes under ice cooling, 1 mL of water was added thereto to terminate the reaction. The reaction solution was concentrated, and was purified by silica gel column chromatography (eluant: chloroform/methanol). Thus, 114 mg of the title compound was obtained as a white solid. Physical property value: m/z [M+H]$^+$ 499.1

(Step 2) Synthesis of Example Compound 24

15 mg of (R)-tert-butyl-3-(4-amino-3-((5-chlorobenzo[d]oxazol-2-yl)carbamoyl)-1H-pyrazolo[3,4-d]pyrimidin-1-yl)pyrrolidine-1-carboxylate obtained in Step 1 was mixed with 1.5 mL of 4 N hydrochloric acid/1,4-dioxane, the mixture was stirred for 1 hour, and then the solvent was removed with an evaporator. 2 mL of chloroform and 21 μl of triethylamine were added to the residue, the mixture was ice-cooled, and then 2.4 μl of acryloyl chloride was added thereto. After the mixture was stirred for 3 hours, the reaction was terminated with a saturated aqueous solution of sodium bicarbonate, and extracted with chloroform. The organic layer was dried over sodium sulfate, and then a residue obtained after removal of the solvent was purified by a silica gel column (eluent: ethyl acetate/methanol). Thus, 6.8 mg of the title compound was obtained as a white solid.

Example 25 Synthesis of (R,E)-4-amino-N-(5-chlorobenzo[d]oxazol-2-yl)-1-(1-(but-2-enoyl)pyrrolidin-3-yl)-1H-pyrazolo[3,4-d]pyrimidine-3-carboxamide (Example Compound 25)

The title compound was obtained as a white solid according to the procedure described in Example 24, by using crotonic acid chloride instead of acryloyl chloride.

Example 26 Synthesis of (R,E)-4-amino-N-(5-chlorobenzo[d]oxazol-2-yl)-1-(1-(3-methylbut-2-enoyl)pyrrolidin-3-yl)-1H-pyrazolo[3,4-d]pyrimidine-3-carboxamide (Example Compound 26)

The title compound was obtained as a white solid according to the procedure described in Example 24, by using 3-methylbut-2-enoyl chloride instead of acryloyl chloride.

Example 27 Synthesis of (R)-1-(1-acryloylpyrrolidin-3-yl)-4-amino-N-(benzo[d]oxazol-2-yl)-1H-pyrazolo[3,4-d]pyrimidine-3-carboxamide (Example Compound 27)

The title compound was obtained as a white solid according to the procedure described in Example 24, from (R)-4-amino-1-(1-(tert-butyloxycarbonyl)pyrrolidin-3-yl)-1H-pyrazolo[3,4-d]pyrimidine-3-carboxylic acid of Synthetic Example 3 and benzo[d]oxazol-2-amine.

Example 28 Synthesis of (R)-1-(1-acryloylpyrrolidin-3-yl)-4-amino-N-(5-(thiophen-2-yl)benzo[d]oxazol-2-yl)-1H-pyrazolo[3,4-d]pyrimidine-3-carboxamide (Example Compound 28)

The title compound was obtained as a white solid according to the procedure described in Example 24, from (R)-4-amino-1-(1-(tert-butyloxycarbonyl)pyrrolidin-3-yl)-1H-pyrazolo[3,4-d]pyrimidine-3-carboxylic acid of Synthetic Example 3 and 5-(thiophen-2-yl)benzo[d]oxazol-2-amine.

Example 29 Synthesis of (R)-1-(1-acryloylpyrrolidin-3-yl)-4-amino-N-(5-methylbenzo[d]oxazol-2-yl)-1H-pyrazolo[3,4-d]pyrimidine-3-carboxamide (Example Compound 29)

The title compound was obtained as a pale yellow according to the procedure described in Example 24, from (R)-4- amino-1-(1-(tert-butyloxycarbonyl)pyrrolidin-3-yl)-1H-pyrazolo[3,4-d]pyrimidine-3-carboxylic acid of Synthetic Example 3 and 5-methylbenzo[d]oxazol-2-amine.

Example 30 Synthesis of (R)-1-(1-acryloylpyrrolidin-3-yl)-4-amino-N-(5-fluorobenzo[d]oxazol-2-yl)-1H-pyrazolo[3,4-d]pyrimidine-3-carboxamide (Example Compound 30)

The title compound was obtained as a pale yellow solid according to the procedure described in Example 24, from (R)-4-amino-1-(1-(tert-butyloxycarbonyl)pyrrolidin-3-yl)-1H-pyrazolo[3,4-d]pyrimidine-3-carboxylic acid of Synthetic Example 3 and 5-fluorobenzo[d]oxazol-2-amine.

Example 31 Synthesis of (R)-1-(1-acryloylpyrrolidin-3-yl)-4-amino-N-(5-(4-chlorophenyl)benzo[d]oxazol-2-yl)-1H-pyrazolo[3,4-d]pyrimidine-3-carboxamide (Example Compound 31)

(Step 1) Synthesis of 5-(4-chlorophenyl)benzo[d]oxazol-2-amine

The title compound was obtained as a white solid according to the procedure described in Step 1 of Example 3, by using 4-chlorophenylboronic acid instead of thiophen-2-ylboronic acid. Physical property value: m/z [M+H]$^+$ 245.1

(Step 2) Synthesis of Example Compound 31

The title compound was obtained as a white solid according to the procedure described in Example 24, from (R)-4-amino-1-(1-(tert-butyloxycarbonyl)pyrrolidin-3-yl)-1H-pyrazolo[3,4-d]pyrimidine-3-carboxylic acid of Synthetic Example 3 and 5-(4-chlorophenyl)benzo[d]oxazol-2-amine obtained in the above Step 1.

Example 32 Synthesis of (R,E)-4-amino-N-(5-chlorobenzo[d]oxazol-2-yl)-1-(1-(4-(dimethylamino)but-2-enoyl)pyrrolidin-3-yl)-1H-pyrazolo[3,4-d]pyrimidine-3-carboxamide (Example Compound 32)

To 15 mg of (R)-tert-butyl-3-(4-amino-3-((5-chlorobenzo[d]oxazol-2-yl)carbamoyl)-1H-pyrazolo[3,4-d]pyrimidin-1-yl)pyrrolidine-1-carboxylate obtained in Step 1 of Example 24, 1.5 mL of 4 N hydrochloric acid/1,4-dioxane was added, and the mixture was stirred for 10 minutes. Thereafter, the solvent was removed with an evaporator, and the system was azeotropically distilled with toluene. The residue was dissolved in 1 mL of DMF, and 13 μL of DIPEA, 3.7 mg of (E)-4-(dimethylamino)but-2-enoic acid hydrochloride, and 8.4 mg of HATU were added thereto. The mixture was stirred for 1 hour at room temperature, and then the solution was concentrated under reduced pressure. The residue was purified by reverse phase preparative HPLC purification (water/acetonitrile (0.1% formic acid)), and thus 4.2 mg of the title compound was obtained as a white solid.

Example 33 Synthesis of (R,E)-4-amino-N-(5-chlorobenzo[d]oxazol-2-yl)-1-(1-(4-ethyl(methyl)amino)but-2-enoyl)pyrrolidin-3-yl)-1H-pyrazolo[3,4-d]pyrimidine-3-carboxamide (Example Compound 33)

The title compound was obtained as a white solid according to the procedure described in Example 32, by using (E)-4-(ethyl(methyl)amino)but-2-enoic acid hydrochloride instead of (E)-4-(dimethylamino)but-2-enoic acid hydrochloride.

Example 34 Synthesis of (R,E)-4-amino-N-(5-chlorobenzo[d]oxazol-2-yl)-1-(1-(4-(diethylamino)but-2-enoyl)pyrrolidin-3-yl)-1H-pyrazolo[3,4-d]pyrimidine-3-carboxamide (Example Compound 34)

The title compound was obtained as a white solid according to the procedure described in Example 32, by using (E)-4-(diethylamino)but-2-enoic acid hydrochloride instead of (E)-4-(dimethylamino)but-2-enoic acid hydrochloride.

Example 35 Synthesis of (R,E)-4-amino-N-(5-chlorobenzo[d]oxazol-2-yl)-1-(1-(4-(isopropyl(methyl)amino)but-2-enoyl)pyrrolidin-3-yl)-1H-pyrazolo[3,4-d]pyrimidine-3-carboxamide (Example Compound 35)

The title compound was obtained as a white solid according to the procedure described in Example 32, by using (E)-4-(isopropyl(methyl)amino)but-2-enoic acid hydrochloride instead of (E)-4-(dimethylamino)but-2-enoic acid hydrochloride.

Example 36 Synthesis of (R,E)-4-amino-N-(5-chlorobenzo[d]oxazol-2-yl)-1-(1-(4-(pyrrolidin-1-yl)but-2-enoyl)pyrrolidin-3-yl)-1H-pyrazolo[3,4-d]pyrimidine-3-carboxamide (Example Compound 36)

The title compound was obtained as a white solid according to the procedure described in Example 32, by using (E)-4-(pyrrolidin-1-yl)but-2-enoic acid hydrochloride instead of (E)-4-(dimethylamino)but-2-enoic acid hydrochloride.

Example 37 Synthesis of (R,E)-4-amino-N-(5-chlorobenzo[d]oxazol-2-yl)-1-(1-(4-(piperidin-1-yl)but-2-enoyl)pyrrolidin-3-yl)-1H-pyrazolo[3,4-d]pyrimidine-3-carboxamide (Example Compound 37)

The title compound was obtained as a white solid according to the procedure described in Example 32, by using (E)-4-(piperidin-1-yl)but-2-enoic acid hydrochloride instead of (E)-4-(dimethylamino)but-2-enoic acid hydrochloride.

Example 38 Synthesis of (R)-1-(1-acryloylpyrrolidin-3-yl)-4-amino-N-(5-methoxybenzo[d]oxazol-2-yl)-1H-pyrazolo[3,4-d]pyrimidine-3-carboxamide (Example Compound 38)

The title compound was obtained as a white solid according to the procedure described in Example 6, from (R)-4-amino-1-(1-(tert-butyloxycarbonyl)pyrrolidin-3-yl)-1H-pyrazolo[3,4-d]pyrimidine-3-carboxylic acid of Synthetic Example 3 and 5-methoxybenzo[d]oxazol-2-amine.

Example 39 Synthesis of (R)-1-(1-acryloylpyrrolidin-3-yl)-4-amino-N-(5-cyanobenzo[d]oxazol-2-yl)-1H-pyrazolo[3,4-d]pyrimidine-3-carboxamide (Example Compound 39)

The title compound was obtained as a white solid according to the procedure described in Example 6, from (R)-4-amino-1-(1-(tert-butyloxycarbonyl)pyrrolidin-3-yl)-1H- pyrazolo[3,4-d]pyrimidine-3-carboxylic acid of Synthetic Example 3 and 5-cyanobenzo[d]oxazol-2-amine.

Example 40 Synthesis of (R)-1-(1-acryloylpyrrolidin-3-yl)-4-amino-N-(5-(2-methoxyethyl)benzo[d]oxazol-2-yl)-1H-pyrazolo[3,4-d]pyrimidine-3-carboxamide (Example Compound 40)

The compound was obtained as a pale yellow solid according to the procedure described in Example 6, from (R)-4-amino-1-(1-(tert-butyloxycarbonyl)pyrrolidin-3-yl)-1H-pyrazolo[3,4-d]pyrimidine-3-carboxylic acid of Synthetic Example 3 and 5-(2-methoxyethyl)benzo[d]oxazol-2-amine.

Example 41 Synthesis of (R)-1-(1-acryloylpyrrolidin-3-yl)-4-amino-N-(5-phenylbenzo[d]oxazol-2-yl)-1H-pyrazolo[3,4-d]pyrimidine-3-carboxamide (Example Compound 41)

(Step 1) Synthesis of (R)-tert-butyl-3-(4-amino-3-((5-phenylbenzo[d]oxazol-2-yl)carbamoyl)-1H-pyrazolo[3,4-d]pyrimidin-1-yl)pyrrolidine-1-carboxylate 20 mg of (R)-4-amino-1-(1-(tert-butyloxycarbonyl)pyrrolidin-3-yl)-1H-pyrazolo[3,4-d]pyrimidine-3-carboxylic acid of Synthetic Example 3 was suspended in 1 mL of THF, and 12 mg of CDI was added thereto at room temperature with stirring. The mixture was stirred overnight at room temperature, 24 mg of 5-phenylbenzo[d]oxazol-2-amine was added thereto, and then the mixture was ice-cooled. 172 μl of a 1.0 M THF solution of lithium hexamethyldisilazane was added dropwise thereto. After the mixture was stirred for 1 hour, the reaction was terminated by adding 30 μl of acetic acid thereto. After the solvent was removed, the residue was purified by reverse phase preparative HPLC purification (water/acetonitrile (0.1% formic acid)), and thus 12.8 mg of the title compound was obtained as a white solid. Physical property value: m/z [M+H]$^+$ 541.1

(Step 2) Synthesis of Example Compound 41

To 12.8 mg of (R)-tert-butyl-3-(4-amino-3-((5-phenylbenzo[d]oxazol-2-yl)carbamoyl)-1H-pyrazolo[3,4-d]pyrimidin-1-yl)pyrrolidine-1-carboxylate obtained in the above Step 1, 1.5 mL of 4 N hydrochloric acid/1,4-dioxane was added, and the mixture was stirred for 1 hour. Thereafter, the solvent was removed, and the system as azeotropically distilled with 1 mL of toluene. 1 mL of chloroform and 16 μl of triethylamine were added to the residue, and the mixture was stirred under ice cooling. 1.9 μl of acryloyl chloride was added to the solution, and the mixture was stirred for 1 hour. Subsequently, the reaction was terminated with a saturated aqueous solution of sodium bicarbonate, and extracted with chloroform. The organic layer was dried over sodium sulfate, and then a residue obtained after removal of the solvent was purified by reverse phase preparative HPLC purification (water/acetonitrile (0.1% formic acid)). Thus, 3.46 mg of the title compound was obtained as a white solid.

Example 42 Synthesis of (R,E)-4-amino-N-(5-phenylbenzo[d]oxazol-2-yl)-1-(1-(4-(dimethylamino)but-2-enoyl)pyrrolidin-3-yl)-1H-pyrazolo[3,4-d]pyrimidine-3-carboxamide (Example Compound 42)

To 5 mg of (R)-tert-butyl-3-(4-amino-3-((5-phenylbenzo[d]oxazol-2-yl)carbamoyl)-1H-pyrazolo[3,4-d]pyrimidin-1-yl)pyrrolidine-1-carboxylate obtained in Step 1 of Example 41, 1 mL of 4N hydrochloric acid/1,4-dioxane was added, and the mixture was stirred for 30 minutes. Thereafter, the solvent was removed, and the residue was azeotropically distilled with 1 mL of toluene. The residue was dissolved in 1 mL of DMF, and 7.9 μL of DIPEA, 2.2 mg of (E)-4-(dimethylamino)but-2-enoic acid hydrochloride, and 5.18 mg of HATU were added thereto. The mixture was stirred for 1 hour at room temperature, and then the solution was concentrated under reduced pressure. The residue was purified by reverse phase preparative HPLC purification (water/acetonitrile (0.1% formic acid)). Thus, 3.04 mg of the title compound was obtained as a white solid.

Example 43 Synthesis of (R)-1-(1-acryloylpyrrolidin-3-yl)-4-amino-N-(5-(trifluoromethyl)benzo[d]oxazol-2-yl)-1H-pyrazolo[3,4-d]pyrimidine-3-carboxamide (Example Compound 43)

(Step 1) Synthesis of (R)-tert-butyl-3-(4-amino-3-((5-(trifluoromethyl)benzo[d]oxazol-2-yl)carbamoyl)-1H-pyrazolo[3,4-d]pyrimidin-1-yl)pyrrolidine-1-carboxylate 32 mg of (R)-4-amino-1-(1-(tert-butyloxycarbonyl)pyrrolidin-3-yl)-1H-pyrazolo[3,4-d]pyrimidine-3-carboxylic acid of Synthetic Example 3 was suspended in 2 mL of THF, and 55 mg of CDI was added thereto at room temperature with stirring. The mixture was stirred overnight at room temperature, and 28 mg of 5-(trifluoromethyl)benzo[d]oxazol-2-amine was added thereto. Subsequently, the mixture was ice-cooled, and 183 μl of a 1.0 M THF solution of lithium hexamethyldisilazane was added dropwise thereto. After the mixture was stirred for 1 hour, a solid obtained by adding water thereto was collected by filtration. The solid was washed with a mixed solvent of hexane/ethyl acetate, and thus 35 mg of the title compound was obtained as a pale yellow solid. Physical property value: m/z [M+H]$^+$ 533.3

(Step 2) Synthesis of Compound of Example 43

500 μl of dichloromethane was added to 8 mg of (R)-tert-butyl-3-(4-amino-3-((5-(trifluoromethyl)benzo[d]oxazol-2-yl)carbamoyl)-1H-pyrazolo[3,4-d]pyrimidin-1-yl)pyrrolidine-1-carboxylate obtained in the above Step 1, and 200 μl of trifluoroacetic acid was added thereto. The mixture was stirred for 30 minutes. Thereafter, the solvent was removed, and the residue was azeotropically distilled with 1 mL of toluene. 2 mL of chloroform and 11 μl of triethylamine were added to the residue, and the mixture was stirred under ice cooling. 1.2 μl of acryloyl chloride was added to the solution, and the mixture was stirred for 1 hour. Subsequently, the reaction was terminated with a saturated aqueous solution of sodium bicarbonate, and extracted with chloroform. The organic layer was dried over sodium sulfate, and then a residue obtained after removal of the solvent was purified by reverse phase preparative HPLC purification (water/acetonitrile (0.1% formic acid)). Thus, 1.58 mg of the title compound was obtained as a white solid.

Example 44 Synthesis of (R,E)-4-amino-N-(5-(trifluoromethyl)benzo[d]oxazol-2-yl)-1-(1-(4-(dimethylamino)but-2-enoyl)pyrrolidin-3-yl)-1H-pyrazolo[3,4-d]pyrimidine-3-carboxamide (Example Compound 44)

Example 43 To 5 mg of (R)-tert-butyl-3-(4-amino-3-((5-(trifluoromethyl)benzo[d]oxazol-2-yl)carbamoyl)-1H-pyrazolo[3,4-d]pyrimidin-1-yl)pyrrolidine-1-carboxylate obtained in Step 1, 500 μl of dichloromethane was added, and 200 μl of trifluoroacetic acid was further added thereto. The mixture was stirred for 30 minutes. Thereafter, the solvent was removed, and the residue was azeotropically distilled with 1 mL of toluene. The residue was dissolved in 1 mL of DMF, and 6.5 μl of DIPEA, 1.9 mg of (E)-4-(dimethylamino)but-2-enoic acid hydrochloride, and 4.3 mg of HATU were added thereto. The mixture was stirred for 1 hour at room temperature, and then the solution was concentrated under reduced pressure. The residue was purified by reverse phase preparative HPLC purification (water/acetonitrile (0.1% formic acid)), and thus 2.88 mg of the title compound was obtained as a white solid.

Example 45 Synthesis of 1-(1-acryloylazetidin-3-yl)-4-amino-N-(5-chlorobenzo[d]oxazol-2-yl)-1H-pyrazolo[3,4-d]pyrimidine-3-carboxamide (Example Compound 45)

(Step 1) Synthesis of tert-butyl 3-(4-amino-3-iodo-1H-pyrazolo[3,4-d]pyrimidin-1-yl)piperidine-1-carboxylate 240 mg of tert-butyl 3-hydroxyazetidine-1-carboxylate was dissolved in 2 mL of chloroform, and 290 μl of triethylamine and 130 μl of methanesulfonyl chloride were added thereto at 0° C. After the mixture was stirred for 1 hour under ice cooling, chloroform and water were added thereto, and an organic layer was separated. The organic layer was washed with a saturated solution of sodium hydrogen carbonate and water and then dried over anhydrous sodium sulfate, and the solvent was distilled off under reduced pressure. 300 mg of 3-iodo-1H-pyrazolo[3,4-d]pyrimidin-4-amine synthesized by the method described in WO 2007/126841, 570 mg of potassium carbonate, and 3 mL of DMA were added to the residue, and the mixture was heated to 100° C. and stirred for 11 hours. The mixture was cooled to room temperature, and was extracted with ethyl acetate. The organic layer was washed with water and dried over anhydrous magnesium sulfate. The residue was purified by amine gel chromatography (hexane/ethyl acetate=1:1 to 0:1), and thus 232 mg of the title compound was obtained as a pale yellow solid. Physical property value: m/z [M+H]$^+$ 417.1

(Step 2) Synthesis of 4-amino-1-(1-(tert-butyloxycarbonyl)azetidin-3-yl)-1H-pyrazolo[3,4-d]pyrimidine-3-carboxylic acid 262 mg of tert-butyl 3-(4-amino-3-iodo-1H-pyrazolo[3,4-d]pyrimidin-1-yl)piperidine-1-carboxylate obtained in Step 1 was dissolved in 10 mL of methanol and 1 mL of triethylamine. After the atmosphere was replaced with carbon monoxide, 51 mg of 1,1'-bis(diphenylphosphino)ferrocene-palladium(II) dichloride-dichloromethane was added thereto, and the mixture was heated at 80° C. for 14 hours. After the mixture was cooled, the solvent was removed from the solution, 1 mL of 1,4-dioxane was added to the residue, and 500 μL of a 5 N aqueous solution of sodium hydroxide was further added thereto. The mixture was stirred for 3 hours at room temperature, and then the mixture was adjusted to pH 4 with 2 N hydrochloric acid. The mixture was ice-cooled, and a solid precipitated by adding water thereto was collected by filtration and dried. Thus, 42 mg of the title compound was obtained as a pale brown solid.

Physical property value: m/z [M+H]$^+$ 335.2

(Step 3) Synthesis of tert-butyl-3-(4-amino-3-((5-chlorobenzo[d]oxazol-2-yl)carbamoyl)-1H-pyrazolo[3,4-d]pyrimidin-1-yl)azetidine-1-carboxylate 42 mg of 4-amino-1-(1-(tert-butyloxycarbonyl)azetidin-3-yl)-1H-pyrazolo[3,4-d]pyrimidine-3-carboxylic acid obtained in the above Step 2 was dissolved in 3 mL of DMF, 24 mg of CDI was added thereto, and the mixture was stirred overnight at room temperature. 4 mg of CDI was further added thereto, and the mixture was stirred for 30 minutes. 42 mg of 5-chlorobenzo[d]oxazol-2-amine was added to the solution, the mixture was ice-cooled, and 10 mg of sodium hydride (60%) was added thereto. After the mixture was stirred for 1 hour, the reaction was terminated with water, and the solvent was removed. The residue was purified by reverse phase preparative HPLC purification (water/acetonitrile (0.1% formic acid)), and thus 34 mg of the title compound was obtained as a white solid. Physical property value: m/z [M+H]$^+$ 485.2

(Step 4) Synthesis of Example Compound 45

To 10 mg of tert-butyl-3-(4-amino-3-((5-chlorobenzo[d]oxazol-2-yl)carbamoyl)-1H-pyrazolo[3,4-d]pyrimidin-1-yl)azetidine-1-carboxylate obtained in the above Step 3, 1 mL of 4 N hydrochloric acid/1,4-dioxane was added, and the mixture was stirred for 1 hour. Thereafter, the solvent was removed, and the residue was azeotropically distilled with 1 mL of toluene. 1 mL of chloroform and 14 μl of triethylamine were added to the residue, and the mixture was stirred under ice cooling. 1.7 μl of acryloyl chloride was added to the solution, and the mixture was stirred for 1 hour. Subsequently, the reaction was terminated with a saturated aqueous solution of sodium bicarbonate, and extracted with chloroform. The organic layer was dried over sodium sulfate, and then a residue obtained after removal of the solvent was purified by reverse phase preparative HPLC purification (water/acetonitrile (0.1% formic acid)). Thus, 0.69 mg of the title compound was obtained as a white solid.

Example 46 Synthesis of 7-(1-acryloylazetidin-3-yl)-4-amino-N-(5-chlorobenzo[d]oxazol-2-yl)-7H-pyrrolo[2,3-d]pyrimidine-5-carboxamide (Example Compound 46)

(Step 1) Synthesis of tert-butyl 3-(4-chloro-5-iodo-7H-pyrrolo[2,3-d]pyrimidin-7-yl)azetidine-1-carboxylate

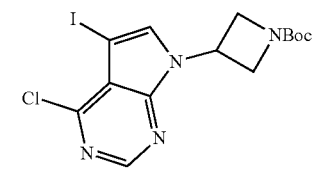 [SMILES: CC(C)(C)OC(=O)N1CC(n2cc(I)c3c(Cl)ncnc32)C1]

2.3 mL of DEAD was added to 80 mL of a THF solution of 2.00 g of 4-chloro-5-iodo-7H-pyrrolo[2,3-d]pyrimidine, 1.86 g of N-Boc-3-hydroxyazetidine and 3.75 g of triphenylphosphine, and the reaction liquid was stirred for 1 hour. The reaction liquid was concentrated and washed with ethyl acetate, and thus 2.55 g of the title compound as a white solid was obtained.

Physical property value: m/z [M+H]+ 435.0

(Step 2) Synthesis of tert-butyl 3-(4-amino-5-iodo-7H-pyrrolo[2,3-d]pyrimidin-7-yl)azetidine-1-carboxylate

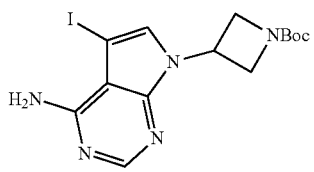 [SMILES: CC(C)(C)OC(=O)N1CC(n2cc(I)c3c(N)ncnc32)C1]

To 1.5 g of tert-butyl 3-(4-chloro-5-iodo-7H-pyrrolo[2,3-d]pyrimidin-7-yl)azetidine-1-carboxylate obtained in the above Step 1, 6 mL of THF and 6 mL of 28% aqueous ammonia were added, and the reaction liquid was stirred for 1.5 hours at 100° C. in a microwave reaction apparatus. Chloroform and water were added thereto, and an organic layer was separated. The organic layer was dried over anhydrous sodium sulfate, and the solvent was distilled off under reduced pressure. Thus, 1.5 g of the title compound as a white solid was obtained.

Physical property value: m/z [M+H]+ 416.0

(Step 3) Synthesis of tert-butyl 3-(4-amino-5-((5-chlorobenzo[d]oxazol-2-yl)carbamoyl)-7H-pyrrolo[2,3-d]pyrimidin-7-yl)azetidine-1-carboxylate 32 mg of tert-butyl 3-(4-amino-5-iodo-7H-pyrrolo[2,3-d]pyrimidin-7-yl)azetidine-1-carboxylate obtained in the above Step 2, 20 mg of 5-chlorobenzo[d]oxazol-2-amine, and 28 μl of diazabicycloundecene were dissolved in 1 mL of DMF, and 9 mg of 1,1'-bis(diphenylphosphino)ferrocene-palladium(II) dichloride-dichloromethane was further added thereto. The mixture was stirred for 1.5 hours at 80° C. under a carbon monoxide atmosphere. The mixture was partitioned with chloroform and water, and the organic layer was dried over sodium sulfate. Subsequently, a residue obtained after removal of the solvent was purified by silica gel chromatography (eluent:hexane/ethyl acetate=1/1→ethyl acetate/methanol=10/1), and thus 20 mg of the title compound was obtained as a pale brown solid. Physical property value: m/z [M+H]+ 484.2

(Step 4) Synthesis of Example Compound 46

To 5 mg of tert-butyl 3-(4-amino-5-((5-chlorobenzo[d]oxazol-2-yl)carbamoyl)-7H-pyrrolo[2,3-d]pyrimidin-7-yl)azetidine-1-carboxylate obtained in the above Step 3, 1 mL of 4 N hydrochloric acid/1,4-dioxane was added, and the mixture was stirred for 1 hour. Thereafter, the solvent was removed, and the residue was azeotropically distilled with 1 mL of toluene. 1 mL of chloroform and 14 μl of triethylamine were added to the residue, and the mixture was stirred under ice cooling. 1.7 μl of acryloyl chloride was added to the solution, and the mixture was stirred for 1 hour. Subsequently, the reaction was terminated with a saturated aqueous solution of sodium bicarbonate, and extracted with chloroform. The organic layer was dried over sodium sulfate, and then a residue obtained after removal of the solvent was purified by reverse phase preparative HPLC purification (water/acetonitrile (0.1% formic acid)). Thus, 2.21 mg of the title compound was obtained as a white solid.

Example 47 Synthesis of (E)-4-amino-N-(5-chlorobenzo[d]oxazol-2-yl)-7-(1-(4-(dimethylamino)but-2-enoyl)azetidin-3-yl) 7H-pyrrolo[2,3-d]pyrimidine-5-carboxamide (Example Compound 47)

To 5 mg of tert-butyl 3-(4-amino-5-((5-chlorobenzo[d]oxazol-2-yl)carbamoyl)-7H-pyrrolo[2,3-d]pyrimidin-7-yl)azetidine-1-carboxylate obtained in Step 3 of Example 46, 1 mL of 4 N hydrochloric acid/1,4-dioxane was added, and the mixture was stirred for 1 hour. Thereafter, the solvent was removed, and the residue was azeotropically distilled with 1 mL of toluene. The residue was dissolved in 1 mL of DMF, 14.4 μl of DIPEA, 4.1 mg of (E)-4-(dimethylamino)but-2-enoic acid hydrochloride and 9.4 mg of HATU were added thereto. After the mixture was stirred for 1 hour at room temperature, the solution was concentrated under reduced pressure. The residue was purified by reverse phase preparative HPLC purification (water/acetonitrile (0.1% formic acid)), and thus 4.67 mg of the title compound was obtained.

Example 48 Synthesis of (R)-7-(1-acryloylpyrrolidin-3-yl)-4-amino-N-(5-chlorobenzo[d]oxazol-2-yl)-7H-pyrrolo[2,3-d]pyrimidine-5-carboxamide (Example Compound 48)

(Step 1) Synthesis of (R)-tert-butyl 3-(4-chloro-5-iodo-7H-pyrrolo[2,3-d]pyrimidin-7-yl)pyrrolidine-1-carboxylate 5.00 g of 4-chloro-5-iodo-7H-pyrrolo[2,3-d]pyrimidine synthesized by the method described in WO 2005/042556, 19.1 g of (S)-tert-butyl 3-(methylsulfonyloxy)pyrrolidine-1-carboxylate, and 23.5 g of cesium carbonate were suspended in 25 mL of acetonitrile, and the mixture was heated for 3 hours at 60° C. After the suspension was cooled, water and methanol were added thereto, and a solid thus obtained was collected by filtration and dried. Thus, 5.65 g of the title compound was obtained as a pale brown solid.

(Step 2) (R)-tert-butyl 3-(4-amino-5-iodo-7H-pyrrolo[2,3-d]pyrimidin-7-yl)pyrrolidine-1-carboxylate To 5 g of (R)-tert-butyl 3-(4-chloro-5-iodo-7H-pyrrolo[2,3-d]pyrimidin-7-yl)pyrrolidine-1-carboxylate obtained in the above Step 1, 40 mL of 28% aqueous ammonia was added, and the reaction liquid was stirred for 1.5 hours at 100° C. in a microwave reaction apparatus. The mixture was stirred for 1 hour under ice cooling, and a solid precipitated therefrom was collected by filtration and washed with cold methanol. Thus, 3.91 g of the title compound was obtained as a white solid.

(Step 3) Synthesis of (R)-tert-butyl 3-(4-amino-5-((5-chlorobenzo[d]oxazol-2-yl)carbamoyl)-7H-pyrrolo[2,3-d]pyrimidin-7-yl)pyrrolidine-1-carboxylate 93 mg of tert-butyl 3-(4-amino-5-iodo-7H-pyrrolo[2,3-d]pyrimidin-7-yl)pyrrolidine-1-carboxylate obtained in the above Step 2, 110 mg of 5-chlorobenzo[d]oxazol-2-amine, and 100 μl of diazabicycloundecene were dissolved in 2 mL of DMF, and 35 mg of 1,1'-bis(diphenylphosphino)ferrocene-palladium(II) dichloride-dichloromethane was added thereto. The mixture was stirred for 2.5 hours at 80° C. under a carbon monoxide atmosphere. The mixture was partitioned with chloroform and water, and the organic layer was dried over sodium sulfate. Subsequently, a residue obtained after removal of the solvent was purified by silica gel chromatography (eluent:hexane/ethyl acetate=1/1→ethyl acetate/methanol=10/1), and thus 106 mg of the title compound was obtained as a pale brown solid. Physical property value: m/z [M+H]$^+$ 498.1

(Step 4) Synthesis of Example Compound 48

To 20 mg of (R)-tert-butyl 3-(4-amino-5-((5-chlorobenzo[d]oxazol-2-yl)carbamoyl)-7H-pyrrolo[2,3-d]pyrimidin-7-yl)pyrrolidine-1-carboxylate obtained in the above Step 3, 1 mL of 4 N hydrochloric acid/1,4-dioxane was added, and the mixture was stirred for 1 hour. Thereafter, the solvent was removed, and the residue was azeotropically distilled with 1 mL of toluene. 2 mL of chloroform and 28 μl of triethylamine were added to the residue, and the mixture was stirred under ice cooling. 3.2 μl of acryloyl chloride was added to the solution, and the mixture was stirred for 1 hour. Subsequently, the reaction was terminated with a saturated aqueous solution of sodium bicarbonate, and extracted with chloroform. The organic layer was dried over sodium sulfate, and then a residue obtained after removal of the solvent was purified by reverse phase preparative HPLC purification (water/acetonitrile (0.1% formic acid)). Thus, 3.52 mg of the title compound was obtained as a white solid.

Example 49 Synthesis of (R,E)-4-amino-N-(5-chlorobenzo[d]oxazol-2-yl)-7-(1-(4-(dimethylamino)but-2-enoyl)pyrrolidin-3-yl) 7H-pyrrolo[2,3-d]pyrimidine-5-carboxamide (Example Compound 49)

To 13 mg of (R)-tert-butyl 3-(4-amino-5-((5-chlorobenzo[d]oxazol-2-yl)carbamoyl)-7H-pyrrolo[2,3-d]pyrimidin-7-yl)pyrrolidine-1-carboxylate obtained in Step 3 of Example 48, 1 mL of 4 N hydrochloric acid/1,4-dioxane was added, and the mixture was stirred for 1 hour. Thereafter, the solvent was removed, and the residue was azeotropically distilled with 1 mL of toluene. The residue was dissolved in 1 mL of DMF, and 14.4 μl of DIPEA, 4.1 mg of (E)-4-(dimethylamino)but-2-enoic acid hydrochloride and 9.6 mg of HATU were added thereto. The mixture was stirred for 1 hour at room temperature, and then the solution was concentrated under reduced pressure. The residue was purified by reverse phase preparative HPLC purification (water/acetonitrile (0.1% formic acid)), and thus 6.66 mg of the title compound was obtained.

Example 50 Synthesis of (R,E)-4-amino-N-(5-chlorobenzo[d]oxazol-2-yl)-7-(1-(4-(ethyl(methyl)amino)but-2-enoyl)pyrrolidin-3-yl) 7H-pyrrolo[2,3-d]pyrimidine-5-carboxamide (Example Compound 50)

The title compound was obtained as a white solid according to the procedure described in Example 49, by using (E)-4-(ethyl(methyl)amino)but-2-enoic acid hydrochloride instead of (E)-4-(dimethylamino)but-2-enoic acid hydrochloride.

Example 51 Synthesis of (R,E)-4-amino-N-(5-chlorobenzo[d]oxazol-2-yl)-7-(1-(4-(diethylamino)but-2-enoyl)pyrrolidin-3-yl) 7H-pyrrolo[2,3-d]pyrimidine-5-carboxamide (Example Compound 51)

The title compound was obtained as a white solid according to the procedure described in Example 49, using (E)-4-(diethylamino)but-2-enoic acid hydrochloride instead of (E)-4-(dimethylamino)but-2-enoic acid hydrochloride.

Example 52 Synthesis of (R,E)-4-amino-N-(5-chlorobenzo[d]oxazol-2-yl)-7-(1-(4-(isopropyl(methyl)amino)but-2-enoyl)pyrrolidin-3-yl) 7H-pyrrolo[2,3-d]pyrimidine-5-carboxamide (Example Compound 52)

The title compound was obtained as a white solid according to the procedure described in Example 49, by using (E)-4-(isopropyl(methyl)amino)but-2-enoic acid hydrochloride instead of (E)-4-(dimethylamino)but-2-enoic acid hydrochloride.

Example 53 Synthesis of (R,E)-4-amino-N-(5-chlorobenzo[d]oxazol-2-yl)-7-(1-(4-(pyrrolidin-1-yl)but-2-enoyl)pyrrolidin-3-yl) 7H-pyrrolo[2,3-d]pyrimidine-5-carboxamide (Example Compound 53)

The title compound was obtained as a white solid according to the procedure described in Example 49, by using (E)-4-(pyrrolidin-1-yl)but-2-enoic acid hydrochloride instead of (E)-4-(dimethylamino)but-2-enoic acid hydrochloride.

Example 54 Synthesis of (R,E)-4-amino-N-(5-chlorobenzo[d]oxazol-2-yl)-7-(1-(4-(piperidin-1-yl)but-2-enoyl)pyrrolidin-3-yl) 7H-pyrrolo[2,3-d]pyrimidine-5-carboxamide (Example Compound 54)

The title compound was obtained as a white solid according to the procedure described in Example 49, by using (E)-4-(piperidin-1-yl)but-2-enoic acid hydrochloride instead of (E)-4-(dimethylamino)but-2-enoic acid hydrochloride.

Example 55 Synthesis of (R)-7-(1-acryloylpyrrolidin-3-yl)-4-amino-N-(5-phenylbenzo[d]oxazol-2-yl)-7H-pyrrolo[2,3-d]pyrimidine-5-carboxamide (Example Compound 55)

(Step 1) Synthesis of (R)-tert-butyl 3-(4-amino-5-((5-phenylbenzo[d]oxazol-2-yl)carbamoyl)-7H-pyrrolo[2,3-d]pyrimidin-7-yl)pyrrolidine-1-carboxylate The title compound was obtained as a brown solid according to the procedure described in Step 3 of Example 48, by using 5-phenylbenzo[d]oxazol-2-amine instead of 5-chlorobenzo[d]oxazol-2-amine. Physical property value: m/z [M+H]$^+$ 540.3

(Step 2) Synthesis of Example Compound 55

The title compound was obtained as a white solid according to the procedure described in Step 4 of Example 48, by using (R)-tert-butyl 3-(4-amino-5-((5-phenylbenzo[d]oxazol-2-yl)carbamoyl)-7H-pyrrolo[2,3-d]pyrimidin-7-yl)pyrrolidine-1-carboxylate obtained in the above Step 1.

Example 56 Synthesis of (R,E)-4-amino-N-(5-phenylbenzo[d]oxazol-2-yl)-7-(1-(4-(dimethylamino)but-2-enoyl)pyrrolidin-3-yl) 7H-pyrrolo[2,3-d]pyrimidine-5-carboxamide (Example Compound 56)

To 13 mg of (R)-tert-butyl 3-(4-amino-5-((5-phenylbenzo[d]oxazol-2-yl)carbamoyl)-7H-pyrrolo[2,3-d]pyrimidin-7-yl)pyrrolidine-1-carboxylate obtained in Step 1 of Example 55, 1 mL of 4 N hydrochloric acid/1,4-dioxane was added, and the mixture was stirred for 1 hour. Thereafter, the solvent was removed, and the residue was azeotropically distilled with 1 mL of toluene. The residue was dissolved in 1 mL of DMF, and 14.4 µl of DIPEA, 4.1 mg of (E)-4-(dimethylamino)but-2-enoic acid hydrochloride, and 9.6 mg of HATU were added thereto. After the mixture was stirred for 1 hour at room temperature, the solution was concentrated under reduced pressure. The residue was purified by reverse phase preparative HPLC purification (water/acetonitrile (0.1% formic acid)), and thus 6.66 mg of the title compound was obtained.

Example 57 Synthesis of (R,E)-4-amino-N-(5-phenylbenzo[d]oxazol-2-yl)-7-(1-(4-(ethyl(methyl) amino)but-2-enoyl)pyrrolidin-3-yl) 7H-pyrrolo[2,3-d]pyrimidine-5-carboxamide (Example Compound 57)

The title compound was obtained as a white solid according to the procedure described in Example 56, by using (E)-4-(ethyl(methyl)amino)but-2-enoic acid hydrochloride instead of (E)-4-(dimethylamino)but-2-enoic acid hydrochloride.

Example 58 Synthesis of (R,E)-4-amino-N-(5-phenylbenzo[d]oxazol-2-yl)-7-(1-(4-(diethylamino)but-2-enoyl)pyrrolidin-3-yl) 7H-pyrrolo[2,3-d]pyrimidine-5-carboxamide (Example Compound 58)

The title compound was obtained as a white solid according to the procedure described in Example 56, by using (E)-4-(diethylamino)but-2-enoic acid hydrochloride instead of (E)-4-(dimethylamino)but-2-enoic acid hydrochloride.

Example 59 Synthesis of (R,E)-4-amino-N-(5-phenylbenzo[d]oxazol-2-yl)-7-(1-(4-(isopropyl(methyl) amino)but-2-enoyl)pyrrolidin-3-yl) 7H-pyrrolo[2,3-d]pyrimidine-5-carboxamide (Example Compound 59)

The title compound was obtained as a white solid according to the procedure described in Example 56, by using (E)-4-(isopropyl(methyl)amino)but-2-enoic acid hydrochloride instead of (E)-4-(dimethylamino)but-2-enoic acid hydrochloride.

Example 60 Synthesis of (R,E)-4-amino-N-(5-phenylbenzo[d]oxazol-2-yl)-7-(1-(4-(pyrrolidin-1-yl) but-2-enoyl)pyrrolidin-3-yl) 7H-pyrrolo[2,3-d]pyrimidine-5-carboxamide (Example Compound 60)

The title compound was obtained as a white solid according to the procedure described in Example 56, by using (E)-4-(pyrrolidin-1-yl)but-2-enoic acid hydrochloride instead of (E)-4-(dimethylamino)but-2-enoic acid hydrochloride.

Example 61 Synthesis of (R,E)-4-amino-N-(5-phenylbenzo[d]oxazol-2-yl)-7-(1-(4-(piperidin-1-yl)but-2-enoyl)pyrrolidin-3-yl) 7H-pyrrolo[2,3-d]pyrimidine-5-carboxamide (Example Compound 61)

The title compound was obtained as a white solid according to the procedure described in Example 56, by using (E)-4-(piperidin-1-yl)but-2-enoic acid hydrochloride instead of (E)-4-(dimethylamino)but-2-enoic acid hydrochloride.

Reference Example 1 Synthesis of (R)-1-(3-(4-amino-3-(4-phenoxyphenyl)-1H-pyrazolo[3,4-d] pyrimidin-1-yl)piperidin-1-yl)prop-2-en-1-one (Reference compound 1, PCI-32765)

The title compound was obtained as a white solid by synthesizing the compound according to the procedure described in the method of WO 2008/121742.

Hereinafter, the structural formulas and physical property values of Example Compounds 1 to 61 and Reference compound 1 are presented in Table 2 to Table 14.

TABLE 2

| Example No. | Structure | NMR | mass |
|---|---|---|---|
| 1 | 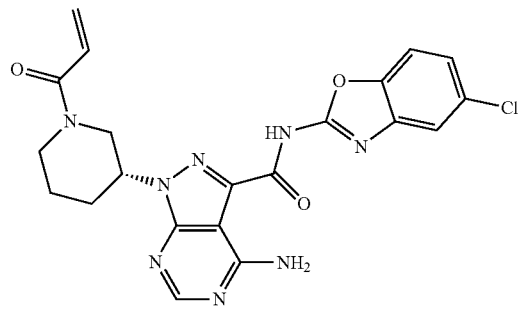 [SMILES: C=CC(=O)N1CCC[C@@H](n2nc(C(=O)Nc3nc4cc(Cl)ccc4o3)c3c(N)ncnc32)C1] | $^1$H NMR (400 MHz, DMSO-d$_6$) δ ppm 1.59 (br. s., 1 H) 1.95 (s, 1 H) 2.16 (br. s., 1 H) 2.32 (br. s., 1 H) 2.91 (br. s., 0.5 H) 4.11 (br. s., 0.5 H) 4.31 (br. s., 1 H) 4.57 (br. s., 1 H) 4.73 (br. s., 1 H) 5.65 (br. s., 1 H) 5.71 (br. s., 1 H) 6.08-6.18 (m, 1 H) 6.72-6.93 (m, 1 H) 6.76 (br. s., 1 H) 6.79 (s, 1 H) 6.84 (d, J = 12.44 Hz, 1 H) 7.36 (d, J = 7.56 Hz, 1 H) 7.70 (d, J = 15.12 Hz, 1 H) 8.16-8.36 (m, 3 H) | 469.1 |

TABLE 2-continued

| Example No. | Structure | NMR | mass |
|---|---|---|---|
| 2 | 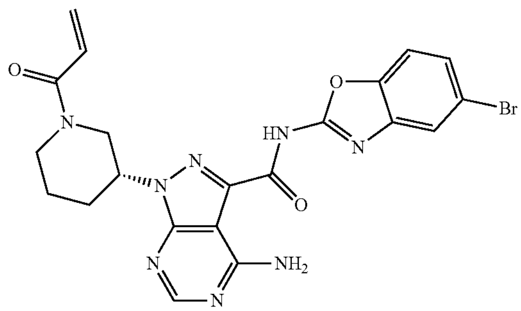 [SMILES: C=CC(=O)N1CCC[C@@H](n2nc(C(=O)Nc3nc4cc(Br)ccc4o3)c3c(N)ncnc32)C1] | $^1$H NMR (400 MHz, DMSO-d$_6$) δ ppm 1.44-1.68 (m, 1 H) 1.87 (d, J = 12.30 Hz, 1 H) 2.06 (br. s., 1 H) 2.22 (d, J = 9.57 Hz, 1 H) 3.05-3.32 (m, 1 H) 4.03-4.25 (m, 0.5 H) 4.29-4.46 (m, 1 H) 4.60 (d, J = 18.45 Hz, 0.5 H) 5.51-5.75 (m, 1 H) 6.09 (br. s., 1 H) 6.61-6.95 (m, 1 H) 7.12 (s, 1 H) 7.24 (br. s., 1 H) 7.85 (br. s., 1 H) 8.10 (br. s., 1 H) 8.29 (s, 2 H) 11.07 (br. s., 1 H) | 513.1 |
| 3 | 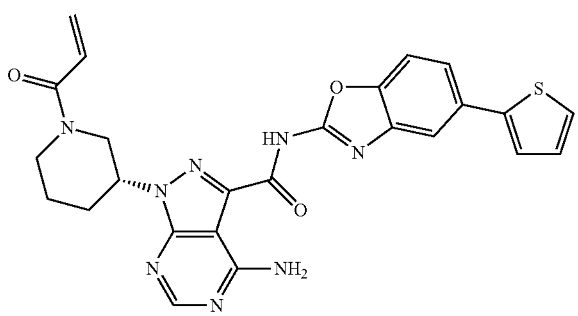 [SMILES: C=CC(=O)N1CCC[C@@H](n2nc(C(=O)Nc3nc4cc(-c5cccs5)ccc4o3)c3c(N)ncnc32)C1] | $^1$H NMR (400 MHz, DMSO-d$_6$) δ ppm 1.33-1.46 (m, 1 H) 1.52-1.70 (m, 1 H) 1.90-2.03 (m, 1 H) 2.10-2.25 (m, 1 H) 2.85-2.98 (m, 1 H) 3.69-3.85 (m, 1 H) 4.05-4.43 (m, 2 H) 4.51-4.86 (m, 2 H) 5.61-5.77 (m, 1 H) 6.05-6.22 (m, 1 H) 6.71-6.95 (m, 1 H) 7.17 (d, J = 4.63 Hz, 1 H) 7.58 (d, J = 4.88 Hz, 2 H) 7.62-7.69 (m, 1 H) 7.70-7.78 (m, 1 H) 7.83-8.00 (m, 1 H) 8.16-8.27 (m, 1 H) 8.27-8.37 (m, 1 H) 8.32 (s, 2 H) | 515.2 |
| 4 | 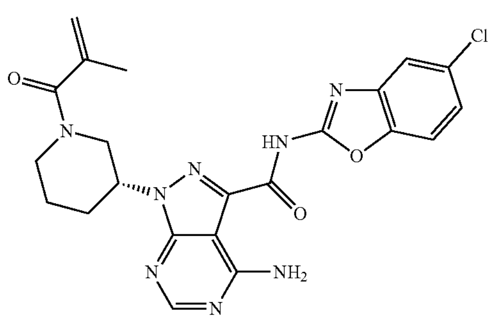 [SMILES: C=C(C)C(=O)N1CCC[C@@H](n2nc(C(=O)Nc3nc4cc(Cl)ccc4o3)c3c(N)ncnc32)C1] | $^1$H NMR (400 MHz, CHLOROFORM-d) δ ppm 1.73 (br. s., 1 H) 1.98 (br. s., 3 H) 2.27 (br. s., 2 H) 2.40 (d, J = 9.02 Hz, 1 H) 3.35-3.57 (m, 1 H) 3.64-4.14 (m, 2 H) 4.31 (br. s., 1 H) 4.94 (tt, J = 8.81, 4.24 Hz, 1 H) 5.09 (s, 1 H) 5.20 (br. s., 1 H) 6.58 (br. s., 1 H) 7.28-7.30 (m, 1 H) 7.45 (d, J = 8.78 Hz, 1 H) 7.68 (d, J = 1.95 Hz, 1 H) 8.34-8.42 (m, 2 H) 8.49 (br. s., 1 H) | 481.1 |
| 5 | 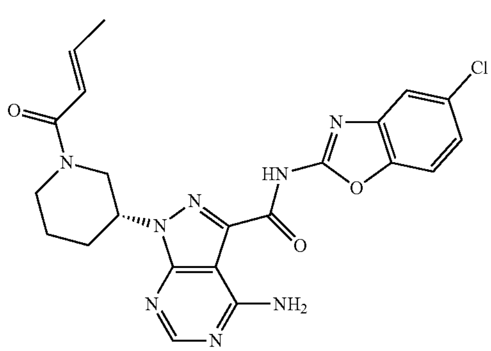 [SMILES: C/C=C/C(=O)N1CCC[C@@H](n2nc(C(=O)Nc3nc4cc(Cl)ccc4o3)c3c(N)ncnc32)C1] | $^1$H NMR (400 MHz, DMSO-d$_6$) δ ppm 1.51 (br. s., 1 H) 1.75 (br. s., 1 H) 1.82 (br. s., 1 H) 2.05 (br. s., 1 H) 2.20 (d, J = 9.57 Hz, 1 H) 3.47 (s, 3 H) 4.09 (br. s., 3 H) 4.56 (br. s., 2 H) 6.37-6.74 (m, 1 H) 7.00 (d, J = 8.20 Hz, 1 H) 7.31 (d, J = 8.20 Hz, 1 H) 7.40 (s, 1 H) 7.79 (d, J = 4.10 Hz, 1 H) 8.09 (br. s., 1 H) 8.16 (s, 2 H) 10.89 (br. s., 2 H) | 481.2 |

TABLE 3

| | | | |
|---|---|---|---|
| 6 | 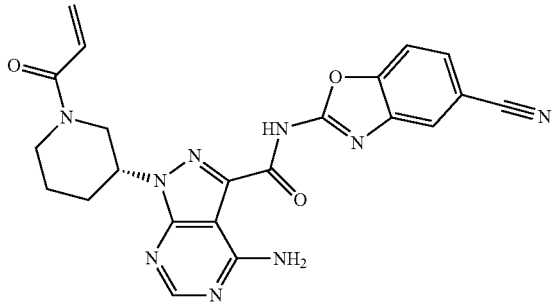 [SMILES: C=CC(=O)N1CCC[C@@H](n2nc(C(=O)Nc3nc4cc(C#N)ccc4o3)c3c(N)ncnc32)C1] | ¹H NMR (400 MHz, DMSO-d6) d ppm 1.21-1.28 (m, 1 H) 1.63 (d, J = 12.93 Hz, 1 H) 1.00-1.98 (m, 1 H) 2.18 (br. s., 1 H) 2.27-2.44 (m, 1 H) 2.82-2.95 (m, 0.5 H) 3.17 (br. s., 0.5 H) 3.66-3.82 (m, 0.5 H) 4.13 (d, J = 12.68 Hz, 0.5 H) 4.32 (d, J = 15.37 Hz, 1 H) 4.62 (d, J = 11.95 Hz, 0.5 H) 4.74 (br. s., 1 H) 5.62-5.75 (m, 1 H) 6.09-6.24 (m, 1 H) 6.89 (dd, J = 16.59, 10.49 Hz, 1 H) 7.83 (dd, J = 8.41, 1.59 Hz, 1 H) 7.93 (d, J = 8.54 Hz, 1 H) 8.09-8.34 (m, 3 H) 12.24-12.68 (m, 1 H) | 459.2 |
| 7 | 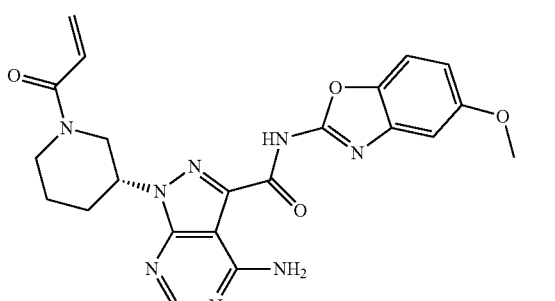 | ¹H NMR (400 MHz, DMSO-d$_6$) δ ppm 1.49-1.74 (m, 1 H) 1.81-2.00 (m, 2 H) 2.09-2.40 (m, 2 H) 2.80-2.96 (m, 0.5 H) 3.07-3.23 (m, 0.5 H) 3.29-3.37 (m, 1 H) 3.69-3.84 (m, 4 H) 4.00-4.21 (m, 0.5 H) 4.21-4.43 (m, 1 H) 4.52-4.67 (m, 0.5 H) 4.64-4.84 (m, 1 H) 5.57-5.78 (m, 1 H) 6.04-6.24 (m, 1 H) 6.66-7.02 (m, 1 H) 7.74-7.96 (m, 1 H) 8.10-8.37 (m, 3 H) 12.37-12.62 (m, 1 H) | 464.0 |
| 8 | 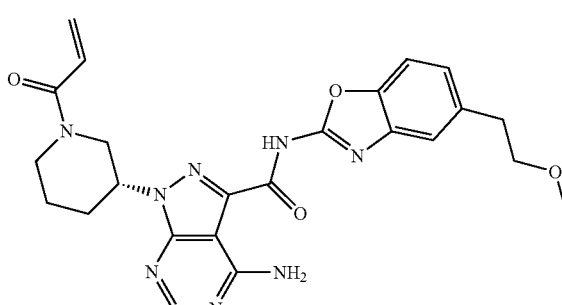 | ¹H NMR (400 MHz, DMSO-d$_6$)δ ppm 1.49-1.75 (m, 1 H) 1.85-2.00 (m, 1 H) 2.08-2.24 (m, 1 H) 2.24-2.42 (m, 1 H) 2.92 (s, 2 H) 2.92 (t, J = 13.20 Hz, 2 H) 3.25 (s, 3 H) 3.24-3.27 (m, 1 H) 3.51-3.61 (m, 2 H) 3.92-4.46 (m, 3 H) 4.50-4.90 (m, 2 H) 5.54-5.81 (m, 1 H) 6.02-6.24 (m, 1 H) 6.64-6.98 (m, 2 H) 7.14-7.29 (m, 1 H) 7.41-7.69 (m, 1 H) 8.11-8.45 (m, 3 H) | 492.2 |
| 9 | 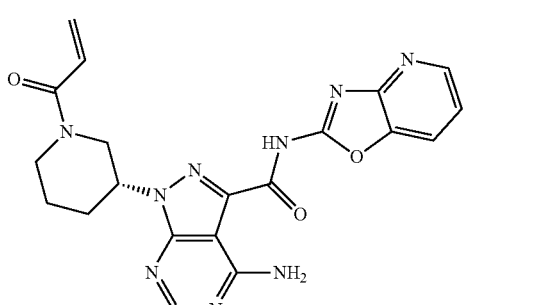 | ¹H NMR (400 MHz, DMSO-d$_6$) δppm 1.49-1.67 (m, 1 H) 1.86-2.13 (m, 2 H) 2.21-2.34 (m, 1 H) 2.74-2.86 (m, 0.5 H) 3.07-3.21 (m, 0.5 H) 3.55-3.67 (m, 0.5 H) 4.01-4.30 (m, 0.5 H) 4.37-4.49 (m, 1 H) 4.52-4.74 (m, 2 H) 5.59-5.76 (m, 1 H) 6.03-6.20 (m, 1 H) 6.73-6.94 (m, 1 H) 6.95-7.04 (m, 1 H) 7.59-7.68 (m, 1 H) 7.88 (br. s., 1 H) 8.10-8.15 (m, 2 H) 10.81-10.89 (m, 1 H) | 434.3 |
| 10 | 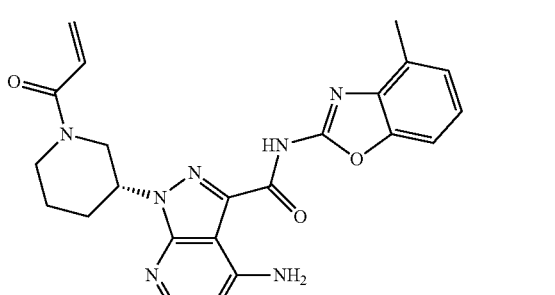 | ¹H NMR (400 MHz, DMSO-d$_6$) δ ppm 1.57 (br. s., 1 H) 1.83-1.98 (m, 1 H) 2.14 (br. s., 1 H) 2.23-2.38 (m, 1 H) 2.50 (s, 3H) 2.87 (br. s., 0.5 H) 3.71 (br. s., 0.5 H) 4.06 (br. s., 0.5 H) 4.28 (br. s., 0.5 H) 4.54 (br. s., 1 H) 4.72 (br. s., 1 H) 5.62 (br. s., 1 H) 5.67 (br. s., 1 H) 6.09 (s, 1 H) 6.14 (s, 1 H) 6.73 (br. s., 1 H) 6.84 (br. s., 1 H) 7.12-7.24 (m, 2 H) 7.45 (d, J = 7.52 Hz, 2 H) 8.09-8.21 (m, 2 H) 8.22-8.30 (m, 2 H) | 447.2 |

TABLE 4
| | | | |
|---|---|---|---|
| 11 | 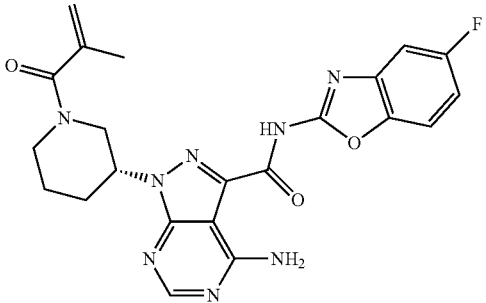 [SMILES: C=C(C)C(=O)N1CCC[C@@H](n2nc(C(=O)Nc3nc4cc(F)ccc4o3)c3c(N)ncnc32)C1] | ¹H NMR (400 MHz, DMSO-d₆) δ ppm 1.60 (d, J = 12.30 Hz, 1 H) 1.83 (br. s., 3 H) 1.90 (br. s., 1 H) 2.13 (d, J = 8.20 Hz, 1 H) 2.32 (d, J = 10.25 Hz, 1 H) 3.88 (br. s., 1 H) 4.10 (br. s., 1 H) 4.41 (br. s., 1 H) 4.75 (br. s., 1 H) 5.01 (br. s., 1 H) 5.13 (br. s., 1 H) 7.12-7.19 (m, 1 H) 7.49 (d, J = 6.83 Hz, 1 H) 7.68 (dd, J = 8.88, 4.10 Hz, 1 H) 8.19 (br. s., 1 H) 8.26 (s, 1 H) 12.27 (br. s., 1 H) | 466.2 |
| 12 | 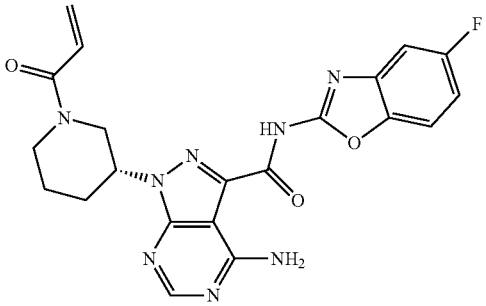 [SMILES: C=CC(=O)N1CCC[C@@H](n2nc(C(=O)Nc3nc4cc(F)ccc4o3)c3c(N)ncnc32)C1] | ¹H NMR (400 MHz, DMSO-d₆) δ ppm 1.50-1.69 (m, 1 H) 1.86-1.99 (m, 1 H) 2.09-2.26 (m, 1 H) 2.27-2.42 (m, 1 H) 2.84-2.97 (m, 0.5 H) 3.18 (t, J = 12.20 Hz, 0.5 H) 3.69-3.82 (m, 0.5 H) 4.11 (d, J = 13.17 Hz, 0.5 H) 4.22-4.39 (m, 1 H) 4.53-4.68 (m, 1 H) 4.72-4.76 (m, 0.5 H) 5.61-5.75 (m, 1 H) 6.07-6.19 (m, 1 H) 6.72-6.92 (m, 1 H) 7.20 (td, J = 9.39, 2.68 Hz, 1 H) 7.54 (d, J = 7.80 Hz, 1 H) 7.73 (dd, J = 8.78, 4.39 Hz, 1 H) 8.03-8.37 (m, 3 H) 12.29 (br. s., 1 H) | 451.2 |
| 13 | 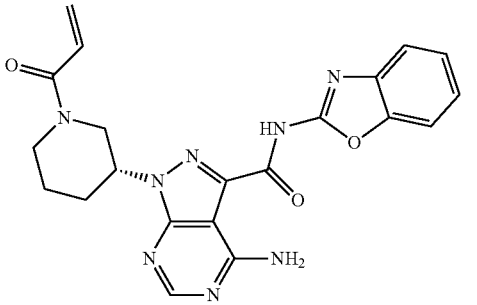 [SMILES: C=CC(=O)N1CCC[C@@H](n2nc(C(=O)Nc3nc4ccccc4o3)c3c(N)ncnc32)C1] | ¹H NMR (400 MHz, DMSO-d₆) δ ppm 1.52-1.69 (m, 1 H) 1.89-2.02 (m, 1 H) 2.09-2.25 (m, 1 H) 2.28-2.42 (m, 1 H) 2.83-2.98 (m, 0.5 H) 3.07-3.25 (m, 0.5 H) 3.23-3.37 (m, 0.5 H) 3.65-3.87 (m, 0.5 H) 4.06-4.17 (m, 0.5 H) 4.22-4.38 (m, 1 H) 4.56-4.65 (m, 0.5 H) 4.69-4.81 (m, 1 H) 5.55-5.81 (m, 1 H) 6.07-6.19 (m, 1 H) 6.73-6.92 (m, 1 H) 7.33-7.41 (m, 2 H) 7.59-7.76 (m, 2 H) 8.23 (br. s., 2 H) 8.30 (s, 1 H) 12.15 (br. s., 1 H) | 433.0 |
| 14 | 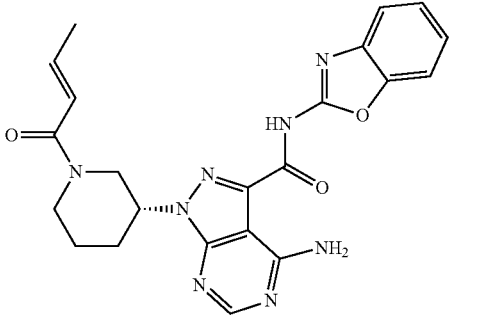 [SMILES: C/C=C/C(=O)N1CCC[C@@H](n2nc(C(=O)Nc3nc4ccccc4o3)c3c(N)ncnc32)C1] | ¹H NMR (400 MHz, DMSO-d₆) δ ppm 1.14-1.52 (m, 1 H) 1.63-1.80 (m, 1 H) 1.91-2.00 (m, 1 H) 2.03 (br. s., 3 H) 2.08-2.19 (m, 1 H) 2.97 (br. s., 1 H) 3.45 (br. s., 1 H) 3.78 (br. s., 2 H) 4.58 (br. s., 1 H) 4.72-4.97 (m, 1 H) 5.50-5.89 (m, 1 H) 6.54-6.83 (m, 1 H) 7.65-8.10 (m, 1 H) 8.15-8.29 (m, 1 H) | 446.3 |

TABLE 4-continued

| 15 | 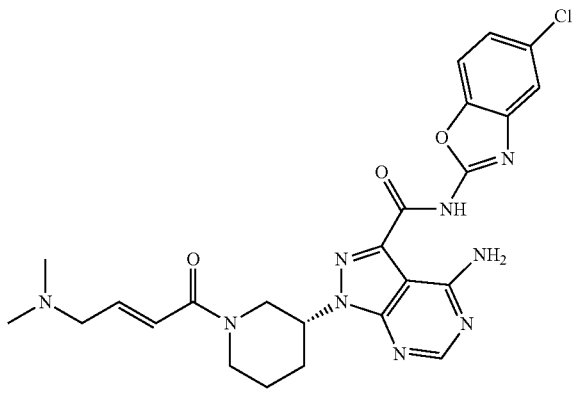 [SMILES: CN(C)C/C=C/C(=O)N1CCC[C@@H](n2nc(C(=O)Nc3nc4cc(Cl)ccc4o3)c3c(N)ncnc32)C1] | $^1$H NMR (400 MHz, DMSO-d$_6$) δ ppm 1.53 (br. s., 2 H) 1.88 (d, J = 12.98 Hz, 2 H) 2.09 (br. s., 3 H) 2.15 (br. s., 3 H) 2.84 (br. s., 1 H) 2.96 (br. s., 1 H) 3.05 (br. s., 2 H) 3.13 (br. s., 2 H) 4.05 (br. s., 2 H) 4.14 (br. s., 3 H) 4.26 (br. s., 4 H) 4.61 (br. s., 6 H) 6.53 (br. s., 2 H) 6.62 (br. s., 2 H) 7.01 (d, J = 8.20 Hz, 1 H) 7.32 (d, J = 8.20 Hz, 1 H) 7.44 (s, 1 H) 7.83 (br. s., 2 H) 8.09 (s, 1 H) 8.16 (s, 3 H) | 524.1 |

TABLE 5

| 16 | 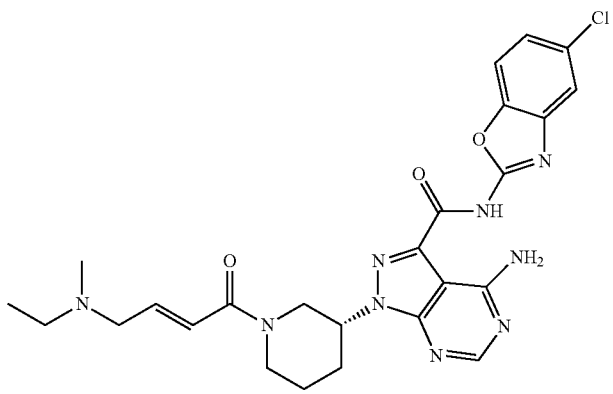 [SMILES: CCN(C)C/C=C/C(=O)N1CCC[C@@H](n2nc(C(=O)Nc3nc4cc(Cl)ccc4o3)c3c(N)ncnc32)C1] | $^1$H NMR (400 MHz, DMSO-d$_6$) δ ppm 0.91 (br. s., 3 H) 0.98 (br. s., 4 H) 1.54 (br. s., 2 H) 1.88 (d, J = 12.30 Hz, 1 H) 2.09 (br. s., 3 H) 2.21 (br. s., 3 H) 2.34 (s, 3 H) 2.37 (s, 3 H) 3.05 (br. s., 2 H) 3.98-4.73 (m, 6 H) 6.53 (br. s., 2 H) 6.63 (br. s., 2 H) 7.01 (dd, J = 8.20, 2.05 Hz, 1 H) 7.33 (d, J = 8.20 Hz, 1 H) 7.45 (s, 1 H) 7.83 (br. s., 1 H) 8.09 (s, 1 H) 8.15 (s, 2 H) 10.82 (br. s., 1 H) | 538.2 |
| 17 | 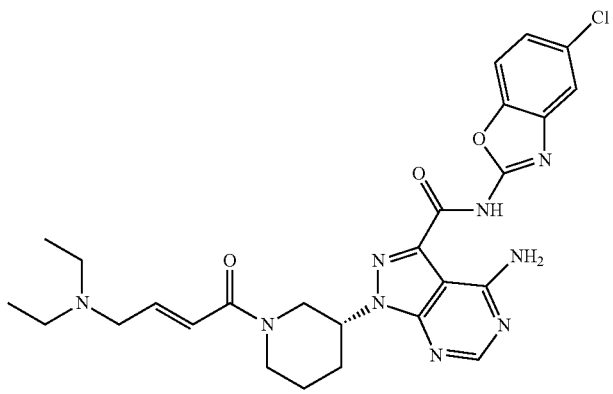 [SMILES: CCN(CC)C/C=C/C(=O)N1CCC[C@@H](n2nc(C(=O)Nc3nc4cc(Cl)ccc4o3)c3c(N)ncnc32)C1] | $^1$H NMR (400 MHz, DMSO-d$_6$) δ ppm 0.88 (br. s., 3 H) 0.95 (br. s., 3 H) 1.54 (br. s., 2 H) 1.89 (d, J = 11.62 Hz, 2 H) 2.06 (br. s., 2 H) 2.22 (br. s., 2 H) 2.63 (br. s., 1 H) 2.69 (br. s., 1 H) 4.10 (d, J = 15.72 Hz, 4 H) 4.26 (m, 3 H) 4.62 (m, 4 H) 6.56 (br. s., 2 H) 6.65 (br. s., 2 H) 7.01 (dd, J = 8.20, 2.05 Hz, 1 H) 7.33 (d, J = 8.20 Hz, 1 H) 7.45 (s, 1 H) 7.83 (d, J = 4.10 Hz, 2 H) 8.09 (s, 1 H) 8.15 (s, 2 H) 10.82 (br. s., 1 H) | 552.3 |

TABLE 5-continued
| 18 | 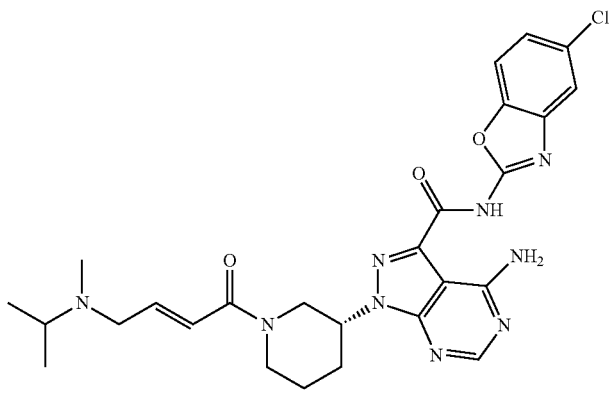 [SMILES: CC(C)N(C)C/C=C/C(=O)N1CCC[C@@H](n2nc(C(=O)Nc3nc4cc(Cl)ccc4o3)c3c(N)ncnc32)C1] | ¹H NMR (400 MHz, DMSO-d₆) δ ppm 0.91 (s, 5 H) 0.95 (s, 5 H) 1.19-1.26 (m, 1 H) 1.53 (br. s., 1 H) 1.87 (br. s., 1 H) 2.08 (bt. s., 4 H) 2.13 (br. s., 3 H) 2.20 (br. s., 2 H) 2.72-2.94 (m, 3 H) 4.00-4.32 (m, 2 H) 4.41-4.70 (m, 4 H) 6.48-6.72 (m, 3 H) 7.00-7.04 (m, 1 H) 7.33 (d, J = 8.20 Hz, 1 H) 7.45 (s, 1 H) 7.84 (br. s., 2 H) 8.09-8.18 (m, 2 H) 10.79 (br. s., 1 H) | 552.3 |
| 19 | 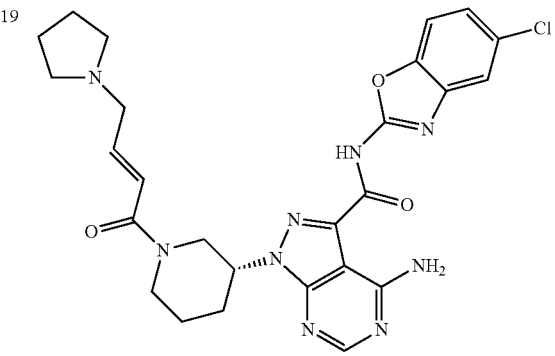 | ¹H NMR (400 MHz, DMSO-d₆) δ ppm 1.62 (br. s., 4 H) 1.67 (br. s., 3 H) 1.89 (d, J = 13.67 Hz, 2 H) 2.06 (br. s., 2 H) 2.22 (br. s., 2 H) 2.85 (br. s., 2 H) 3.13 (br. s., 2 H) 3.23 (br. s., 2 H) 3.97-4.33 (m, 4 H) 4.45-4.68 (m, 4 H) 6.53 (br. s., 1 H) 6.63 (br. s., 1 H) 7.01 (dd, J = 8.20, 2.05 Hz, 1 H) 7.32 (d, J = 8.20 Hz, 1 H) 7.45 (s, 1 H) 7.82 (d, J = 4.78 Hz, 1 H) 8.09 (s, 1 H) 8.18 (s, 2 H) 10.86 (br. s., 1 H) | 550.2 |
| 20 | 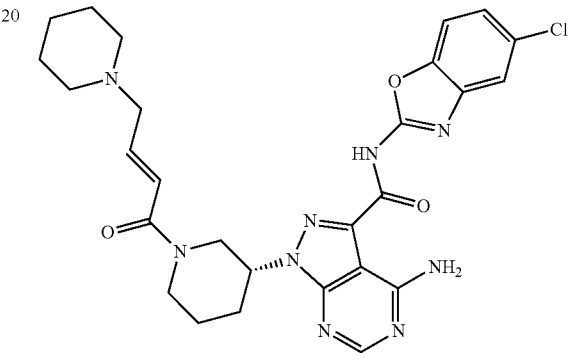 | ¹H NMR (400 MHz, DMSO-d₆) δ ppm 1.34 (br. s., 3 H) 1.40 (br. s., 3 H) 1.47 (br. s., 6 H) 1.88 (d, J = 13.67 Hz, 1 H) 2.05 (d, J = 8.20 Hz, 1 H) 2.25 (br. s., 4 H) 2.32 (br. s., 4 H) 2.85 (br. s., 1 H) 2.95 (br. s., 2 H) 4.00-4.37 (m, 4 H) 4.47-4.69 (m, 4 H) 6.50 (br. s., 1 H) 6.61 (br. s., 2 H) 7.01 (dd, J = 8.20, 2.05 Hz, 1 H) 7.32 (d, J = 8.20 Hz, 1 H) 7.45 (s, 1 H) 7.82 (d, J = 4.10 Hz, 1 H) 8.09 (s, 1 H) 8.17 (s, 2 H) 10.86 (br. s., 1 H) | 564.3 |

TABLE 6
| 21 | 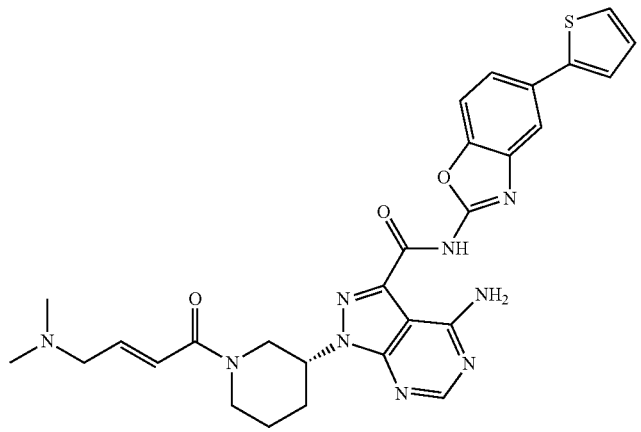 [SMILES: CN(C)C/C=C/C(=O)N1CCC[C@@H](n2nc(C(=O)Nc3nc4cc(-c5cccs5)ccc4o3)c3c(N)ncnc32)C1] | ¹H NMR (400 MHz, DMSO-d₆) δ ppm 1.46-1.64 (m, 1 H) 1.82-1.94 (m, 1 H) 2.00-2.10 (m, 4 H) 2.13 (br. s., 3 H) 2.17-2.27 (m, 1 H) 2.79-2.90 (m, 0.5 H) 3.06-3.12 (m, 0.5 H) 3.57-3.66 (m, 5 H) 3.99-4.35 (m, 4 H) 4.47-4.70 (m, 2 H) 6.48-6.68 (m, 2 H) 7.05-7.12 (m, 1 H) 7.29-7.40 (m, 2 H) 7.41-7.47 (m, 1 H) 7.68 (s, 1 H) 7.79-7.86 (m, 1 H) 8.09 (s, 2 H) 8.19 (s, 1 H) 10.95 (br. s., 1 H) | 469.2 |
| 22 | 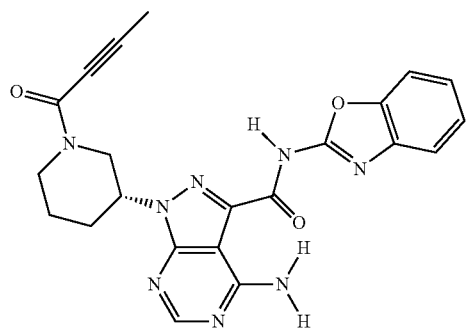 [SMILES: CC#CC(=O)N1CCC[C@@H](n2nc(C(=O)Nc3nc4ccccc4o3)c3c(N)ncnc32)C1] | 1H NMR (400 MHz, DMSO-d6) δ ppm 1.42-1.77 (m, 1 H) 1.95-2.02 (m, 1 H) 2.06 (s, 3 H) 2.10-2.22 (m, 1 H) 2.23-2.40 (m, 1 H) 2.95-3.10 (m, 0.5 H) 3.83-3.95 (m, 0.5 H) 4.09-4.19 (m, 0.5 H) 4.22-4.35 (m, 1 H) 4.37-4.56 (m, 1 H) 4.61-4.93 (m, 1 H) 7.26-7.44 (m, 2 H) 7.55-7.76 (m, 2 H) 7.95-8.49 (m, 3 H) | 445.9 |
| 23 | 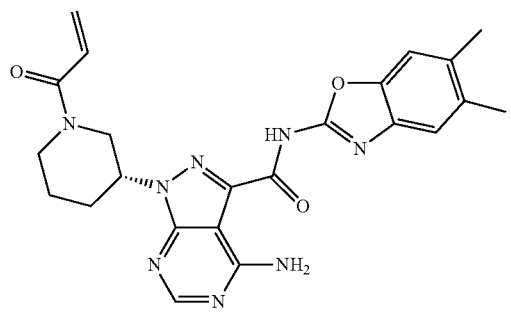 [SMILES: C=CC(=O)N1CCC[C@@H](n2nc(C(=O)Nc3nc4cc(C)c(C)cc4o3)c3c(N)ncnc32)C1] | ¹H NMR (400 MHz, DMSO-d₆) δ ppm 1.44-1.68 (m, 1 H) 1.87 (d, J = 12.30 Hz, 1 H) 2.06 (br. s., 1 H) 2.22 (d, J = 9.57 Hz, 8 H) 3.05-3.32 (m, 4 H) 4.03-4.25 (m, 3 H) 4.29-4.46 (m, 1 H) 4.60 (d, J = 18.45 Hz, 2 H) 5.51-5.75 (m, 1 H) 6.09 (br. s., 1 H) 6.61-6.95 (m, 1 H) 7.12 (s, 1 H) 7.24 (br. s., 1 H) 7.85 (br. s., 1 H) 8.10 (br. s., 1 H) 8.29 (s, 2 H) 11.07 (br. s., 1 H) | 461.2 |
| 24 | 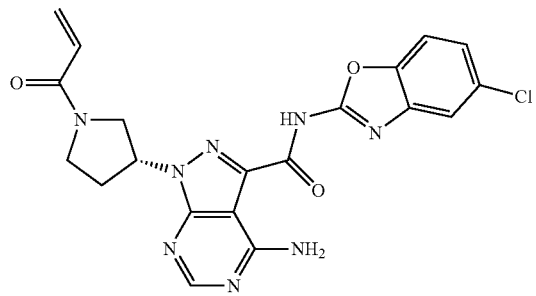 [SMILES: C=CC(=O)N1CC[C@@H](n2nc(C(=O)Nc3nc4cc(Cl)ccc4o3)c3c(N)ncnc32)C1] | ¹H NMR (400 MHz, DMSO-d₆) δ ppm 2.35-2.46 (m, 2 H) 3.60 (br. s., 1 H) 3.78 (br. s., 1 H) 3.84 (br. s., 1 H) 3.93 (br. s., 1 H) 4.02 (br. s., 1 H) 4.11 (d, J = 5.47 Hz, 1 H) 5.39-5.76 (m, 2 H) 6.00-6.29 (m, 1 H) 6.11 (s, 1 H) 6.15 (s, 1 H) 6.50-6.68 (m, 1 H) 7.35 (d, J = 8.88 Hz, 1 H) 7.69 (d, J = 8.88 Hz, 2 H) 8.11-8.38 (m, 2 H) 12.32 (br. s., 1 H) | 453.1 |

TABLE 6-continued
| 25 | 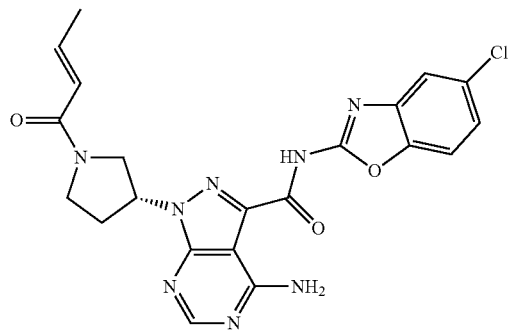 [SMILES: C/C=C/C(=O)N1CC[C@@H](n2nc(C(=O)Nc3nc4cc(Cl)ccc4o3)c3c(N)ncnc32)C1] | ¹H NMR (400 MHz, DMSO-d₆) δ ppm 1.80 (dd, J = 15.72, 6.15 Hz, 5 H) 1.92 (br. s., 1 H) 2.28-2.42 (m, 1 H) 2.50 (br. s., 1 H) 3.37-3.61 (m, 5 H) 3.65-3.78 (m, 2 H) 3.78-3.99 (m, 4 H) 4.01-4.15 (m, 1 H) 5.43 (t, J = 5.81 Hz, 1 H) 5.48-5.56 (m, 1 H) 6.21-6.34 (m, 1 H) 6.63-6.73 (m, 1 H) 7.24 (br. s., 1 H) 7.61 (br. s., 3 H) 8.02-8.15 (m, 2 H) 8.22 (s, 1 H) 12.38 (br. s., 1 H) | 469.2 |
TABLE 7
| 26 | 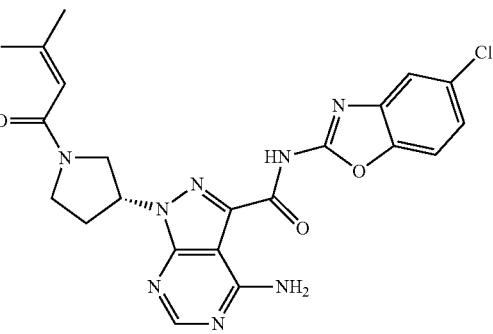 | ¹H NMR (400 MHz, DMSO-d₆) δ ppm 1.80 (d, J = 19.80 Hz, 3 H) 1.94-2.01 (m, 3 H) 3.45-3.57 (m, 1 H) 3.59-3.71 (m, 1 H) 3.76-3.94 (m, 3 H) 3.95-4.07 (m, 1 H) 5.32-5.64 (m, 1 H) 5.52-6.02 (m, 1 H) 7.19-7.44 (m, 1 H) 7.51-7.80 (m, 2 H) 8.08-8.16 (m, 1 H) 8.19-8.35 (m, 2 H) | 483.2 |
| 27 | 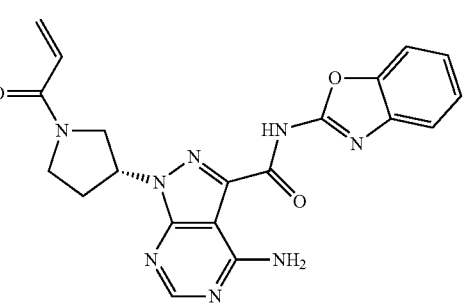 | ¹H NMR (400 MHz, DMSO-d₆) δ ppm 2.39-2.52 (m, 2 H) 3.51-3.67 (m, 1 H) 3.70-3.86 (m, 3 H) 3.88-3.98 (m, 3 H) 4.03-4.16 (m, 1 H) 5.41-5.55 (m, 1 H) 5.65 (ddd, J = 17.77, 10.25, 2.05 Hz, 1 H) 6.10-6.17 (m, 1 H) 6.51-6.67 (m, 1 H) 7.09-7.21 (m, 2 H) 7.40-7.51 (m, 1 H) 7.95 (br. s., 2 H) 8.11 (s, 1 H) 8.17 (s, 2 H) | 420.1 |
| 28 | 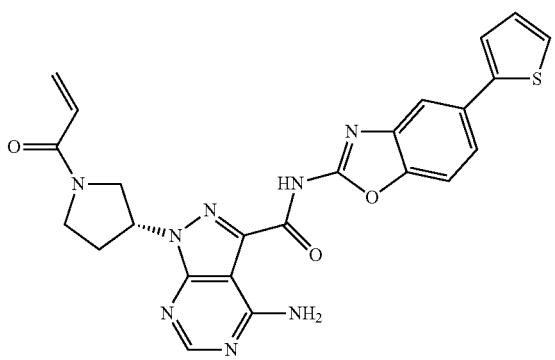 [SMILES: C=CC(=O)N1CC[C@@H](n2nc(C(=O)Nc3nc4cc(-c5cccs5)ccc4o3)c3c(N)ncnc32)C1] | ¹H NMR (400 MHz, DMSO-d₆) δ ppm 2.23-2.39 (m, 3 H) 3.57-3.94 (m, 4 H) 3.99-4.16 (m, 2 H) 5.39-5.46 (m, 1 H) 5.48-5.55 (m, 1 H) 5.61-5.70 (m, 2 H) 6.10-6.17 (m, 2 H) 6.51-6.67 (m, 2 H) 7.07-7.10 (m, 1 H) 7.32-7.41 (m, 1 H) 7.45 (d, J = 4.78 Hz, 1 H) 7.72 (s, 2 H) 7.88 (br. s., 2 H) 8.13 (s, 1 H) 10.57-10.99 (m, 1H) | 501.2 |

TABLE 7-continued

| # | Structure | 1H NMR | MS |
|---|---|---|---|
| 29 | (acryloyl-pyrrolidinyl-pyrazolopyrimidin-4-amine carboxamide with 5-methylbenzoxazol-2-yl) | 1H NMR (400 MHz, DMSO-d6) δ ppm 2.37 (s, 3 H) 3.47 (s, 4 H) 3.51-3.66 (m, 1 H) 3.73-4.01 (m, 3 H) 4.05-4.15 (m, 1 H) 5.42-5.57 (m, 1 H) 5.65 (ddd, J = 17.08, 10.25, 2.05 Hz, 1 H) 6.13 (dd, J = 19.13, 5.47 Hz, 1 H) 6.13 (dd, J = 14.69, 5.81 Hz, 1 H) 6.51-6.67 (m, 1 H) 7.03 (d, J = 7.52 Hz, 1 H) 7.34 (br. s., 1 H) 7.41 (d, J = 8.20 Hz, 1 H) 8.06 (s, 1 H) 8.10 (s, 1 H) 8.22 (s, 2 H) | 433.2 |
| 30 | (acryloyl-pyrrolidinyl-pyrazolopyrimidin-4-amine carboxamide with 6-fluorobenzoxazol-2-yl) | 1H NMR (400 MHz, DMSO-d6) δ ppm 2.36 (dd, J = 12.98, 6.15 Hz, 1 H) 2.54 (d, J = 5.47 Hz, 2 H) 3.51-3.68 (m, 0.5 H) 3.73-4.11 (m, 4 H) 5.45 (t, J = 6.15 Hz, 1 H) 5.54 (t, J = 6.15 Hz, 1 H) 5.65 (ddd, J = 17.08, 10.25, 2.05 Hz, 2 H) 6.09-6.17 (m, 1 H) 6.51-6.67 (m, 1 H) 7.02 (br. s., 2 H) 7.39 (br. s., 1 H) 7.54 (br. s., 1 H) 8.01-8.15 (m, 3 H) 8.21 (s, 1 H) | 437.1 |

TABLE 8

| # | Structure | 1H NMR | MS |
|---|---|---|---|
| 31 | (acryloyl-pyrrolidinyl-pyrazolopyrimidin-4-amine carboxamide with 5-(4-chlorophenyl)benzoxazol-2-yl) | 1H NMR (400 MHz, DMSO-d6) δ ppm 2.20-2.42 (m, 2 H) 3.59 (br. s., 3 H) 3.64-4.00 (m, 4 H) 4.09 (d, J = 7.52 Hz, 1 H) 5.38-5.56 (m, 1 H) 5.58-5.75 (m, 1 H) 6.05-6.22 (m, 1 H) 6.46-6.71 (m, 1 H) 7.47 (d, J = 8.88 Hz, 2 H) 7.62-7.72 (m, 3 H) 7.77-7.89 (m, 1 H) 8.08-8.13 (m, 1 H) 8.30 (br. s., 2 H) 11.05-11.16 (m, 1 H) | 529.1 |
| 32 | (dimethylamino-butenoyl-pyrrolidinyl-pyrazolopyrimidin-4-amine carboxamide with 5-chlorobenzoxazol-2-yl) | 1H NMR (400 MHz, DMSO-d6) δ ppm 2.14 (s, 3 H) 2.17 (s, 3 H) 2.34 (br. s., 2 H) 2.43 (br. s., 2 H) 3.03-3.14 (m, 2 H) 3.88 (br. s., 5 H) 4.07 (br. s., 5 H) 5.41 (br. s., 1 H) 5.48 (br. s., 1 H) 6.33-6.45 (m, 1 H) 6.61 (d, J = 6.83 Hz, 1 H) 7.02 (d, J = 8.20 Hz, 1 H) 7.33 (d, J = 8.20 Hz, 1 H) 7.45 (br. s., 1 H) 7.85 (br. s., 1 H) 8.10-8.15 (m, 2 H) 10.76 (br. s., 2 H) | 510.1 |

TABLE 8-continued

| | | | |
|---|---|---|---|
| 33 | 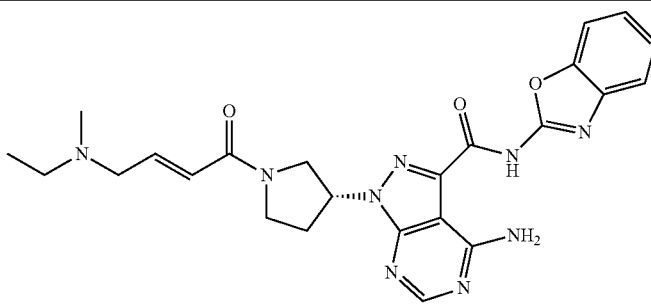 | ¹H NMR (400 MHz, DMSO-d₆) δ ppm 0.91-0.99 (m, 3 H) 2.06-2.14 (m, 3 H) 2.28-2.38 (m, 3 H) 2.41 (d, J = 6.83 Hz, 2 H) 3.04-3.13 (m, 2 H) 4.07 (br. s., 4 H) 5.41 (br. s., 1 H) 5.49 (br. s., 1 H) 6.31-6.44 (m, 1 H) 6.62 (d, J = 6.15 Hz, 1 H) 7.01 (d, J = 8.88 Hz, 1 H) 7.32 (d, J = 8.20 Hz, 1 H) 7.48 (br. s., 1 H) 7.84 (br. s., 2 H) 8.11 (s, 1 H) 8.22 (s, 2 H) 10.94 (br. s., 2 H) | 524.1 |
| 34 | 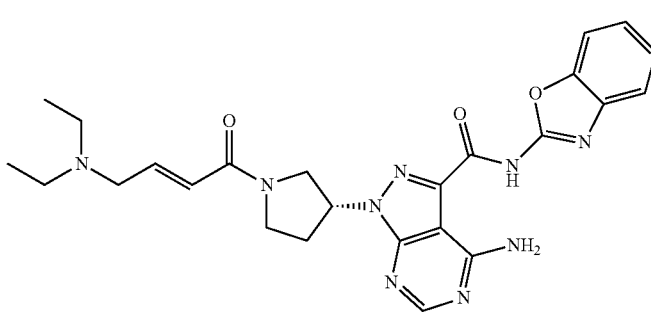 | ¹H NMR (400 MHz, DMSO-d₆) δ ppm 0.92 (dt, J = 14.35, 7.18 Hz, 6 H) 2.38-2.44 (m, 5 H) 3.09-3.23 (m, 3 H) 3.96-4.23 (m, 3 H) 5.26-5.58 (m, 1 H) 6.28-6.50 (m, 1 H) 6.56-6.72 (m, 1 H) 6.96-7.06 (m, 1 H) 7.27-7.36 (m, 1 H) 7.43-7.51 (m, 1 H) 7.79-7.88 (m, 1 H) 8.03 (s, 1 H) 8.22 (s, 2 H) 10.85-11.00 (m, 1 H) | 538.1 |
| 35 | 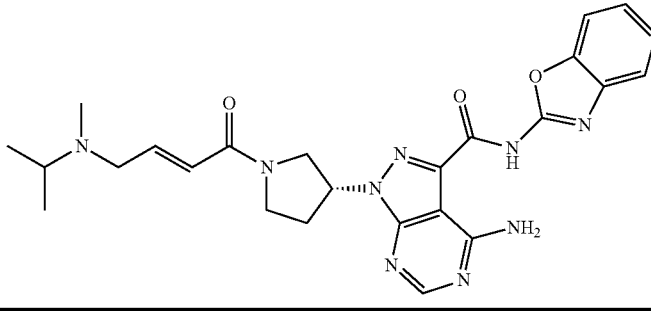 | ¹H NMR (400 MHz, DMSO-d₆) δ ppm 2.07 (d, J = 15.03 Hz, 6 H) 2.33 (d, J = 7.52 Hz, 2 H) 2.60-2.91 (m, 1 H) 3.03-3.20 (m, 2 H) 4.00-4.14 (m, 1 H) 5.31-5.58 (m, 2 H) 6.25-6.46 (m, 2 H) 6.52-6.68 (m, 2 H) 6.95-7.06 (m, 1 H) 7.27-7.36 (m, 1 H) 7.41-7.53 (m, 1 H) 7.80-7.91 (m, 2 H) 8.03 (s, 1 H) 8.22 (s, 2 H) | 538.1 |

TABLE 9

| | | |
|---|---|---|
| 36 | 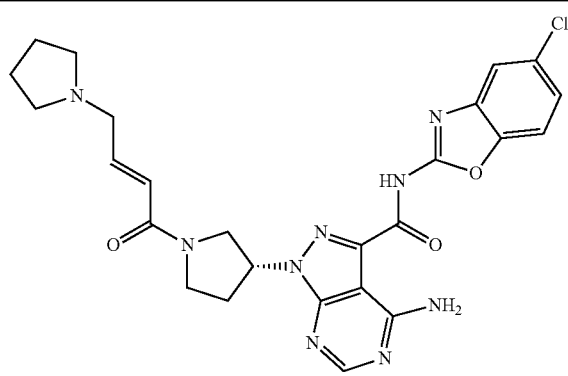 | ¹H NMR (400 MHz, DMSO-d₆) δ ppm 1.60-1.70 (m, 1 H) 1.65 (d, J = 12.30 Hz, 4H) 2.33 (d, J = 6.83 Hz, 2 H) 2.41 (br. s., 2 H) 3.12-3.25 (m, 2 H) 3.19 (d, J = 12.30 Hz, 2 H) 3.68-3.79 (m, 2 H) 3.79-3.96 (m, 2 H) 3.97-4.24 (m, 2 H) 4.02-4.15 (m, 1 H) 5.40 (br. s., 1 H) 5.49 (br. s., 1 H) 6.31-6.44 (m, 2 H) 6.62-6.68 (m, 2 H) 7.01 (d, J = 8.20 Hz, 2 H) 7.31 (d, J = 8.20 Hz, 2 H) 7.47 (s, 1 H) 7.79-7.90 (m, 1 H) 7.84 (br. s., 2 H) 8.07-8.13 (m, 1 H) 8.07-8.14 (m, 1 H) 8.03 (s, 1 H) 8.22 (s, 2 H) 10.93 (br. s., 1 H) | 536.1 |

TABLE 9-continued

| | | | |
|---|---|---|---|
| 37 | 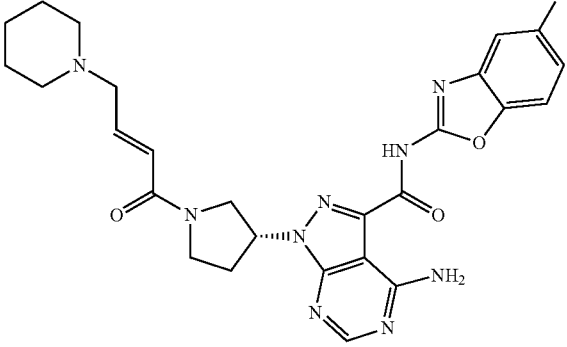 | ¹H NMR (400 MHz, DMSO-d₆) δ ppm 1.34 (br. s., 2 H) 1.40-1.52 (m, 4 H) 2.33 (br. s., 4 H) 2.39-2.44 (m, 1 H) 2.93-3.20 (m, 2 H) 3.80-3.97 (m, 2 H) 4.06 (d, J = 7.52 Hz, 2 H) 5.40 (br. s., 1 H) 5.49 (br. s., 1 H) 6.31-6.44 (m, 1 H) 6.57-6.66 (m, 1 H) 7.01 (d, J = 8.20 Hz, 1 H) 7.32 (d, J = 8.20 Hz, 1 H) 7.45 (s, 1 H) 7.84 (br. s., 1 H) 8.03 (s, 1 H) 8.22 (s, 2 H) 10.81 (br. s., 1 H) | 550.1 |
| 38 | 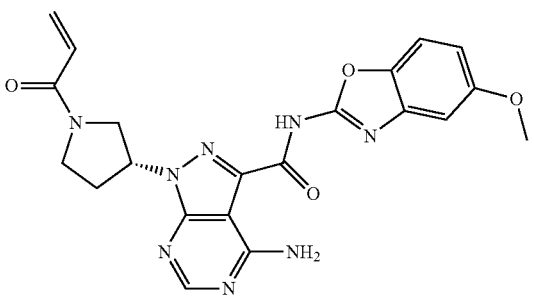 [SMILES: C=CC(=O)N1CC[C@@H](n2nc(C(=O)Nc3nc4cc(OC)ccc4o3)c3c(N)ncnc32)C1] | ¹H NMR (400 MHz, DMSO-d₆) δ ppm 2.43 (d, J = 5.61 Hz, 1 H) 3.50-3.70 (m, 2 H) 3.74-3.88 (m, 2 H) 3.81 (s, 3 H) 3.96 (d, J = 7.07 Hz, 1 H) 4.05 (br. s., 1 H) 4.15 (d, J = 7.32 Hz, 1 H) 5.51 (d, J = 6.10 Hz, 1 H) 5.60 (s, 1 H) 5.69 (ddd, J = 15.98, 10.37, 2.44 Hz, 1 H) 6.17 (ddd, J = 16.65, 4.94, 2.32 Hz, 1 H) 6.55-6.71 (m, 1 H) 6.92 (dd, J = 8.90, 2.56 Hz, 1 H) 7.20 (br. s., 1 H) 7.59 (d, J = 9.02 Hz, 1 H) 8.33 (s, 2 H) | 450.2 |
| 39 | 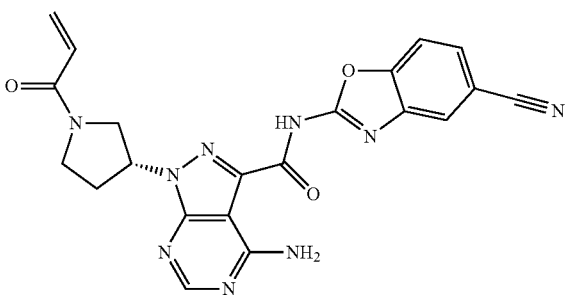 [SMILES: C=CC(=O)N1CC[C@@H](n2nc(C(=O)Nc3nc4cc(C#N)ccc4o3)c3c(N)ncnc32)C1] | ¹H NMR (400 MHz, DMSO-d₆) δ ppm 2.33 (br. s., 1 H) 2.66-2.70 (m, 1 H) 3.35 (br. s., 2 H) 3.74-3.90 (m, 3 H) 3.94 (d, J = 7.80 Hz, 1 H) 4.14 (s, 1 H) 5.48 (s, 1 H) 5.56 (s, 1 H) 5.63-5.74 (m, 1 H) 6.11-6.20 (m, 1 H) 6.54-6.68 (m, 1 H) 7.61 (br. s., 1 H) 7.67 (br. s., 1 H) 7.98 (br. s., 1 H) 8.09-8.25 (m, 2 H) | 444.2 |
| 40 | 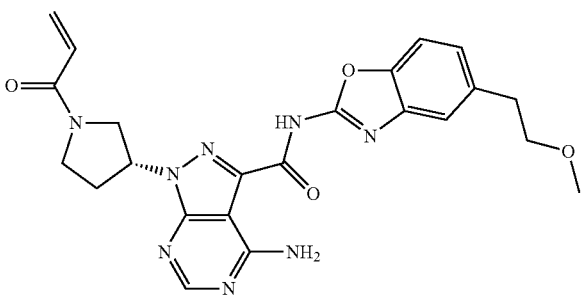 [SMILES: C=CC(=O)N1CC[C@@H](n2nc(C(=O)Nc3nc4cc(CCOC)ccc4o3)c3c(N)ncnc32)C1] | ¹H NMR (400 MHz, DMSO-d₆) δ ppm 2.39 (d, J = 6.83 Hz, 2 H) 2.89 (t, J = 6.49 Hz, 2 H) 3.22 (s, 3 H) 3.54 (t, J = 6.49 Hz, 2 H) 3.73-3.88 (m, 1 H) 3.93 (d, J = 6.15 Hz, 1 H) 4.01 (br. s., 1 H) 4.06-4.15 (m, 1 H) 5.45-5.70 (m, 2 H) 6.10-6.17 (m, 1 H) 6.51-6.67 (m, 1 H) 7.19 (m, J = 8.20 Hz, 1 H) 7.47 (br. s., 1 H) 7.54 (m, J = 8.20 Hz, 1 H) 8.20 (br. s., 2 H) 8.27 (br. s., 1 H) 12.13 (br. s., 1 H) | 477.2 |

TABLE 10

| | | | |
|---|---|---|---|
| 41 | 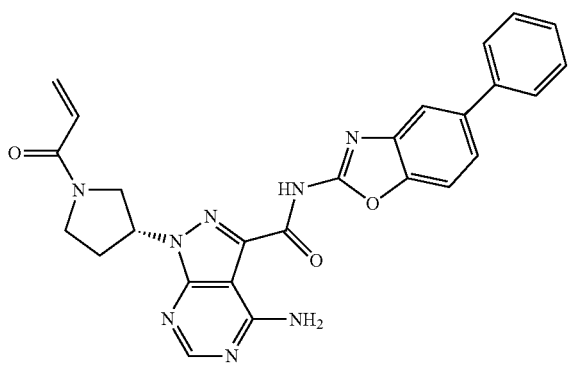 [SMILES: C=CC(=O)N1CC[C@@H](n2nc(C(=O)Nc3nc4cc(-c5ccccc5)ccc4o3)c3c(N)ncnc32)C1] | ¹H NMR (400 MHz, DMSO-d₆) δ ppm 2.32-2.43 (m, 1 H) 3.52-3.63 (m, 1 H) 3.74-4.02 (m, 2 H) 4.06-4.16 (m, 1 H) 5.43-5.58 (m, 1 H) 5.62-5.70 (m, 2 H) 6.10-6.17 (m, 2 H) 6.51-6.67 (m, 1 H) 7.31-7.37 (m, 1 H) 7.41-7.54 (m, 3 H) 7.66 (d, J = 7.52 Hz, 3 H) 7.79 (br. s., 1 H) 8.00-8.16 (m, 2 H) 8.03 (s, 1 H) 8.22 (s, 2 H) | 496.1 |
| 42 | 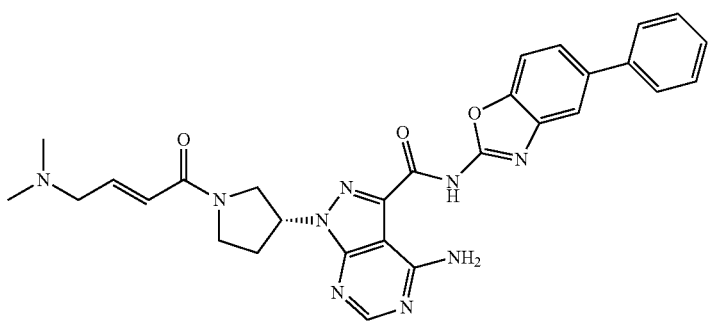 [SMILES: CN(C)C/C=C/C(=O)N1CC[C@@H](n2nc(C(=O)Nc3nc4cc(-c5ccccc5)ccc4o3)c3c(N)ncnc32)C1] | ¹H NMR (400 MHz, DMSO-d₆) δ ppm 2.11 (s, 3 H) 2.14 (s, 3 H) 2.34 (br. s., 3 H) 2.42 (d, J = 6.83 Hz, 1 H) 3.02 (dd, J = 16.40, 6.15 Hz, 3 H) 3.81-3.96 (m, 6 H) 3.97-4.23 (m, 4 H) 5.45 (dt, J = 33.50, 6.80 Hz, 1 H) 6.31-6.44 (m, 1 H) 6.57-6.64 (m, 1 H) 7.30 (d, J = 8.20 Hz, 3 H) 7.40 (d, J = 8.20 Hz, 3 H) 7.59 (br. s., 2 H) 7.72 (s, 1 H) 7.87 (br. s., 1 H) 8.03 (s, 1 H) 8.22 (s, 2 H) 10.86 (br. s., 1 H) | 552.1 |
| 43 | 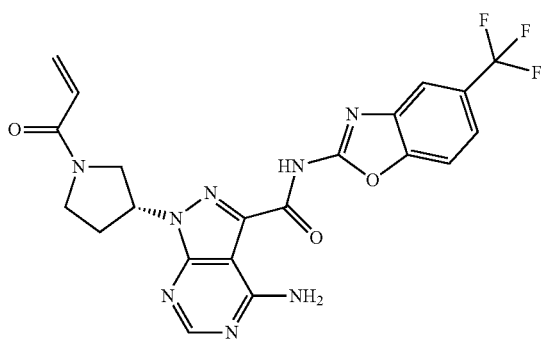 [SMILES: C=CC(=O)N1CC[C@@H](n2nc(C(=O)Nc3nc4cc(C(F)(F)F)ccc4o3)c3c(N)ncnc32)C1] | ¹H NMR (400 MHz, DMSO-d₆) δ ppm 2.41 (br. s., 1 H) 2.61 (br. s., 1 H) 3.62 (br. s., 2 H) 3.81 (br. s., 1 H) 3.87 (br. s., 1 H) 3.96 (br. s., 1 H) 4.06 (d, J = 10.25 Hz, 1 H) 4.16 (br. s., 1 H) 5.46-5.63 (m, 1 H) 5.63-5.74 (m, 1 H) 6.10-6.23 (m, 1 H) 6.55-6.70 (m, 1 H) 7.68 (d, J = 7.52 Hz, 1 H) 7.88 (d, J = 7.52 Hz, 1 H) 8.01 (br. s., 1 H) 8.20 (br. s., 1 H) 8.30 (br. s., 2 H) | 487.2 |
| 44 | 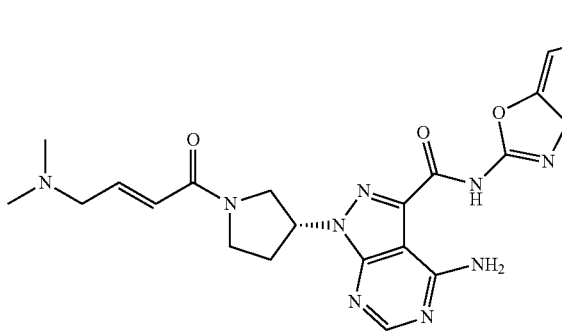 | ¹H NMR (400 MHz, DMSO-d₆) δ ppm 2.19 (s, 3 H) 2.22 (s, 3 H) 2.28-2.39 (m, 1 H) 2.85 (br. s., 1 H) 2.98-3.00 (m, 1 H) 3.55 (d, J = 11.62 Hz, 1 H) 3.63-3.82 (m, 5 H) 3.89 (dd, J = 12.30, 6.83 Hz, 3 H) 3.99-4.18 (m, 2 H) 5.39-5.52 (m, 1 H) 6.36-6.48 (m, 1 H) 6.57-6.66 (m, 1 H) 7.36 (d, J = 8.20 Hz, 1 H) 7.52 (d, J = 8.20 Hz, 1 H) 7.74 (s, 1 H) 7.87 (br. s., 1 H) 8.12 (d, J = 5.47 Hz, 1 H) 10.68 (br. s., 1 H) | 544.3 |

TABLE 10-continued

| 45 | 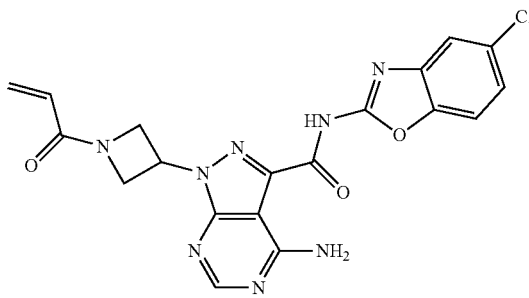 | $^1$H NMR (400 MHz, DMSO-d$_6$) δ ppm 4.33 (d, J = 4.78 Hz, 1 H) 4.41 (d, J = 9.57 Hz, 1 H) 4.58 (br. s., 1 H) 4.72 (t, J = 8.54 Hz, 1 H) 5.70 (d, J = 10.25 Hz, 2 H) 6.14 (d, J = 17.08 Hz, 1 H) 6.37 (dd, J = 17.08, 10.25 Hz, 1 H) 6.96-7.02 (m, 1 H) 6.99 (d, J = 6.15 Hz, 1 H) 7.31 (d, J = 8.88 Hz, 1 H) 7.38 (s, 1 H) 7.85 (br. s., 1 H) 8.03 (s, 1 H) 8.22 (s, 2 H) 10.97 (br. s., 1 H) | 466.2 |

TABLE 11

| 46 | 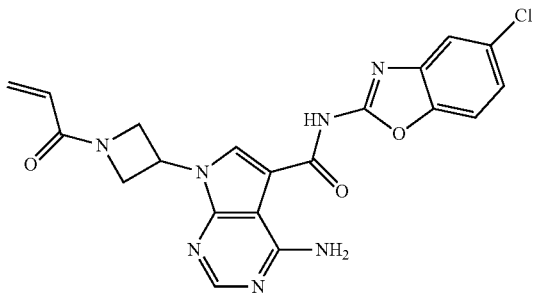 [SMILES: C=CC(=O)N1CC(n2cc(C(=O)Nc3nc4cc(Cl)ccc4o3)c3c(N)ncnc32)C1] | $^1$H NMR (400 MHz, DMSO-d6) δ ppm 4.21-4.34 (m, 1 H) 4.42 (t, J = 9.23 Hz, 1 H) 4.61 (d, J = 5.47 Hz, 1 H) 4.65-4.74 (m, 1 H) 5.52 (d, J = 5.47 Hz, 1 H) 5.69 (dd, J = 10.25, 2.05 Hz, 1 H) 6.13 (dd, J = 17.08, 2.05 Hz, 1 H) 6.36 (dd, J = 17.08, 10.25 Hz, 1 H) 6.99 (d, J = 8.20 Hz, 1 H) 7.31 (d, J = 8.20 Hz, 1 H) 7.39 (s, 1 H) 7.98-8.05 (m, 1 H) 8.18 (br. s., 1 H) 8.22 (s, 2 H) | 438.2 |
| 47 | 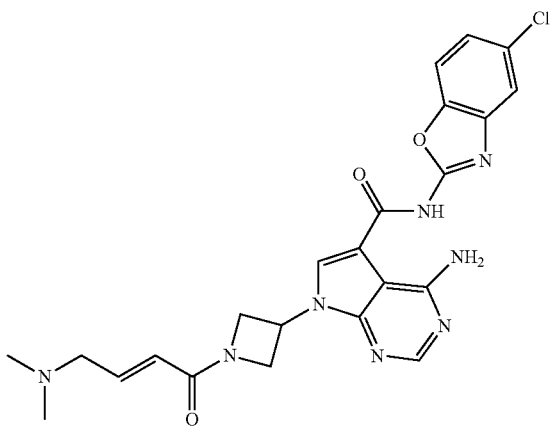 [SMILES: CN(C)C/C=C/C(=O)N1CC(n2cc(C(=O)Nc3nc4cc(Cl)ccc4o3)c3c(N)ncnc32)C1] | $^1$H NMR (400 MHz, DMSO-d$_6$) δ ppm 2.10-2.17 (m, 6 H) 3.02 (d, J = 5.47 Hz, 2 H) 4.20-4.27 (m, 2 H) 4.40 (t, J = 9.23 Hz, 2 H) 4.57 (d, J = 5.47 Hz, 2 H) 4.69 (t, J = 8.54 Hz, 2 H) 5.52 (br. s., 1 H) 6.15 (d, J = 15.72 Hz, 1 H) 6.58-6.66 (m, 1 H) 7.04 (d, J = 8.20 Hz, 1 H) 7.35 (d, J = 8.20 Hz, 1 H) 7.43 (s, 1 H) 8.11 (br. s., 1 H) 8.18 (s, 2 H) | 495.2 |
| 48 | 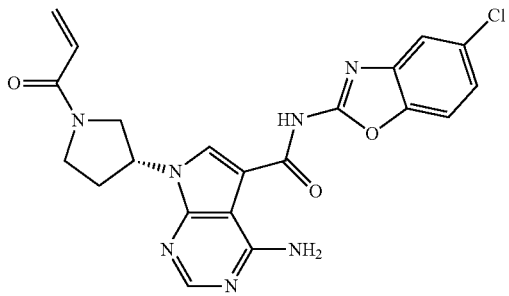 [SMILES: C=CC(=O)N1CC[C@@H](n2cc(C(=O)Nc3nc4cc(Cl)ccc4o3)c3c(N)ncnc32)C1] | $^1$H NMR (400 MHz, DMSO-d$_6$) δ ppm 2.25-2.43 (m, 2 H) 3.73-3.81 (m, 2 H) 3.86-3.97 (m, 2 H) 4.06-4.15 (m, 1 H) 5.23 (br. s., 1 H) 5.34 (d, J = 6.15 Hz, 2 H) 5.63-5.73 (m, 3 H) 6.12-6.21 (m, 2 H) 6.55-6.67 (m, 2 H) 6.95 (d, J = 8.20 Hz, 2 H) 7.10 (br. s., 1 H) 7.25 (d, J = 8.20 Hz, 1 H) 7.39 (br. s., 2 H) 7.63 (s, 1 H) 7.67 (s, 2 H) 8.02 (s, 1 H) 8.27 (br. s., 4 H) 10.29 (br. s., 1 H) | 452.1 |

TABLE 11-continued
| 49 | 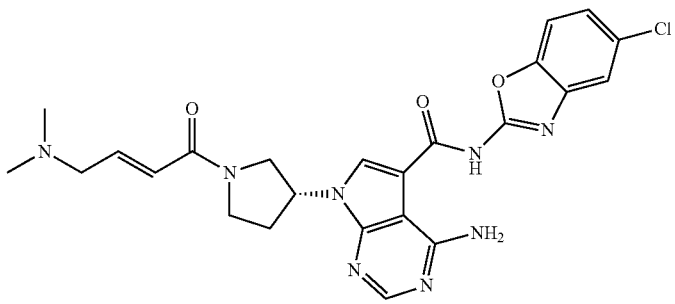 [SMILES: CN(C)C/C=C/C(=O)N1CC[C@@H](n2cc(C(=O)Nc3nc4cc(Cl)ccc4o3)c3c(N)ncnc32)C1] | ¹H NMR (400 MHz, DMSO-d₆) δ ppm 2.10 (s, 3 H) 2.15 (s, 3 H) 2.95-3.09 (m, 4 H) 3.02 (d, J = 17.77 Hz, 4 H) 3.13 (s, 17 H) 5.16-5.40 (m, 3 H) 6.26-6.51 (m, 1 H) 6.56-6.74 (m, 1 H) 6.90-7.06 (m, 1 H) 7.22-7.32 (m, 1 H) 7.36-7.48 (m, 1 H) 7.59-7.76 (m, 1 H) 7.96-8.09 (m, 1 H) 8.25 (s, 2 H) | 509.1 |
| 50 | 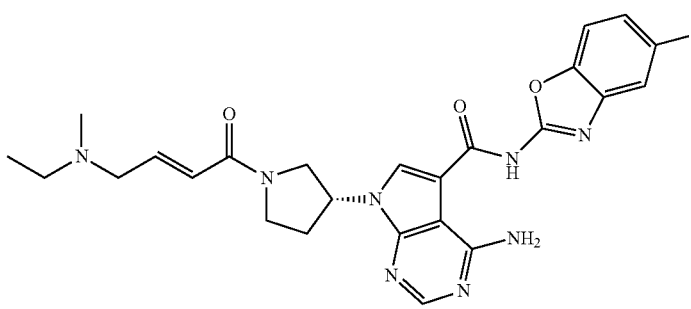 | ¹H NMR (400 MHz, DMSO-d₆) δ ppm 0.95 (dt, J = 11.28, 7.00 Hz, 3 H) 2.11 (d, J = 12.98 Hz, 2 H) 2.27-2.45 (m, 2 H) 3.13 (m, 2 H) 3.87-3.97 (m, 1 H) 3.98-4.24 (m, 1 H) 5.12-5.42 (m, 1 H) 6.30-6.50 (m, 1 H) 6.58-6.73 (m, 1 H) 6.99-7.07 (m, 1 H) 7.31-7.38 (m, 1 H) 7.40-7.46 (m, 1 H) 7.77-7.85 (m, 1 H) 8.02-8.08 (m, 1 H) 8.19 (s, 2 H) | 523.2 |
TABLE 12
| 51 | 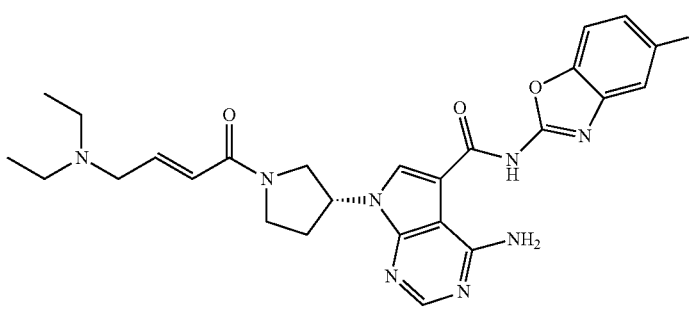 | ¹H NMR (400 MHz, DMSO-d₆) δ ppm 0.88-0.97 (m, 6 H) 2.38-2.52 (m, 4 H) 3.13-3.34 (m, 2 H) 3.70 (d, J = 6.83 Hz, 1 H) 3.78-3.96 (m, 1 H) 3.97-4.23 (m, 1 H) 5.14-5.41 (m, 1 H) 6.32-6.49 (m, 1 H) 6.67 (tt, J = 13.84, 7.00 Hz, 1 H) 6.99 (d, J = 8.20 Hz, 1 H) 1.30 (dd, J = 8.54, 2.39 Hz, 1 H) 7.41 (br. s., 1 H) 7.74 (d, J = 13.67 Hz, 1 H) 8.03 (s, 1 H) 8.21 (s, 2 H) | 537.2 |
| 52 | 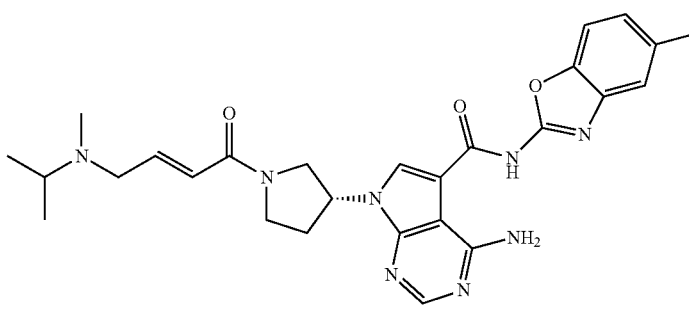 | ¹H NMR (400 MHz, DMSO-d₆) δ ppm 0.92 (dd, J = 11.28, 6.49 Hz, 6 H) 2.02-2.14 (m, 1 H) 2.08 (d, J = 13.67 Hz, 3 H) 2.76 (dt, J = 12.98, 6.49 Hz, 1 H) 3.14 (dd, J = 17.08, 6.15 Hz, 1 H) 3.71 (br. s., 1 H) 3.79-3.96 (m, 1 H) 3.97-4.26 (m, 1 H) 5.13-5.37 (m, 1 H) 6.30-6.47 (m, 1 H) 6.54-6.70 (m, 1 H) 6.94-7.06 (m, 1 H) 7.27-7.36 (m, 1 H) 7.39-7.45 (m, 1 H) 7.71-7.80 (m, 1 H) 8.04 (s, 1 H) 8.20 (s, 2 H) | 537.2 |

/ TABLE 12-continued
| | | | |
|---|---|---|---|
| 53 | 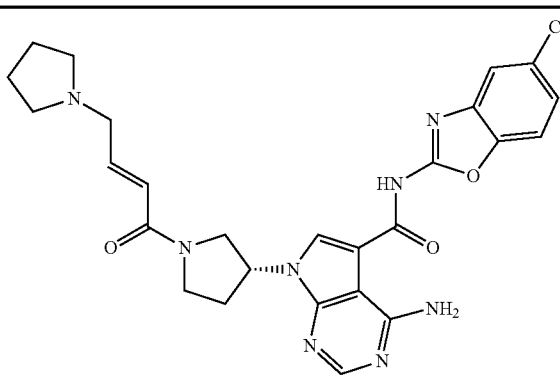 | ¹H NMR (400 MHz, DMSO-d₆) δ ppm 1.61-1.72 (m, 4 H) 3.09-3.34 (m, 2 H) 3.86 (d, J = 6.83 Hz, 1 H) 3.95-4.22 (m, 1 H) 5.09-5.37 (m, 1 H) 6.30-6.48 (m, 1 H) 6.58-6.76 (m, 1 H) 6.89-7.01 (m, 1 H) 7.20-7.29 (m, 1 H) 7.38-7.44 (m, 1 H) 7.59-7.69 (m, 1 H) 7.98-8.06 (m, 1 H) 8.03 (s, 1 H) 8.22 (s, 2 H) | 535.2 |
| 54 | 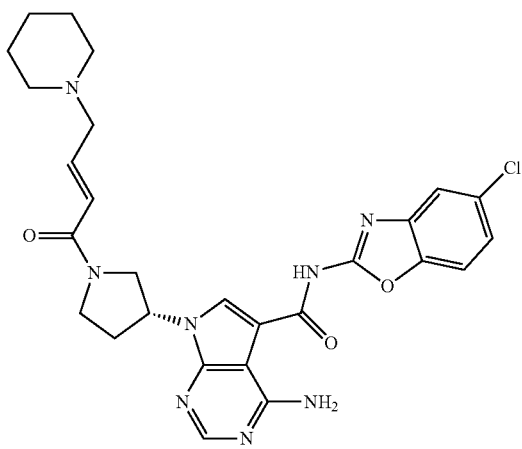 [SMILES: Nc1ncnc2c1c(C(=O)Nc1nc3cc(Cl)ccc3o1)cn2[C@@H]1CCN(C(=O)/C=C/CN2CCCCC2)C1] | ¹H NMR (400 MHz, DMSO-d₆) δ ppm 1.19-1.30 (m, 1 H) 1.33 (br. s., 3 H) 1.40-1.51 (m, 6 H) 2.24-2.36 (m, 7 H) 2.41-2.51 (m, 12 H) 3.04 (dd, J = 17.77, 6.15 Hz, 3 H) 3.13 (br. s., 2 H) 3.47 (br. s., 16 H) 3.71 (br. s., 11 H) 3.88 (dd J = 12.64, 6.49 Hz, 10 H) 3.96-4.22 (m, 6 H) 5.09-5.46 (m, 1 H) 6.33-6.44 (m, 1 H) 6.52-6.78 (m, 1 H) 6.93-7.03 (m, 1 H) 7.22-7.34 (m, 1 H) 7.36-7.48 (m, 1 H) 7.72 (d, J = 15.03 Hz, 1 H) 8.03 (s, 1 H) 8.22 (s, 2 H) | 549.3 |
| 55 | 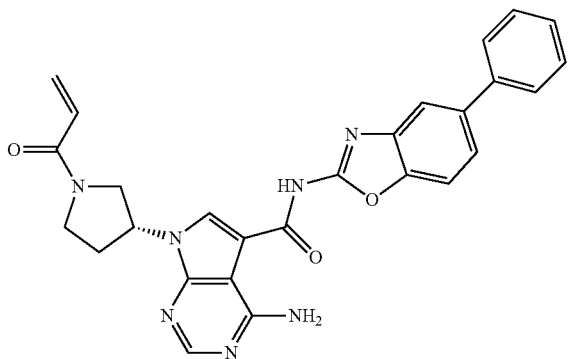 [SMILES: C=CC(=O)N1CC[C@@H](n2cc(C(=O)Nc3nc4cc(-c5ccccc5)ccc4o3)c3c(N)ncnc32)C1] | ¹H NMR (400 MHz, DMSO-d₆) δ ppm 2.36 (br. s., 1 H) 3.76 (br. s., 2 H) 3.91-4.09 (m 4 H) 5.26 (br. s., 1 H) 5.36 (br. s., 1 H) 5.64-5.73 (m, 2 H) 6.12-6.21 (m, 2 H) 6.62 (d, J = 9.57 Hz, 1 H) 7.29-7.38 (m, 3 H) 7.43 (d, J = 7.52 Hz, 6 H) 7.62 (d, J = 6.83 Hz, 4 H) 7.68 (br. s., 3 H) 7.90 (br. s., 2 H) 8.07 (s, 1 H) 8.21 (s, 2 H) | 494.3 |
TABLE 13
| | | | |
|---|---|---|---|
| 56 | 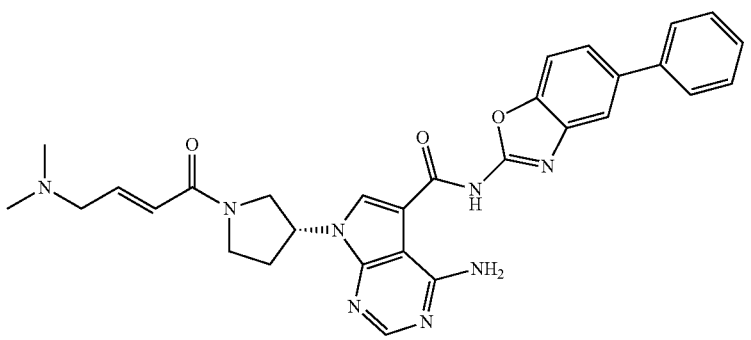 [SMILES: CN(C)C/C=C/C(=O)N1CC[C@@H](n2cc(C(=O)Nc3nc4cc(-c5ccccc5)ccc4o3)c3c(N)ncnc32)C1] | ¹H NMR (400 MHz, DMSO-d₆) δ ppm 2.11 (s, 3 H) 2.14 (s, 3 H) 2.35 (br. s., 1 H) 3.02 (dd, J = 17.08, 5.47 Hz, 2 H) 4.07 (br. s., 5 H) 5.14-5.41 (m, 1 H) 6.34-6.45 (m, 1 H) 6.56-6.72 (m, 1 H) 7.31 (br. s., 1 H) 7.43 (br. s., 2 H) 7.48 (br. s., 1 H) 7.63 (d, J = 5.47 Hz, 2 H) 7.71 (br. s., 1 H) 7.97 (br. s., 1 H) 8.06-8.11 (m, 1 H) 8.21 (s, 2 H) | 551.3 |

TABLE 13-continued

| 57 | 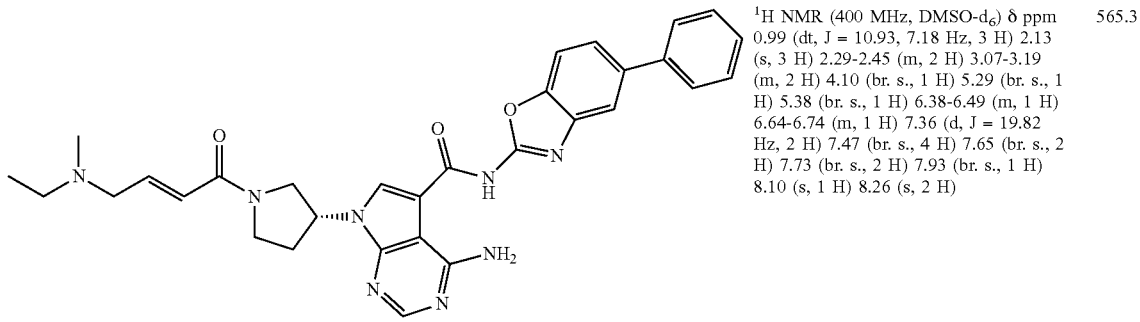 | ¹H NMR (400 MHz, DMSO-d₆) δ ppm 0.99 (dt, J = 10.93, 7.18 Hz, 3 H) 2.13 (s, 3 H) 2.29-2.45 (m, 2 H) 3.07-3.19 (m, 2 H) 4.10 (br. s., 1 H) 5.29 (br. s., 1 H) 5.38 (br. s., 1 H) 6.38-6.49 (m, 1 H) 6.64-6.74 (m, 1 H) 7.36 (d, J = 19.82 Hz, 2 H) 7.47 (br. s., 4 H) 7.65 (br. s., 2 H) 7.73 (br. s., 2 H) 7.93 (br. s., 1 H) 8.10 (s, 1 H) 8.26 (s, 2 H) | 565.3 |
| --- | --- | --- | --- |
| 58 | 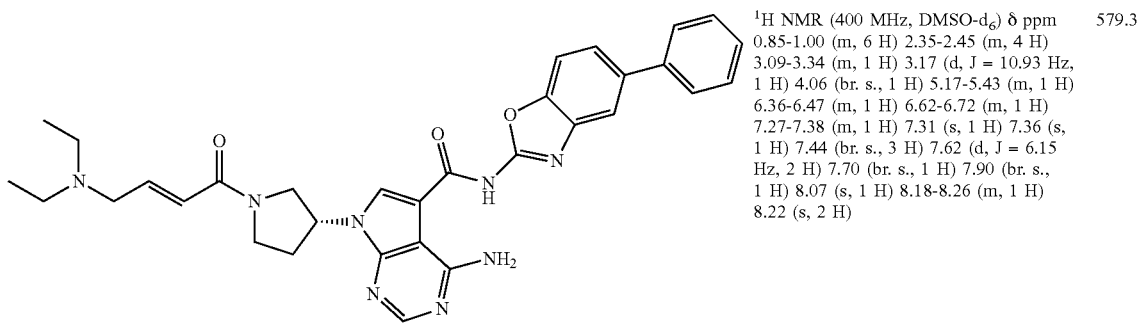 | ¹H NMR (400 MHz, DMSO-d₆) δ ppm 0.85-1.00 (m, 6 H) 2.35-2.45 (m, 4 H) 3.09-3.34 (m, 1 H) 3.17 (d, J = 10.93 Hz, 1 H) 4.06 (br. s., 1 H) 5.17-5.43 (m, 1 H) 6.36-6.47 (m, 1 H) 6.62-6.72 (m, 1 H) 7.27-7.38 (m, 1 H) 7.31 (s, 1 H) 7.36 (s, 1 H) 7.44 (br. s., 3 H) 7.62 (d, J = 6.15 Hz, 2 H) 7.70 (br. s., 1 H) 7.90 (br. s., 1 H) 8.07 (s, 1 H) 8.18-8.26 (m, 1 H) 8.22 (s, 2 H) | 579.3 |
| 59 | 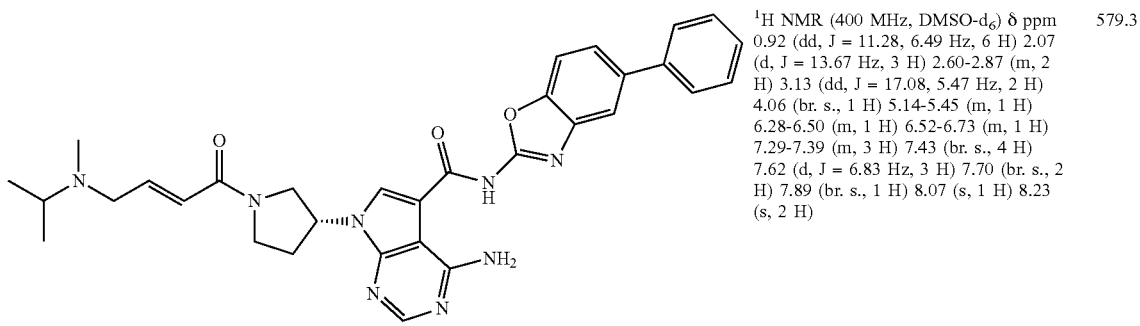 | ¹H NMR (400 MHz, DMSO-d₆) δ ppm 0.92 (dd, J = 11.28, 6.49 Hz, 6 H) 2.07 (d, J = 13.67 Hz, 3 H) 2.60-2.87 (m, 2 H) 3.13 (dd, J = 17.08, 5.47 Hz, 2 H) 4.06 (br. s., 1 H) 5.14-5.45 (m, 1 H) 6.28-6.50 (m, 1 H) 6.52-6.73 (m, 1 H) 7.29-7.39 (m, 3 H) 7.43 (br. s., 4 H) 7.62 (d, J = 6.83 Hz, 3 H) 7.70 (br. s., 2 H) 7.89 (br. s., 1 H) 8.07 (s, 1 H) 8.23 (s, 2 H) | 579.3 |
| 60 | 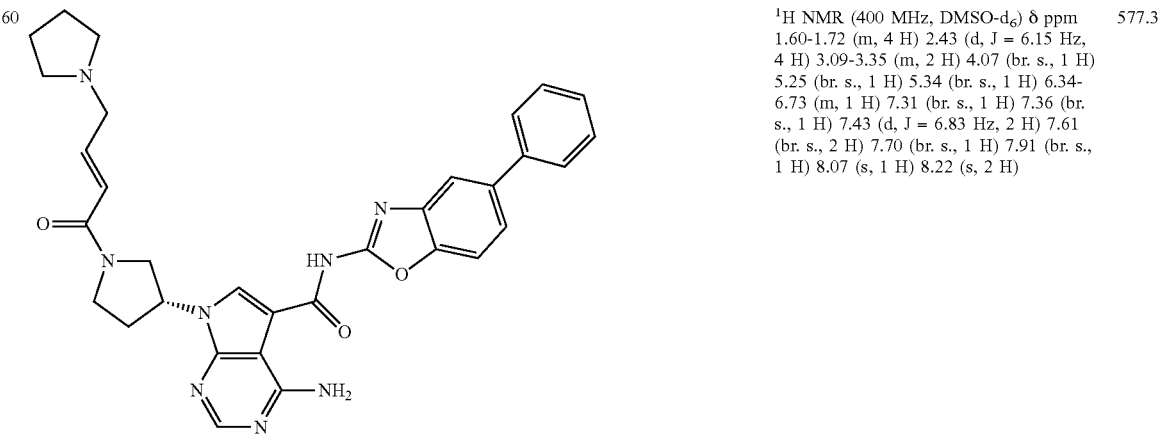 | ¹H NMR (400 MHz, DMSO-d₆) δ ppm 1.60-1.72 (m, 4 H) 2.43 (d, J = 6.15 Hz, 4 H) 3.09-3.35 (m, 2 H) 4.07 (br. s., 1 H) 5.25 (br. s., 1 H) 5.34 (br. s., 1 H) 6.34-6.73 (m, 1 H) 7.31 (br. s., 1 H) 7.36 (br. s., 1 H) 7.43 (d, J = 6.83 Hz, 2 H) 7.61 (br. s., 2 H) 7.70 (br. s., 1 H) 7.91 (br. s., 1 H) 8.07 (s, 1 H) 8.22 (s, 2 H) | 577.3 |

TABLE 14

| | | | |
|---|---|---|---|
| 61 | 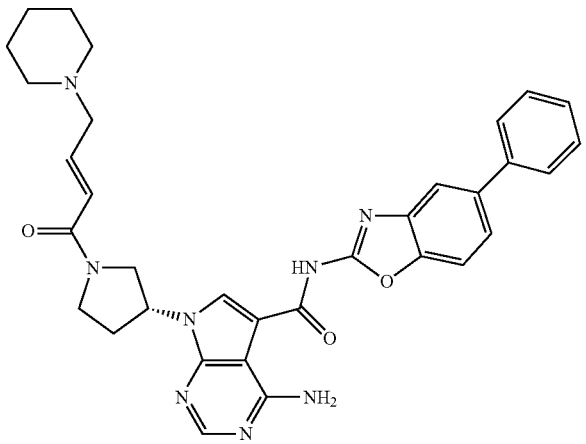 [SMILES: Nc1ncnc2c1c(C(=O)Nc1nc3cc(-c4ccccc4)ccc3o1)cn2[C@@H]1CCN(C(=O)/C=C/CN2CCCCC2)C1] | ¹H NMR (400 MHz, DMSO-d₆) δ ppm 1.34 (br. s., 2 H) 1.46 (br. s., 4 H) 2.29 (br. s., 4 H) 3.04 (dd, J = 17.43, 5.81 Hz, 2 H) 4.06 (br. s., 1 H) 5.20-5.40 (m, 1 H) 6.32-6.44 (m, 1 H) 6.59-6.68 (m, 1 H) 7.31 (br. s., 1 H) 7.37 (br. s., 1 H) 7.43 (d, J = 8.20 Hz, 2 H) 7.62 (d, J = 6.15 Hz, 2 H) 7.70 (br. s., 1 H) 7.92 (br. s., 1 H) 8.07 (s, 1 H) 8.22 (s, 2 H) | 591.4 |
| 比較例 化合物1 | 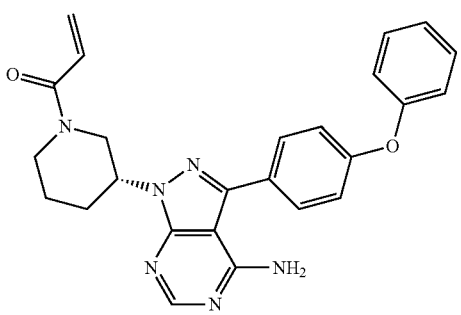 [SMILES: C=CC(=O)N1CCC[C@@H](n2nc(-c3ccc(Oc4ccccc4)cc3)c3c(N)ncnc32)C1] | ¹H NMR (400 MHz, DMSO-d₆) δ ppm 1.47-1.69 (m, 1 H) 1.86-1.97 (m, 1 H) 2.05-2.17 (m, 1 H) 2.17-2.32 (m, 1 H) 2.93-3.06 (m, 0.5 H) 3.12-3.26 (m, 1 H) 3.27-3.36 (m, 0.5 H) 3.64-3.75 (m, 0.5 H) 4.03-4.13 (m, 0.5 H) 4.15-4.27 (m, 1 H) 4.49-4.60 (m, 0.5 H) 4.62-4.79 (m, 1 H) 5.53-5.75 (m, 1 H) 6.02-6.17 (m, 1 H) 6.65-6.93 (m, 1.5 H) 7.08-7.23 (m, 5.5 H) 7.38-7.49 (m, 2 H) 7.61-7.71 (m, 2 H) 8.23-8.34 (m, 1 H) | 441.5 |

Test Example 1 Measurement of BTK Inhibitory Activity (In Vitro)

Regarding the setting of the conditions for a method for measuring the inhibitory activity of a compound against BTK kinase activity in vitro, it is described in the consumable reagent supplies price list for LabChip (registered trademark) series of PerkinElmer, Inc. that FL-PEPTIDE 2 corresponds to a substrate peptide for the measurement of BTK kinase activity. Therefore, FL-PEPTIDE 2 was used as a substrate. The purified recombinant human BTK protein used in the test was purchased from Carna Biosciences, Inc.

Regarding the measurement of the inhibitory activity of the compounds, firstly, the compounds of the present invention were diluted stepwise with DMSO. Subsequently, BTK protein, a substrate peptide (final concentration was 1 μM), magnesium chloride (final concentration was 10 mM), ATP (final concentration was 45 μM), and a DMSO solution of the compounds of the present invention (final concentration of DMSO was 5%) were added to a buffer solution for kinase reaction (20 mM HEPES (pH 7.5), 2 mM dithiotheitol, 0.01% Triton X-100), and after the solution was incubated for 40 minutes at 25° C., a kinase reaction was carried out. The reaction was terminated by adding EDTA thereto so as to obtain a final concentration of 30 mM. Finally, a substrate peptide that was not phosphorylated (S) and a phosphorylated peptide (P) were separated and detected by microchannel capillary electrophoresis with a LabChip EZ Reader II (PerkinElmer, Inc.). The amounts of phosphorylation reaction were determined from the respective peak heights of S and P, and the compound concentration at which the phosphorylation reaction could be suppressed by 50% was defined as the IC50 value (nM). The results are shown in Table 15 to Table 17 below.

TABLE 15

| Example No. | BTK inhibitory activity IC50 value (nM) |
|---|---|
| 1 | 0.415 |
| 2 | 0.464 |
| 3 | 0.443 |
| 4 | 0.888 |
| 5 | 1.253 |
| 6 | 0.738 |
| 7 | 0.457 |
| 8 | 1.266 |
| 9 | 1.37 |
| 10 | 2.384 |
| 11 | 2.143 |
| 12 | 0.433 |
| 13 | 0.813 |
| 14 | 14.141 |
| 15 | 0.786 |
| 16 | 0.733 |
| 17 | 0.811 |
| 18 | 0.788 |
| 19 | 0.69 |
| 20 | 0.801 |
| 21 | 0.777 |
| 22 | 14.209 |
| 23 | 1.583 |
| 24 | 0.591 |
| 25 | 1.166 |
| 26 | 2.788 |

TABLE 16

| Example No. | BTK inhibitory activity IC50 value (nM) |
| --- | --- |
| 27 | 1.433 |
| 28 | 0.559 |
| 29 | 0.485 |
| 30 | 0.566 |
| 31 | 1.671 |
| 32 | 0.634 |
| 33 | 0.887 |
| 34 | 0.79 |
| 35 | 0.792 |
| 36 | 0.867 |
| 37 | 0.786 |
| 38 | 0.888 |
| 39 | 1.12 |
| 40 | 2.087 |
| 41 | 0.442 |
| 42 | 0.771 |
| 43 | 0.546 |
| 44 | 0.877 |
| 45 | 1.249 |
| 46 | 3.272 |
| 47 | 7.345 |
| 48 | 0.836 |
| 49 | 1.529 |
| 50 | 1.407 |
| 51 | 1.48 |
| 52 | 1.195 |

TABLE 17

| Example No. | BTK inhibitory activity IC50 value (nM) |
| --- | --- |
| 53 | 1.675 |
| 54 | 1.436 |
| 55 | 0.799 |
| 56 | 1.337 |
| 57 | 1.507 |
| 58 | 1.844 |
| 59 | 1.507 |
| 60 | 1.88 |
| 61 | 2.341 |

From these test results, it was found that the compounds of the present invention have an inhibitory activity against BTK in vitro.

Test Example 2 BTK Inhibition Selectivity
Compared with EGFR Kinase Inhibitory Activity
(In Vitro)

1) Measurement of BTK Inhibitory Activity

The BTK inhibitory activity was measured in the same manner as in Test Example 1.

2) Measurement of EGFR Inhibitory Activity

Regarding the setting of the conditions for a method for measuring the inhibitory activity of a compound against EGFR kinase activity in vitro, it is described in the consumable reagent supplies price list for LabChip (registered trademark) series of PerkinElmer, Inc. that FL-PEPTIDE 22 corresponds to a substrate peptide for the measurement of EGFR kinase activity. Therefore, a biotinated peptide (biotin-EEPLYWSFPAKKK) was produced by referring to the amino acid sequence of the peptide. The purified recombinant human EGFR protein used in the test was purchased from Carna Biosciences, Inc.

Regarding the measurement of the inhibitory activity of the compounds, firstly, the compounds of the present invention were diluted stepwise with DMSO. Subsequently, EGFR protein, a substrate peptide (final concentration was 250 nM), magnesium chloride (final concentration was 10 mM), manganese chloride (final concentration was 10 mM), ATP (final concentration was 1.5 μM), and a DMSO solution of the compound of the present invention (final concentration of DMSO was 2.5%) were added to a buffer solution for kinase reaction (20 mM HEPES (pH 7.5), 2 mM dithiotheitol, 0.01% Triton X-100), and after the solution was incubated for 120 minutes at 25° C., a kinase reaction was carried out. The reaction was terminated by adding EDTA thereto so as to obtain a final concentration of 24 mM. Subsequently, a detection liquid containing Eu-labeled anti-phosphorylated tyrosine antibody PT66 (PerkinElmer, Inc.) and SureLight APC-SA (PerkinElmer, Inc.) was added thereto, and the system was left to stand for 2 hours or longer at room temperature. Finally, the amount of fluorescence upon irradiation with excitation light having a wavelength of 337 nm was measured at two wavelengths of 620 nm and 665 nm, with a PHERAstar FS (BMG Labtech GmbH). The amount of phosphorylation reaction was determined from the ratio of the amounts of fluorescence at the two wavelengths, and the compound concentration at which the phosphorylation reaction could be suppressed in 50% was defined as the IC50 value (nM).

3) BTK Inhibition Selectivity

The "EGFR inhibitory activity IC50 value (nM)/BTK inhibitory activity IC50 value (nM)" was calculated on the basis of the results obtained in the above sections 1) and 2), and thereby the BTK inhibition selectivity of the test compound was identified.

TABLE 18

| Example No. | EGFR inhibitory activity IC50 value (nM)/BTK inhibitory activity IC50 value (nM) |
| --- | --- |
| 4 | 929.2 |
| 5 | 241.0 |
| 6 | 33.3 |
| 8 | 22.9 |
| 9 | 28.4 |
| 11 | 1294.6 |
| 12 | 84.2 |
| 13 | 28.8 |
| 14 | 128.1 |
| 15 | 145.0 |
| 16 | 158.1 |
| 17 | 157.2 |
| 18 | 121.3 |
| 19 | 144.8 |
| 20 | 138.2 |
| 21 | 147.4 |
| 22 | 260.1 |
| 25 | 173.7 |
| 26 | 642.8 |
| 30 | 21.3 |
| 32 | 43.1 |
| 33 | 43.4 |
| 34 | 79.3 |
| 35 | 35.1 |
| 36 | 59.8 |

TABLE 19

| Example No. | EGFR inhibitory activity IC50 value (nM)/BTK inhibitory activity IC50 value (nM) |
| --- | --- |
| 37 | 70.5 |
| 39 | 37.5 |

TABLE 19-continued

| Example No. | EGFR inhibitory activity IC50 value (nM)/BTK inhibitory activity IC50 value (nM) |
|---|---|
| 40 | 10.0 |
| 42 | 19.4 |
| 44 | 17.1 |
| 47 | 20.4 |
| 49 | 24.8 |
| 50 | 22.1 |
| 51 | 31.1 |
| 52 | 20.6 |
| 53 | 25.5 |
| 54 | 37.1 |
| 56 | 17.6 |
| 57 | 19.3 |
| 58 | 23.5 |
| 59 | 16.3 |
| 60 | 32.4 |
| 61 | 67.5 |
| Reference compound 1 | 1.3 |

From these test results, it was made clear that the selectivity of the compound of the present invention to BTK inhibition over EGFR kinase in vitro was about 7.5 times or more compared with that of the Reference compound 1, and the compounds of the present invention have an excellent BTK inhibition selectivity. These results show that the compounds of the present invention can reduce adverse effects compared with existing BTK inhibitors.

Test Example 3 Test for Measuring Proliferation Inhibitory Activity Against Cell Lines Expressing BTK and EGFR (In Vitro), and Comparison of its Selectivity TMD8 cells, which are of a diffuse large B-cell lymphoma cell line expressing BTK, were suspended in RPMI1640 medium (Life Technologies Corp.) containing 10% fetal bovine serum. A431 cells, which are of an EGFR-overexpressing, highly activated human epidermoid carcinoma cell line, were suspended in DMEM, high glucose medium (Life Technologies Corp.) containing 10% fetal bovine serum. The cell suspensions were inoculated into each well of 384-well flat-bottomed microplates, and the cells were cultured for one day at 37° C. in an incubator containing 5% carbon dioxide gas. The compounds of the present invention and Reference compound 1 were each dissolved in DMSO, and the solutions were diluted to a concentration of 500 times the final concentration of the test compound with DMSO. A DMSO solution of the test compounds was diluted with the medium used in the suspension of the each cell, and this was added to each of the wells of the cell culture plates such that the final concentration of DMSO would be 0.2%. The cells were further cultured for three days at 37° C. in an incubator containing 5% carbon dioxide gas. Counting of the number of cells before the addition of the compounds and after the culture for three days in the presence of the compounds, was carried out with a CELL-TITER GLO (Promega Corp.) on the basis of the protocol recommended by Promega Corp. The proliferation inhibition ratio was calculated by the following formula, and the concentration of the test compound inhibiting 50% (GI50 (nM)) was determined.

Proliferation inhibition ratio (%)=$(C-T)/(C-C0) \times 100$

T: Luminescence intensity of a well in which the test compound was added
C: Luminescence intensity of a well in which the test compound was not added
C0: Luminescence intensity of a well measured before the addition of the test compound When a comparison is made between the cell proliferation inhibitory activity against A431 cells that depends on the EGFR proliferation signaling and the cell proliferation inhibitory activity against TMD8 cells that depends on the BTK proliferation signaling, the influence of the respective kinases at a cellular level is able to be evaluated. That is, when the "A431 cell proliferation inhibition ratio/TMD8 cell proliferation inhibition ratio" is calculated, it is contemplated that as the value of the ratio is larger, the selectivity to BTK over EGFR in the cells is higher. The values of "A431 cell proliferation inhibition ratio/TMD8 cell proliferation inhibition ratio" are indicated in Table 20 and Table 21.

TABLE 20

| Example No. | A431 cell proliferation inhibition ratio/TMD8 cell proliferation inhibition ratio |
|---|---|
| 1 | 1062.9 |
| 2 | >1033.6 |
| 6 | 2786.0 |
| 7 | 5440.9 |
| 8 | 25303.8 |
| 9 | 8196.7 |
| 10 | 5860.5 |
| 12 | 3077.4 |
| 13 | 4872.2 |
| 14 | >1400.6 |
| 15 | 16442.0 |
| 16 | >16313.2 |
| 17 | >12345.7 |
| 18 | >15625.0 |
| 19 | >17825.3 |
| 20 | >19120.5 |
| 21 | 4909.1 |
| 22 | >12468.8 |
| 23 | >10680 |
| 24 | 3266.5 |
| 25 | 2793.0 |
| 27 | 4155.9 |
| 28 | 2040.3 |
| 29 | 1243.4 |
| 30 | 5164.3 |
| 32 | >11123.5 |
| 33 | >18281.5 |
| 34 | >22471.9 |
| 35 | >18691.6 |
| 38 | 2868.1 |
| 39 | >3510.0 |
| 40 | >3159.6 |
| 41 | 1667.7 |
| 42 | 3934.1 |

TABLE 21

| Example No. | A431 cell proliferation inhibition ratio/TMD8 cell proliferation inhibition ratio |
|---|---|
| 44 | 10905.1 |
| 46 | 7662.2 |
| 48 | 2496.4 |
| 49 | >3260.5 |
| 50 | >2767.8 |
| 51 | >2044.6 |

TABLE 21-continued

| Example No. | A431 cell proliferation inhibition ratio/TMD8 cell proliferation inhibition ratio |
|---|---|
| 52 | >3617.9 |
| 53 | >1535.4 |
| 54 | >2675.9 |
| Reference compound 1 | 117.9 |

From these test results, it was made clear that the BTK inhibition selectivity of the compounds of the present invention over EGFR kinase in the cell proliferation inhibition ratio (in vitro) is about 8.5 times or more compared with the Reference compound 1, and the compounds of the present invention also have an excellent BTK inhibition selectivity not only in kinase levels but also in cellular levels. These results show that the compounds of the present invention can reduce adverse effects compared with existing BTK inhibitors.

Test Example 4 Inhibitory Activity Against B-Cell Activation Using Ramos Cells

The human B-cell lymphoma-derived cell line, Ramos cells were suspended in RPMI1640 medium, and then the cells were inoculated in a culture plate at a concentration of $2.0\times10^6$ (cells/well). The cells were cultured in a $CO_2$ incubator (Sanyo Electric Biomedical Co., Ltd.) at 37° C. for 12 hours. Each of Reference compound 1, Example Compound 12, and Example Compound 13 was diluted stepwise with DMSO, the dilution was added to the plate inoculated with cells, and the cells were cultured in a $CO_2$ incubator for 1 hour. Then, 10 minutes of stimulation was provided with Goat F(ab')2 anti-human IgM antibody-UNLB (southern biotech Corp.). Thereafter, the cells were harvested, and 50 μL of (a cell extract (NP-40; Invitrogen, Inc.) containing 1×protease inhibitor (Hoffmann-La Roche AG) and 1×phosphatase cocktail inhibitor (Sigma-Aldrich Co.)) was added to the cell pellets. The cell pellets were left to stand for 10 minutes on ice. The amount of protein in the collected cell extract was quantitatively analyzed by a DC protein assay (Bio-Rad Laboratories, Inc.), and 20 μg of proteins per lane was applied to a Criterion TGX™ (Bio-Rad Laboratories, Inc.). After electrophoresis was performed, Western blotting was performed with Trans-Blot™ Turbo™ (Bio-Rad Laboratories, Inc.). Thereafter, phosphorylated BTK protein and BTK protein were detected with LAS4000 (GE Healthcare, Inc.) with a BTK phosphor (pY223) antibody (EPITOMICS Inc.) and a BTK antibody (Abcam, plc.). Then, a ratio of phosphorylated BTK protein to BTK protein was obtained from a luminescence intensity of each of the detected proteins, and the compound concentration at which the phosphorylated BTK protein could be suppressed in 50% was defined as the IC50 value (nM). Table 22 shows the phosphorylated BTK inhibitory concentration (IC50; (nM)).

Table 22 showed that Reference compound 1 exhibited the BTK phosphorylation inhibition at 0.70 (nM), while the compounds of the present invention exhibited equivalent or higher BTK phosphorylation inhibitions, and it was found that the compounds of the present invention inhibit an activation signal of a B-cell through a stimulation of a B-cell receptor.

Rituxan targeted to B-cell is known to exhibit an effect in autoimmune diseases induced by autoantibodies, including rheumatoid arthritis (Non-Patent Literature: Rastetter et al., Annu Rev Med, 55, 2004).

Since it was confirmed from the test that the compounds of the present invention suppress an activation of a B-cell through a stimulation of a B-cell receptor, the compounds of the present invention were considered to exhibit an excellent drug efficacy against autoimmune diseases associated with B cell involved in autoantibody production.

TABLE 22

| Example No. | Phosphorylated BTK inhibitory concentration (IC50; (nM)) |
|---|---|
| 12 | 0.18 |
| 13 | 0.25 |
| Reference compound 1 | 0.70 |

Test Example 5 Inhibitory Activity Against Allergic Reaction Using RBL-2H3 Cells Rat basophilic leukemia cells, RBL-2H3, were suspended in MEM medium containing 10% FBS, and then the cells were inoculated in a culture plate, and cultured in a $CO_2$ incubator (Sanyo Electric Biomedical Co., Ltd.) at 37° C. for 12 hours. After a culture supernatant was removed and the cells were washed, an anti-DNP-mouse IgE (Alpha Diagnostic Inc.) solution was added thereto, and the cells were cultured in the $CO_2$ incubator for 1 hour. After a culture supernatant was removed and the cells were washed, an MEM medium was added thereto. Each of Reference Compound 1, Example Compound 1, Example Compound 12, and Example Compound 13 was diluted stepwise with DMSO, the dilution was added to the plate inoculated with cells, and the cells were cultured in the $CO_2$ incubator for 30 minutes.

Further, a DNP-BSA (LSL, Inc.) solution was added thereto and the cells were cultured in the $CO_2$ incubator for 15 minutes. A culture supernatant was collected and reacted, with $PGD_2$-MOX EIA kit (Cayman Chemical Inc.) on the basis of the protocol attached thereto, and absorbance was measured by SUNRISE RAINBOW THERMO (TECAM Inc.). Amount of $PGD_2$ in the culture supernatant was calculated on the basis of the measured absorbance, and the compound concentration at which the $PGD_2$ production amount could be suppressed by 50% compared to the control was defined as the IC50 value (nM). Table 23 shows the concentrations at which the $PGD_2$ production is inhibited (IC50; (nM)).

Table 23 showed that Reference compound 1 exhibited a $PGD_2$ production inhibition at about 350 (nM), while the compounds of the present invention exhibited $PGD_2$ production inhibition property far stronger than that of Reference compound 1.

When IgE antibodies are bound to FCε receptors on mast cells, and those antibodies are cross-linked by an antigen, the mast cells are activated and various chemical mediators (histamine, $PGD_2$, or leukotriene) are excreted or secreted. These are known to be significantly associated with incidence of allergic diseases, for example, bronchial asthma and allergic rhinitis (Non-Patent Literature: Ellmeier W., et al., FEBS Journal., 278, 2011).

Since it was confirmed that the compounds of the present invention regulate the excretion or secretion of the chemical mediators of mast cells in the downstream of the FCε receptor, the compounds of the present invention were considered to exhibit an excellent drug efficacy against allergic diseases.

TABLE 23

| Example No. | PGD$_2$ production inhibitory concentration (IC50; (nM)) |
|---|---|
| 1 | 37 |
| 12 | 15 |
| 13 | 26 |
| Reference compound 1 | 348 |

Test Example 6 Mouse Collagen-Induced Arthritis Model (Preventive Effect)

The test was carried out in accordance with the method described in Non-Patent Literature (Brand D D, et al., Nat Protoc. 2007; 2, 1269-1275, Xu D. et al., JPET, 2012 April; 341(1): 90-103). Seven-week-old male/DBA/1 mice (CHARLES RIVER LABORATORIES JAPAN, INC.) were intracutaneously injected in the dorsum with 100 μL/body of an equal amount-mixed solution (emulsion) of a 4 mg/mL bovine type 2 collagen solution (Collagen Research Center) and a complete freund's adjuvant (DIFCO Inc.) (Initial immunization). After 21 days therefrom, the mice were intracutaneously injected in the base of the tail with 100 μL/body of the equal amount-mixed solution (emulsion) of a 4 mg/mL bovine type 2 collagen solution (Collagen Research Center) and a complete freund's adjuvant (DIFCO Inc.) to carry out an additional immunization. Once-a-day oral administration of Vehicle, Example Compound 12, Example Compound 13, or Reference compound 1 was continued for 21 days including the day in which the additional immunization was carried out (set as day 0). Symptoms of arthritis in day 0, day 4, day 7, day 10, day 14, day 17, and day 21 were scored with the naked eye (0: No change, 1: Swelling of one finger, 2: Swelling of two fingers or more, 3: Swelling of instep, 4: Swelling of all fingers besides swelling extending to wrist/ankle), and a total of four limbs was obtained as a point of an individual (maximum 16 points) to compare the effect in the same model in each of the administration groups. The results are shown in FIG. 1.

From FIG. 1, it has been confirmed that the compounds of the present invention completely suppressed increase of the arthritis score after the additional immunization, compared to Reference compound 1, and that the compounds of the present invention have an excellent preventing effect against incidence of rheumatoid arthritis. Incidentally, toxicity causing, for example, a remarkable decrease in body weight or skin disorders including epilation was not observed at the doses of the Example Compounds used in the test.

Test Example 7 Mouse Collagen-Induced Arthritis Model (Therapeutic Effect)

The test was carried out in accordance with the method described in Non-Patent Literature (Brand D D, et al., Nat Protoc. 2007; 2, 1269-1275, Xu D. et al., JPET, 2012 April; 341(1): 90-103). Seven-week-old male/DBA/1 mice (CHARLES RIVER LABORATORIES JAPAN, INC.) were intracutaneously injected in the dorsum with 100 μL/body of an equal amount-mixed solution (emulsion) of a 4 mg/mL bovine type 2 collagen solution (Collagen Research Center) and a complete freund's adjuvant (DIFCO Inc.) (Initial immunization). After 21 days therefrom, the mice were intracutaneously injected in the base of the tail with 100 μL/body of the equal amount-mixed solution (emulsion) of a 4 mg/mL of bovine type 2 collagen solution (Collagen Research Center) and a complete freund's adjuvant (DIFCO Inc.) to carry out an additional immunization. Once-a-day oral administration of Vehicle, Example Compound 13, or Reference compound 1 was continued for 15 days, setting the sixth day from the additional immunization as the administration initiation day (day 0). Symptoms of arthritis in day 0, day 4, day 7, day 11, and day 14 were scored with the naked eye (0: No change, 1: Swelling of a finger, 2: Swelling of two fingers or more, 3: Swelling of instep, 4: Swelling of all fingers besides swelling extending to wrist/ankle), and a total of four limbs was obtained as a point of an individual (maximum 16 points). The results are shown in FIG. 2.

Figure 2:
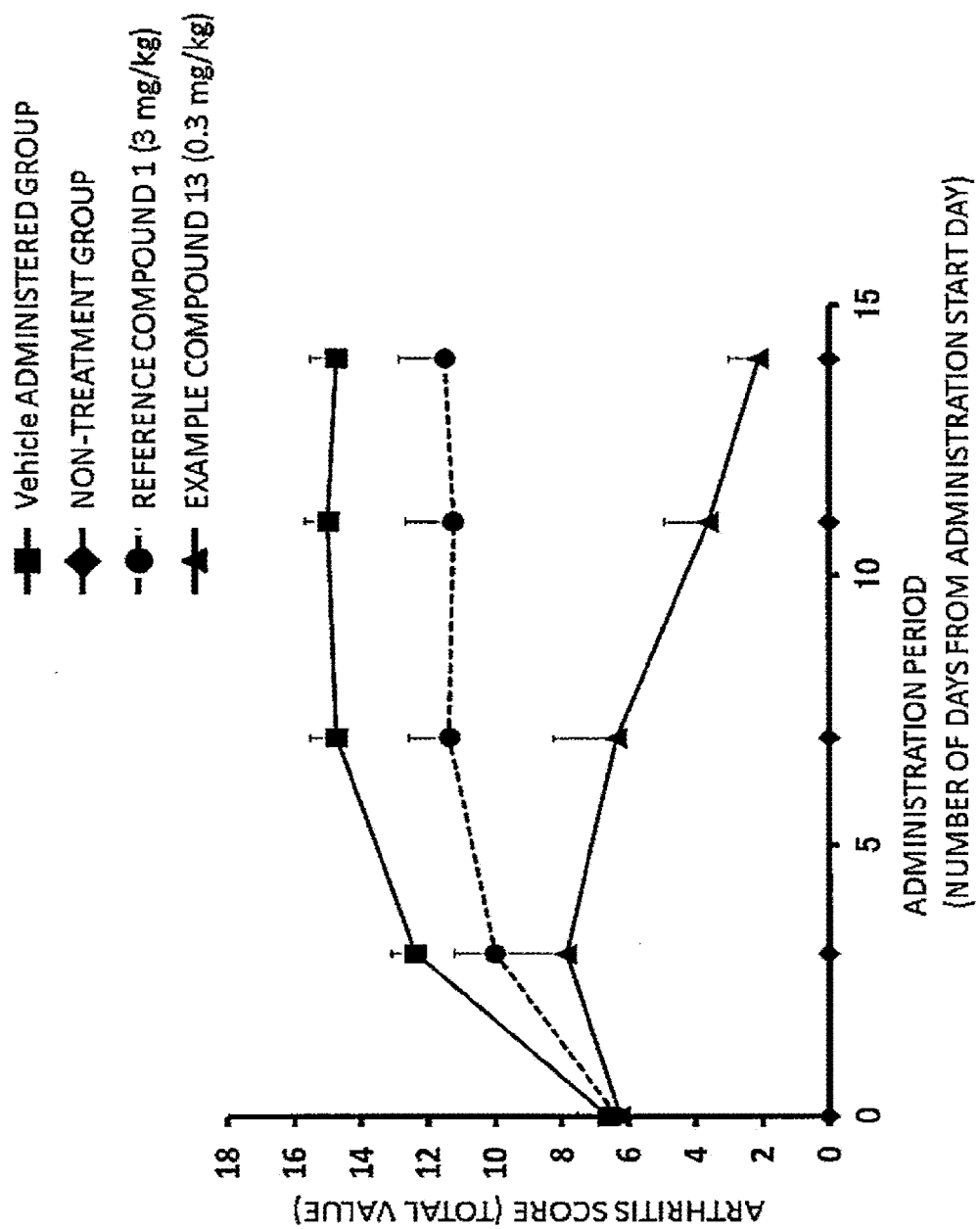
FIG. 2 illustrates effects in mouse collagen-induced arthritis models (therapeutic effect).

From FIG. 2, it has been confirmed that the compounds of the present invention decreased the arthritis score while Reference compound 1 delayed the further increase of the increased arthritis score, and that the compounds of the present invention have an excellent therapeutic effect against rheumatoid arthritis which has already established. Incidentally, toxicity causing, for example, a remarkable decrease in body weight or skin disorders including epilation was not recognized at the doses of the Example Compounds used in the test.

Test Example 8 Mouse Collagen-Induced Arthritis Model (Therapeutic Effect)

A test similar to Test example 7 was carried out, by using the Vehicle, Example Compound 12, and Reference compound 1. The results are shown in FIG. 3.

Figure 3:
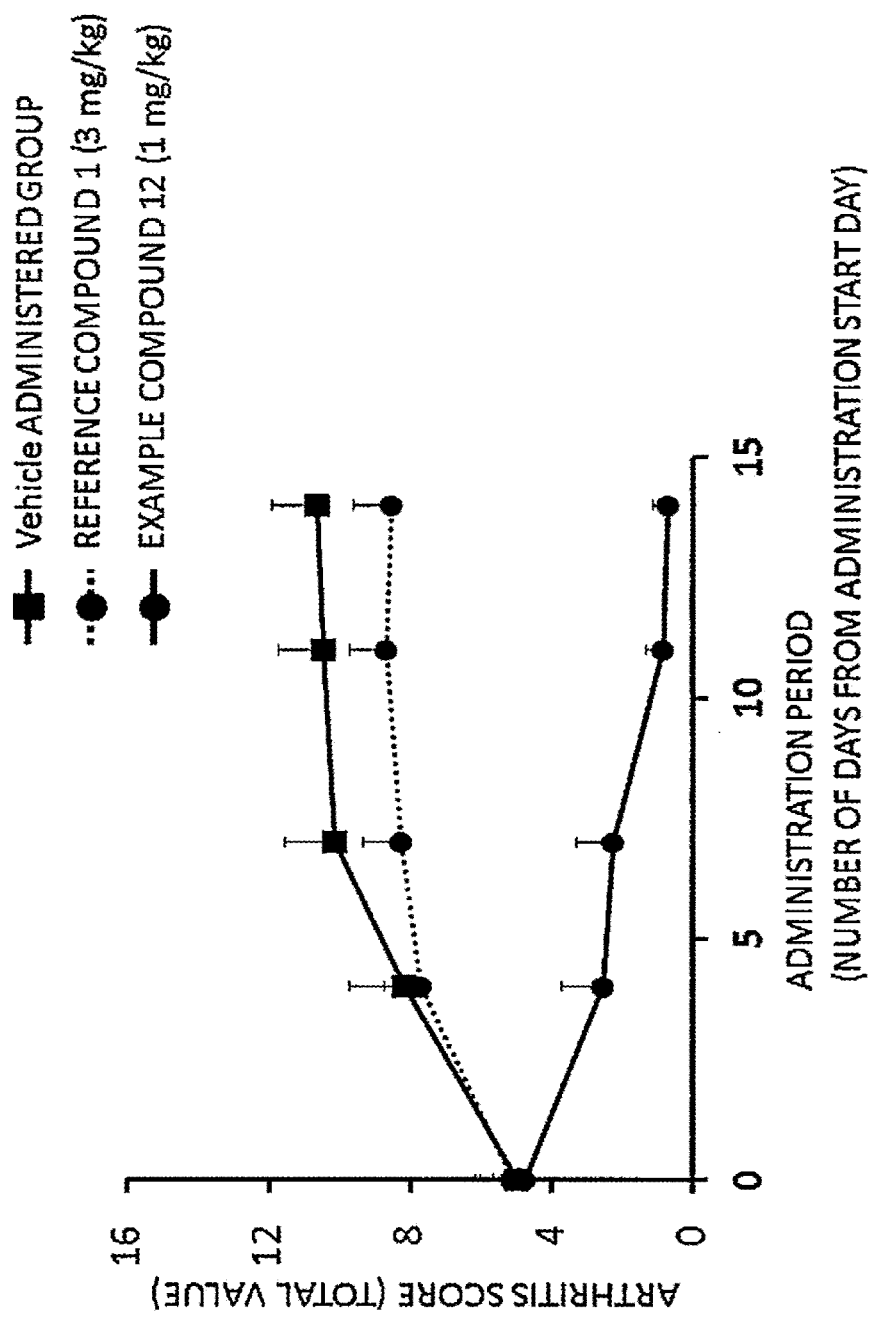
FIG. 3 illustrates effects in mouse collagen-induced arthritis models (therapeutic effect).

From FIG. 3, it has been confirmed that the compounds of the present invention remarkably decreased the arthritis score while Reference compound 1 delayed the further increase of the increased arthritis score, and that the compounds of the present invention have an excellent therapeutic effect against rheumatoid arthritis which has been already established. Incidentally, toxicity causing, for example, a remarkable decrease in body weight or skin disorders including epilation was not recognized at the doses of the Example Compounds used in the test.

Test Example 9 Mouse Antigen-Induced Dermatitis Model

Type I allergy models accompanied by a skin symptom (a dermatitis model) were produced, with TNP-IgE mice (CLEA Japan, Inc.). The mice are genetically modified BALB/c mice that constantly produce an IgE specific to hapten TNP (trinitrophenol) which is widely used as an allergen (antigen). It is possible to induce an allergic reaction in the mice, only by administering an allergen, without carrying out an immunization. An 0.025% acetone solution of picryl chloride (NACALAI TESQUE, INC.) which is an allergen was applied to ear skin of both ears of the mice at 10 μL/ear, and in 2 hours after the application of the antigen, thickenings of the ears were measured by a dial thickness gauge (Ozaki Mfg., PEACOCK G-2M). An average value of thickening values of both ears was obtained as a value of an individual (provided that a previous value before the allergen application was 0 mm). Vehicle, Reference compound 1, Example Compound 1, Example Compound 6, Example Compound 12, or Example Compound 13 was orally administered 30 minutes before the allergen application.

Ear swelling control ratio (%) was calculated by the following formula. The results are shown in Table 24.

Ear swelling control ratio (%)=(1−(Average value of ear thickening of compound administered group)/(Average value of ear thickening of vehicle administered group))×100

TABLE 24

| Example No. | Dosage (mg/kg) | Ear swelling (control ratio (%)) |
|---|---|---|
| 1 | 1 | 66 |
|  | 3 | 81 |
|  | 12.5 | 91 |
| 6 | 3 | 45 |
| 12 | 1 | 64 |
|  | 3 | 80 |
|  | 12.5 | 83 |
| 13 | 1 | 54 |
|  | 3 | 79 |
|  | 12.5 | 77 |
| Reference compound 1 | 12.5 | 49 |

From Table 24, it was confirmed that Example Compound 1, Example Compound 6, Example Compound 12, and Example Compound 13 suppressed equivalently or strongly ear swellings induced by the allergen application from low dose of each compound compared with Reference compound 1, and that the compounds of the present invention exhibit an excellent drug efficacy against atopic dermatitis.

Test Example 10 Guinea Pig Antigen-Induced Rhinitis Model

A type-I allergy model accompanied by a rhinocleisis (a rhinitis model) was produced, by using a guinea pig (Japan SLC, Inc.). The model is sensitized by subcutaneous administration with 1 mL/body of physiological saline containing 1 mg/mL ovalbumin (OVA solution) by use of a 1 mL syringe with 23 G needle, and the sensitization day was set as day 0. It is possible to induce an allergic reaction by administering each 20 μL of 10 mg/mL OVA solution to both of the nasal cavities on day 7, day 14 and day 21. A single oral administration of vehicle or Example Compound 13 was carried out two hours before the antigen induction of day 21. On day 20, resistance values in nasal cavities of the individuals were measured severally as a pre value of an individual, and on day 21, 15 minutes and 240 minutes after the antigen induction, the resistance values in nasal cavities were measured.

The resistance values in nasal cavities (change ratio; %) was calculated by the following formula. The results are shown in FIG. 4.

Resistance value in nasal cavity (change ratio; %)= ((Resistance values in nasal cavity of vehicle administered group or Example Compound administered group (15 min. or 240 min.; day 21))/(Resistance value in nasal cavity of vehicle administered group or Example Compound administered group (pre; day 20))−1)×100

Figure 4:
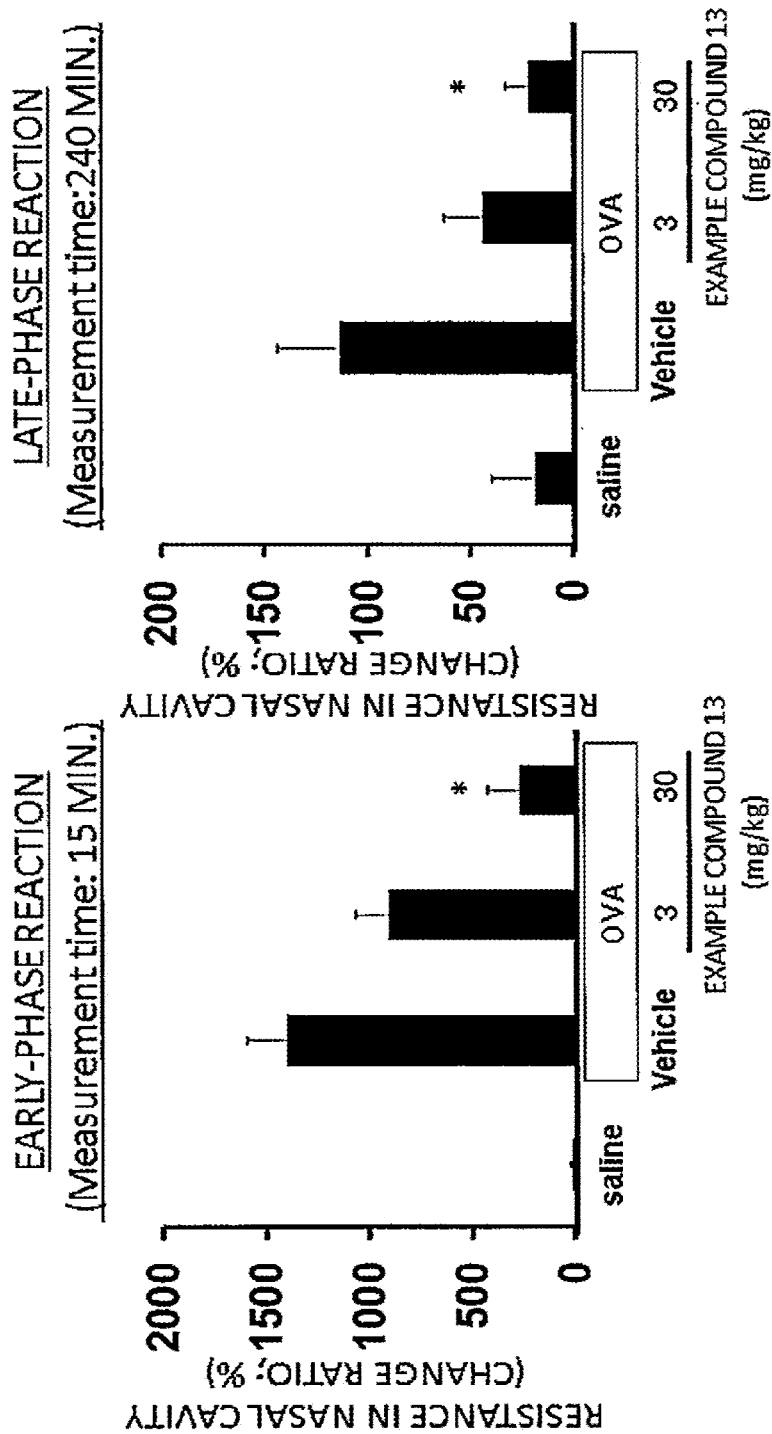
FIG. 4 illustrates effects in guinea pig antigen-induced rhinitis models.

Compared with the vehicle administered group that exhibited increases in the resistance in nasal cavities due to the antigen induction, Example Compound 13 suppressed the increase of the resistance in nasal cavities in the early phase and in the late phase in a dose-response fashion, according to FIG. 4. Thus, it has been confirmed that the compounds of the present invention exhibit an excellent efficacy against allergic rhinitis or pollinosis.

Test Example 11 Influence on Body Weight of SD Rat by Repeated Administration with the Compounds of the Present Invention (In Vivo)

The influence on the increase in the body weight of SD rats by repeated administration with Reference compound 1 and the compounds of the present invention for two weeks, was compared with that of a vehicle-administered group. The rats were grouped as follows, with four animals in each group, by a random classification method such that the average body weights of the respective groups would be almost uniform (Day 1).

Group 1: Reference compound 1 (280 mg/kg) was orally administered once a day, Group 2: Example Compound 12 (750 mg/kg) was orally administered once a day, and Group 3: Example Compound 13 (750 mg/kg) was orally administered once a day.

The body weight change (BWC) was used as an index indicating the systemic toxicity caused by the compound administration. The BWC was calculated by the following formula.

BWC (%)=([(Rat body weight on 14 days after the administration)−(Rat body weight at the time of grouping)]/(Rat body weight at the time of grouping))×100

The relative body weight change ratios in the each compound-administered groups were calculated by the following formula when the BWC in the vehicle-administered group was set as 1, and the results are indicated in Table 25.

Relative body weight change ratio (%)=(BWC in the compound-administered group)/BWC in the vehicle-administered group)×100

TABLE 25

|  | Dosage (mg/kg) | Relative body weight change ratio (%) |
|---|---|---|
| Group 1 | 280 | 30.9 |
| Group 2 | 750 | 91.2 |
| Group 3 | 750 | 79.1 |

According to the results, the width of rat body weight increase was very small in Group 1, which was the Reference compound 1-administered group compared with the vehicle-administered group. Whereas in Groups 2 and 3, which were the groups administered the compounds of the present invention, the increase of the rat body weight was hardly affected. The compounds of the present invention were administered with a 2.5-fold or more the amount of the Reference compound 1 (an approximately 5-fold amount in terms of $AUC_{0-24}$ (μM: hr)). Furthermore, in Group 1, individuals suffering from loose bowel were recognized; however, in Groups 2 and 3, no such individuals were recognized. Therefore, the compounds of the present invention have an excellent effect that the level of adverse effects is low despite that the amount of exposure is far larger than that of the Reference compound 1.

As described above, it was made clear that the compounds of the present invention are compounds having superior profiles with reduced toxicity compared with the Reference compound 1.

Test Example 12 Mouse Systematic Lupus Erythematosus Model

MRL/lpr mice (Japan SLC, Inc.) were used to evaluate drug efficacy in this test, since the mice are widely used as mice models in which symptoms of autoimmune diseases similar to human systemic lupus erythematosus spontaneously express. A grouping was carried out on the basis of swellings of lymph nodes in submaxilla and axilla at 14 weeks old, and once-daily oral administration was continued for 42 days from the day of grouping, with vehicle or Example Compound 13 suspension. Urea nitrogen concentration and anti-dsDNA antibody concentration in peripheral blood at the final administration day were measured. The results are shown in FIG. 5.

Figure 5:
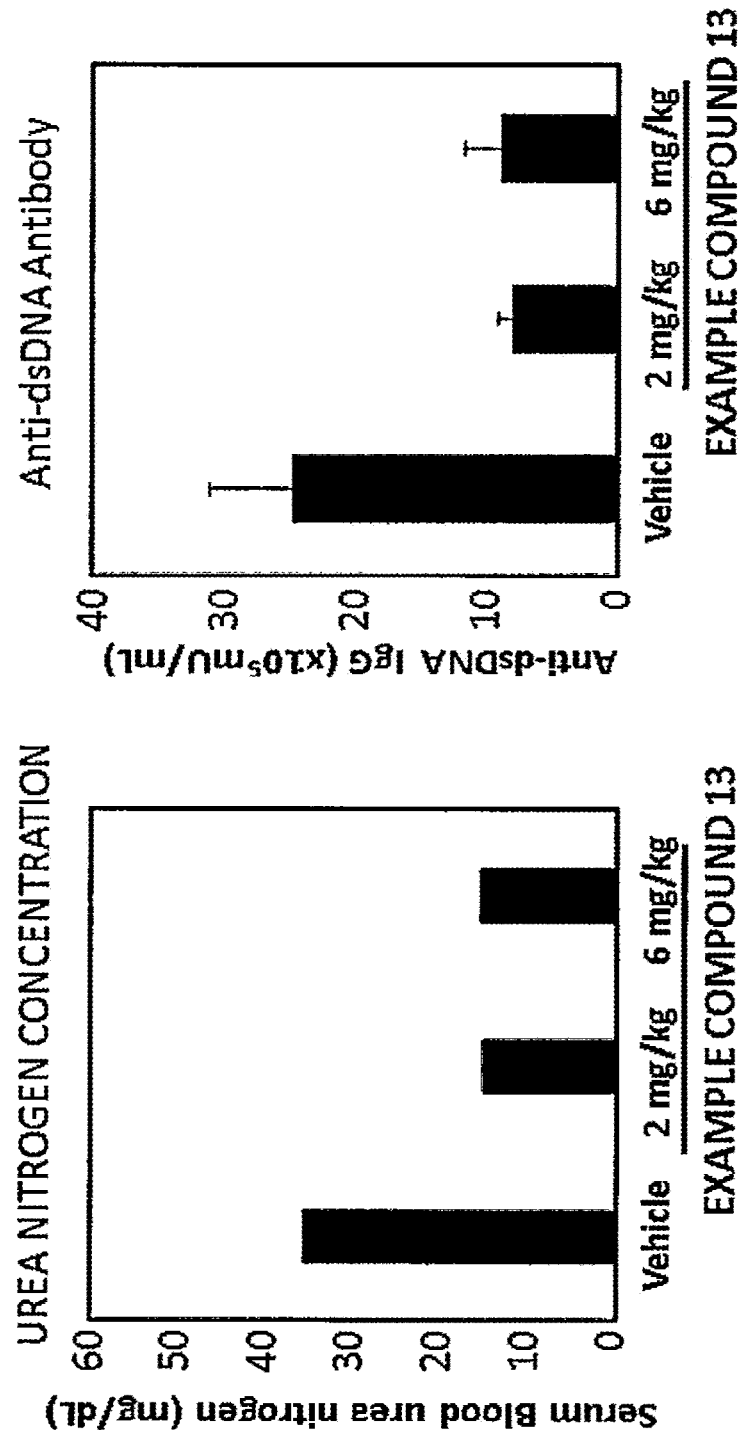
FIG. 5 illustrates effects in mouse systemic lupus erythematosus models.

From FIG. 5, it has been confirmed that Example Compound 13 suppressed the increased urea nitrogen which was a renal function marker or the increased anti-dsDNA antibody which was an autoantibody compared with the vehicle administered group, and that the compounds of the present invention exhibit an excellent efficacy against a systemic lupus erythematosus which has been already established. Incidentally, a remarkable decrease in body weight was not recognized at the doses of the Example Compound used in the test.

The invention claimed is:

1. A method for treating an immune disease, comprising: administering an effective amount of a compound of the formula (I) or a salt thereof to an object in need thereof,

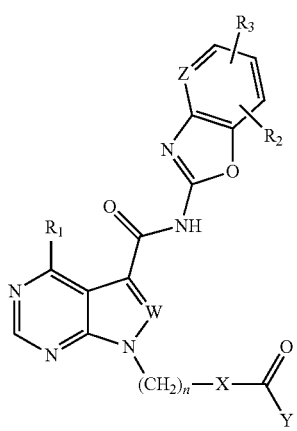

(I)

wherein X represents a nitrogen-containing C3-C10 heterocycloalkylene optionally having one or more substituents;
Y represents —C($R_4$)=C($R_5$)($R_6$) or —C≡C—$R_7$;
W and Z each independently represent N or CH;
n represents an integer from 0 to 2;
$R_1$ represents an amino group which optionally has one or more substituents;
$R_2$ and $R_3$, which are identical or different, each represent a hydrogen atom, a halogen atom, a C1-C6 alkyl group which optionally has one or more substituents, a C1-C6 alkoxy group which optionally has one or more substituents, a C3-C7 cycloalkyl group which optionally has one or more substituents, a C6-C14 aromatic hydrocarbon group which optionally has one or more substituents, a 4- to 10-membered monocyclic or polycyclic unsaturated heterocyclic group containing 1 to 3 heteroatoms of the same kind or different kinds selected from the group consisting of a nitrogen atom, an oxygen atom and a sulfur atom, which optionally has one or more substituents, or a cyano group; and $R_4$, $R_5$, $R_6$ and $R_7$, which are identical or different, each represent a hydrogen atom, or a C1-C6 alkyl group which optionally has one or more substituents.

2. The method of claim 1, wherein in the formula (I),
X represents a nitrogen-containing C3-C10 heterocycloalkylene;
n represents 0; and
$R_1$ represents an amino group.

3. The method of claim 1, wherein in the formula (I),
X represents azetidinylene, pyrrolidinylene, or piperidinylene;
n represents 0; and
$R_1$ represents an amino group.

4. The method according to of claim 1, wherein in the formula (I),
X represents azetidinylene, pyrrolidinylene, or piperidinylene;
Y represents —C($R_4$)=C($R_5$)($R_6$) or —C≡C—$R_7$;
n represents 0;
$R_1$ represents an amino group;
one of $R_2$ and $R_3$ represents a hydrogen atom or a C1-C6 alkyl group, and the other represents a hydrogen atom, a halogen atom, a C1-C6 alkyl group, a halogeno-C1-C6 alkyl group, a C1-C4 alkoxy-substituted C1-C6 alkyl group, a C1-C6 alkoxy group, a phenyl group which optionally has one or more substituents with a halogen atom, a 4- to 6-membered monocyclic unsaturated heterocyclic group containing one sulfur atom, or a cyano group;
when Y represents —C($R_4$)=C($R_5$)($R_6$),
$R_4$, $R_5$ and $R_6$, which are identical or different, each represent a hydrogen atom, a C1-C6 alkyl group, a C1-C6 alkyl group that is substituted with an amino group substituted with two C1-C6 alkyl groups, where the C1-C6 alkyl groups optionally form a 4- to 8-membered heterocycloalkyl group together with the nitrogen atom to which these alkyl groups are bonded; and
when Y represents —C≡C—$R_7$,
$R_7$ represents a hydrogen atom or a C1-C6 alkyl group.

5. The method of claim 1, wherein in the formula (I),
X represents 1,3-azetidinylene, 1,3-pyrrolidinylene, or 1,3-piperidinylene;
Y represents —C($R_4$)=C($R_5$)($R_6$) or —C≡C—$R_7$;
when Z represents N, W represents N, and when Z represents CH, W represents N or CH;
n represents 0;
$R_1$ represents an amino group;
one of $R_2$ and $R_3$ represents a hydrogen atom or a C1-C4 alkyl group, and the other represents a hydrogen atom, a halogen atom, a C1-C4 alkyl group, a halogeno-C1-C4 alkyl group, a C1-C4 alkoxy-substituted C1-C4 alkyl group, a C1-C4 alkoxy group, a phenyl group which optionally has one or more substituents with a halogen atom, a 4- to 6-membered monocyclic unsaturated heterocyclic group containing one sulfur atom, or a cyano group;
when Y represents —C($R_4$)=C($R_5$)($R_6$),
$R_4$, $R_5$ and $R_6$, which are identical or different, each represent a hydrogen atom, a C1-C6 alkyl group, a C1-C6 alkyl group that is substituted with an amino group substituted with two C1-C6 alkyl groups, where the C1-C6 alkyl groups optionally form a 4- to 8-membered heterocycloalkyl group together with the nitrogen atom to which these alkyl groups are bonded; and
when Y represents —C≡C—$R_7$,
$R_7$ represents a hydrogen atom or a C1-C4 alkyl group.

6. The method according to claim 1, wherein in the formula (I),

X represents 1,3-azetidinylene, 1,3-pyrrolidinylene, or 1,3-piperidinylene;

Y represents —C($R_4$)=C($R_5$)($R_6$) or —C≡C—$R_7$;

when Z represents N, W represents N, and when Z represents CH, W represents N or CH;

n represents 0;

$R_1$ represents an amino group;

one of $R_2$ and $R_3$ represents a hydrogen atom or a methyl group, and the other represents a hydrogen atom, a halogen atom, a methyl group, a trifluoromethyl group, a methoxyethyl group, a methoxy group, a phenyl group, a 4-chlorophenyl group, a 2-thienyl group, or a cyano group;

when Y represents —C($R_4$)=C($R_5$)($R_6$), $R_4$, $R_5$ and $R_6$, which are identical or different, each represent a hydrogen atom, a methyl group, a dimethylaminomethyl group, a methylethylaminomethyl group, a diethylaminomethyl group, a methylisopropylaminomethyl group, a 1-piperidinylmethyl group, or a 1-pyrrolidinylmethyl group; and when Y represents —C≡C—$R_7$, $R_7$ represents a methyl group.

7. The method according to claim 1, wherein in the formula (I),
  (1) when Z represents N, and W represents N,
    X represents 1,3-piperidinylene, and
    Y represents a vinyl group;
  (2) when Z represents CH, and W represents N,
    X represents 1,3-pyrrolidinylene or 1,3-piperidinylene, and
    Y represents —C($R_4$)=C($R_5$)($R_6$) or —C≡C—($R_7$), and
    when Y represents —C($R_4$)=C($R_5$)($R_6$),
    $R_4$, $R_5$ and $R_6$, which are identical or different, each represent a hydrogen atom, a methyl group, a dimethylaminomethyl group, a methylethylaminomethyl group, a diethylaminomethyl group, a methylisopropylaminomethyl group, a 1-piperidinylmethyl group, or a 1-pyrrolidinylmethyl group;
    when Y represents —C≡C—($R_7$),
    $R_7$ represents a methyl group; and
  (3) when Z represents CH, and W represents CH,
    X represents 1,3-azetidinylene or 1,3-pyrrolidinylene, and
    Y represents —C($R_4$)=C($R_5$)($R_6$), and
    $R_4$, $R_5$ and $R_6$, which are identical or different, each represent a hydrogen atom, a dimethylaminomethyl group, a methylethylaminomethyl group, a diethylaminomethyl group, a methylisopropylaminomethyl group, a 1-piperidinylmethyl group, or a 1-pyrrolidinylmethyl group;
    n represents 0;
    $R_1$ represents an amino group;
    one of $R_2$ and $R_3$ represents a hydrogen atom or a methyl group, and the other represents a hydrogen atom, a halogen atom, a trifluoromethyl group, a methoxyethyl group, a phenyl group, a 2-thienyl group, or a cyano group.

8. The method of claim 1, wherein in the formula (I),
X represents 1,3-piperidinylene;
Y represents a vinyl group;
Z represents CH;
W represents N;
n represents 0;
$R_1$ represents an amino group; and
one of $R_2$ and $R_3$ represents a hydrogen atom, and the other represents a hydrogen atom, a halogen atom, or a cyano group.

9. The method of claim 1, wherein the compound of the formula (I) or a salt thereof is selected from the group consisting of:
  (1) (R)-1-(1-acryloylpiperidin-3-yl)-4-amino-N-(5-chlorobenzo[d]oxazol-2-yl)-1H-pyrazolo[3,4-d]pyrimidine-3-carboxamide,
  (2) (R)-1-(1-acryloylpiperidin-3-yl)-4-amino-N-(5-bromobenzo[d]oxazol-2-yl)-1H-pyrazolo[3,4-d]pyrimidine-3-carboxamide,
  (3) (R)-1-(1-acryloylpiperidin-3-yl)-4-amino-N-(5-(thiophen-2-yl)benzo[d]oxazol-2-yl)-1H-pyrazolo[3,4-d]pyrimidine-3-carboxamide,
  (4) (R)-4-amino-N-(5-chlorobenzo[d]oxazol-2-yl)-1-(1-methacryloylpiperidin-3-yl)-1H-pyrazolo[3,4-d]pyrimidine-3-carboxamide,
  (5) (R,E)-4-amino-N-(5-chlorobenzo[d]oxazol-2-yl)-1-(1-(but-2-enoyl)piperidin-3-yl)-1H-pyrazolo[3,4-d]pyrimidine-3-carboxamide,
  (6) (R)-1-(1-acryloylpiperidin-3-yl)-4-amino-N-(5-cyanobenzo[d]oxazol-2-yl)-1H-pyrazolo[3,4-d]pyrimidine-3-carboxamide,
  (7) (R)-1-(1-acryloylpiperidin-3-yl)-4-amino-N-(5-methoxybenzo[d]oxazol-2-yl)-1H-pyrazolo[3,4-d]pyrimidine-3-carboxamide,
  (8) (R)-1-(1-acryloylpiperidin-3-yl)-4-amino-N-(5-(2-methoxyethyl)benzo[d]oxazol-2-yl)-1H-pyrazolo[3,4-d]pyrimidine-3-carboxamide,
  (9) (R)-1-(1-acryloylpiperidin-3-yl)-4-amino-N-(oxazolo[4,5-b]pyridin-2-yl)-1H-pyrazolo[3,4-d]pyrimidine-3-carboxamide,
  (10) (R)-1-(1-acryloylpiperidin-3-yl)-4-amino-N-(4-methylbenzo[d]oxazol-2-yl)-1H-pyrazolo[3,4-d]pyrimidine-3-carboxamide,
  (11) (R)-4-amino-N-(5-fluorobenzo[d]oxazol-2-yl)-1-(1-methacryloylpiperidin-3-yl)-1H-pyrazolo[3,4-d]pyrimidine-3-carboxamide,
  (12) (R)-1-(1-acryloylpiperidin-3-yl)-4-amino-N-(5-fluorobenzo[d]oxazol-2-yl)-1H-pyrazolo[3,4-d]pyrimidine-3-carboxamide,
  (13) (R)-1-(1-acryloylpiperidin-3-yl)-4-amino-N-(benzo[d]oxazol-2-yl)-1H-pyrazolo[3,4-d]pyrimidine-3-carboxamide,
  (14) (R,E)-4-amino-N-(benzo[d]oxazol-2-yl)-1-(1-(but-2-enoyl)piperidin-3-yl)-1H-pyrazolo[3,4-d]pyrimidine-3-carboxamide,
  (15) (R,E)-4-amino-N-(5-chlorobenzo[d]oxazol-2-yl)-1-(1-(4-(dimethylamino)but-2-enoyl)piperidin-3-yl)-1H-pyrazolo[3,4-d]pyrimidine-3-carboxamide,
  (16) (R,E)-4-amino-N-(5-chlorobenzo[d]oxazol-2-yl)-1-(1-(4-ethyl(methyl)amino)but-2-enoyl)piperidin-3-yl)-1H-pyrazolo[3,4-d]pyrimidine-3-carboxamide,
  (17) (R,E)-4-amino-N-(5-chlorobenzo[d]oxazol-2-yl)-1-(1-(4-di ethylamino)but-2-enoyl)piperidin-3-yl)-1H-pyrazolo[3,4-d]pyrimidine-3-carboxamide,
  (18) (R,E)-4-amino-N-(5-chlorobenzo[d]oxazol-2-yl)-1-(1-(4-isopropyl(methyl)amino)but-2-enoyl)piperidin-3-yl)-1H-pyrazolo[3,4-d]pyrimidine-3-carboxamide,
  (19) (R,E)-4-amino-N-(5-chlorobenzo[d]oxazol-2-yl)-1-(1-(4-(pyrrolidin-1-yl)but-2-enoyl)piperidin-3-yl)-1H-pyrazolo[3,4-d]pyrimidine-3-carboxamide,
  (20) (R,E)-4-amino-N-(5-chlorobenzo[d]oxazol-2-yl)-1-(1-(4-(piperidin-1-yl)but-2-enoyl)piperidin-3-yl)-1H-pyrazolo[3,4-d]pyrimidine-3-carboxamide,

(21) (R,E)-4-amino-N-(5-(thiophen-2-yl)benzo[d]oxazol-2-yl)-1-(1-(4-(dimethylamino)but-2-enoyl)piperidin-3-yl)-1H-pyrazolo[3,4-d]pyrimidine-3-carboxamide,

(22) (R)-4-amino-N-(benzo[d]oxazol-2-yl)-1-(1-but-2-ynoyl)piperidin-3-yl)-1H-pyrazolo[3,4-d]pyrimidine-3-carboxamide,

(23) (R)-1-(1-acryloylpiperidin-3-yl)-4-amino-N-(5,6-dimethylbenzo[d]oxazol-2-yl)-1H-pyrazol o[3,4-d]pyrimidine-3-carboxamide,

(24) (R)-1-(1-acryloylpyrrolidin-3-yl)-4-amino-N-(5-chlorobenzo[d]oxazol-2-yl)-1H-pyrazolo[3,4-d]pyrimidine-3-carboxamide,

(25) (R,E)-4-amino-N-(5-chlorobenzo[d]oxazol-2-yl)-1-(1-(but-2-enoyl)pyrrolidin-3-yl)-1H-pyrazolo[3,4-d]pyrimidine-3-carboxamide,

(26) (R,E)-4-amino-N-(5-chlorobenzo[d]oxazol-2-yl)-1-(1-(3-methylbut-2-enoyl)pyrrolidin-3-yl)-1H-pyrazolo[3,4-d]pyrimidine-3-carboxamide,

(27) (R)-1-(1-acryloylpyrrolidin-3-yl)-4-amino-N-(benzo[d]oxazol-2-yl)-1H-pyrazolo[3,4-d]pyrimidine-3-carboxamide,

(28) (R)-1-(1-acryloylpyrrolidin-3-yl)-4-amino-N-(5-(thiophen-2-yl)benzo[d]oxazol-2-yl)-1H-pyrazolo[3,4-d]pyrimidine-3-carboxamide,

(29) (R)-1-(1-acryloylpyrrolidin-3-yl)-4-amino-N-(5-methylbenzo[d]oxazol-2-yl)-1H-pyrazolo[3,4-d]pyrimidine-3-carboxamide,

(30) (R)-1-(1-acryloylpyrrolidin-3-yl)-4-amino-N-(5-fluorobenzo[d]oxazol-2-yl)-1H-pyrazolo[3,4-d]pyrimidine-3-carboxamide,

(31) (R)-1-(1-acryloylpyrrolidin-3-yl)-4-amino-N chlorophenyl)benzo[d]oxazol-2-yl)-1H-pyrazolo[3,4-d]pyrimidine-3-carboxamide,

(32) (R,E)-4-amino-N-(5-chlorobenzo[d]oxazol-2-yl)-1-(1-(4-(dimethylamino)but-2-enoyl)pyrrolidin-3-yl)-1H-pyrazolo[3,4-d]pyrimidine-3-carboxamide,

(33) (R,E)-4-amino-N-(5-chlorobenzo[d]oxazol-2-yl)-1-(1-(4-ethyl(methyl)amino)but-2-enoyl)pyrrolidin-3-yl)-1H-pyrazolo[3,4-d]pyrimidine-3-carboxamide,

(34) (R,E)-4-amino-N-(5-chlorobenzo[d]oxazol-2-yl)-1-(1-(4-diethylamino)but-2-enoyl)pyrrolidin-3-yl)-1H-pyrazolo[3,4-d]pyrimidine-3-carboxamide,

(35) (R,E)-4-amino-N-(5-chlorobenzo[d]oxazol-2-yl)-1-(1-(4-isopropyl(methyl)amino)but-2-enoyl)pyrrolidin-3-yl)-1H-pyrazolo[3,4-d]pyrimidine-3-carboxamide,

(36) (R,E)-4-amino-N-(5-chlorobenzo[d]oxazol-2-yl)-1-(1-(4-(pyrrolidin-1-yl)but-2-enoyl)pyrrolidin-3-yl)-1H-pyrazolo[3,4-d]pyrimidine-3-carboxamide,

(37) (R,E)-4-amino-N-(5-chlorobenzo[d]oxazol-2-yl)-1-(1-(4-(piperidin-1-yl)but-2-enoyl)pyrrolidin-3-yl)-1H-pyrazolo[3,4-d]pyrimidine-3-carboxamide,

(38) (R)-1-(1-acryloylpyrrolidin-3-yl)-4-amino-N-(5-methoxybenzo[d]oxazol-2-yl)-1H-pyrazol o[3,4-d]pyrimidine-3-carboxamide,

(39) (R)-1-(1-acryloylpyrrolidin-3-yl)-4-amino-N-(5-cyanobenzo[d]oxazol-2-yl)-1H-pyrazolo[3,4-d]pyrimidine-3-carboxamide,

(40) (R)-1-(1-acryloylpyrrolidin-3-yl)-4-amino-N-(5-(2-methoxyethyl)benzo[d]oxazol-2-yl)-1H-pyrazolo[3,4-d]pyrimidine-3-carboxamide,

(41) (R)-1-(1-acryloylpyrrolidin-3-yl)-4-amino-N-(5-phenylbenzo[d]oxazol-2-yl)-1H-pyrazolo[3,4-d]pyrimidine-3-carboxamide,

(42) (R,E)-4-amino-N-(5-phenylbenzo[d]oxazol-2-yl)-1-(1-(4-(dimethylamino)but-2-enoyl)pyrrolidin-3-yl)-1H-pyrazolo[3,4-d]pyrimidine-3-carboxamide,

(43) (R)-1-(1-acryloylpyrrolidin-3-yl)-4-amino-N-(5-(trifluoromethyl)benzo[d]oxazol-2-yl)-1H-pyrazolo[3,4-d]pyrimidine-3-carboxamide,

(44) (R,E)-4-amino-N-(5-(trifluoromethyl)benzo[d]oxazol-2-yl)-1-(1-(4-(dimethylamino)but-2-enoyl)pyrrolidin-3-yl)-1H-pyrazol o[3,4-d]pyrimidine-3-carboxamide,

(45) 1-(1-acryloylazetidin-3-yl)-4-amino-N-(5-chlorobenzo[d]oxazol-2-yl)-1H-pyrazolo[3,4-d]pyrimidine-3-carboxamide,

(46) 7-(1-acryloylazetidin-3-yl)-4-amino-N-(5-chlorobenzo[d]oxazol-2-yl)-7H-pyrrol o[2,3-d]pyrimidine-5-carboxamide,

(47) (E)-4-amino-N-(5-chlorobenzo[d]oxazol-2-yl)-7-(1-(4-(dimethylamino)but-2-enoyl)azetidin-3-yl) 7H-pyrrolo[2,3-d]pyrimidine-5-carboxamide,

(48) (R)-7-(1-acryloylpyrrolidin-3-yl)-4-amino-N-(5-chlorobenzo[d]oxazol-2-yl)-7H-pyrrolo[2,3-d]pyrimidine-5-carboxamide,

(49) (R,E)-4-amino-N-(5-chlorobenzo[d]oxazol-2-yl)-7-(1-(4-(dimethylamino)but-2-enoyl)pyrrolidin-3-yl) 7H-pyrrolo[2,3-d]pyrimidine-5-carboxamide,

(50) (R,E)-4-amino-N-(5-chlorobenzo[d]oxazol-2-yl)-7-(1-(4-(ethyl(methyl)amino)but-2-enoyl)pyrrolidin-3-yl) 7H-pyrrolo[2,3-d]pyrimidine-5-carboxamide,

(51) (R,E)-4-amino-N-(5-chlorobenzo[d]oxazol-2-yl)-7-(1-(4-(diethylamino)but-2-enoyl)pyrrolidin-3-yl) 7H-pyrrolo[2,3-d]pyrimidine-5-carboxamide,

(52) (R,E)-4-amino-N-(5-chlorobenzo[d]oxazol-2-yl)-7-(1-(4-(isopropyl(methyl)amino)but-2-enoyl)pyrrolidin-3-yl) 7H-pyrrolo[2,3-d]pyrimidine-5-carboxamide,

(53) (R,E)-4-amino-N-(5-chlorobenzo[d]oxazol-2-yl)-7-(1-(4-(pyrrolidin-1-yl)but-2-enoyl)pyrrolidin-3-yl) 7H-pyrrolo[2,3-d]pyrimidine-5-carboxamide,

(54) (R,E)-4-amino-N-(5-chlorobenzo[d]oxazol-2-yl)-7-(1-(4-(piperidin-1-yl)but-2-enoyl)pyrrolidin-3-yl) 7H-pyrrolo[2,3-d]pyrimidine-5-carboxamide,

(55) (R)-7-(1-acryloylpyrrolidin-3-yl)-4-amino-N-(5-phenylbenzo[d]oxazol-2-yl)-7H-pyrrolo[2,3-d]pyrimidine-5-carboxamide,

(56) (R,E)-4-amino-N-(5-phenylbenzo[d]oxazol-2-yl)-7-(1-(4-(dimethylamino)but-2-enoyl)pyrrolidin-3-yl) 7H-pyrrolo[2,3-d]pyrimidine-5-carboxamide,

(57) (R,E)-4-amino-N-(5-phenylbenzo[d]oxazol-2-yl)-7-(1-(4-(ethyl(methyl)amino)but-2-enoyl)pyrrolidin-3-yl) 7H-pyrrolo[2,3-d]pyrimidine-5-carboxamide,

(58) (R,E)-4-amino-N-(5-phenylbenzo[d]oxazol-2-yl)-7-(1-(4-(diethylamino)but-2-enoyl)pyrrolidin-3-yl) 7H-pyrrolo[2,3-d]pyrimidine-5-carboxamide,

(59) (R,E)-4-amino-N-(5-phenylbenzo[d]oxazol-2-yl)-7-(1-(4-(isopropyl(methyl)amino)but-2-enoyl)pyrrolidin-3-yl) 7H-pyrrolo[2,3-d]pyrimidine-5-carboxamide,

(60) (R,E)-4-amino-N-(5-phenylbenzo[d]oxazol-2-yl)-7-(1-(4-(pyrrolidin-1-yl)but-2-enoyl)pyrrolidin-3-yl) 7H-pyrrolo[2,3-d]pyrimidine-5-carboxamide,

(61) (R,E)-4-amino-N-(5-phenylbenzo[d]oxazol-2-yl)-7-(1-(4-(piperidin-1-yl)but-2-enoyl)pyrrolidin-3-yl) 7H-pyrrolo[2,3-d]pyrimidine-5-carboxamide, and a salt thereof.

10. The method of claim 1, wherein the immune disease is an allergic disease, an autoimmune disease, or an inflammatory disease.

11. The method of claim 1, wherein the immune disease is atopic dermatitis, rheumatoid arthritis, systemic lupus erythematosus, allergic rhinitis, or pollinosis.

12. The method of claim 1, wherein the immune disease is rheumatoid arthritis.

13. The method of claim 2, wherein the immune disease is an allergic disease, an autoimmune disease, or an inflammatory disease.

14. The method of claim 9, wherein the immune disease is an allergic disease, an autoimmune disease, or an inflammatory disease.

15. The method of claim 2, wherein the immune disease is atopic dermatitis, rheumatoid arthritis, systemic lupus erythematosus, allergic rhinitis, or pollinosis.

16. The method of claim 9, wherein the immune disease is atopic dermatitis, rheumatoid arthritis, systemic lupus erythematosus, allergic rhinitis, or pollinosis.

17. The method of claim 2, wherein the immune disease is rheumatoid arthritis.

18. The method of claim 4, wherein the immune disease is rheumatoid arthritis.

19. The method of claim 7, wherein the immune disease is rheumatoid arthritis.

20. The method of claim 9, wherein the immune disease is rheumatoid arthritis.

* * * * *